(12) United States Patent
Yoon et al.

(10) Patent No.: US 12,365,695 B2
(45) Date of Patent: Jul. 22, 2025

(54) FUSED RING HETEROARYL COMPOUNDS AS RIPK1 INHIBITORS

(71) Applicant: BiSiChem Co., Ltd., Gyeonggi-do (KR)

(72) Inventors: Cheolhwan Yoon, Gyeonggi-Do (KR); Jonghwan Bae, Gyeonggi-Do (KR); Namhee Kim, Gyeonggi-Do (KR); Cheolkyu Han, Gyeonggi-Do (KR); Jeongbeob Seo, Gyeonggi-Do (KR)

(73) Assignee: BiSiChem Co., Ltd., Geonggi-Do (KR)

( * ) Notice: Subject to any disclaimer, the term of this patent is extended or adjusted under 35 U.S.C. 154(b) by 0 days.

(21) Appl. No.: 16/987,906

(22) Filed: Aug. 7, 2020

(65) Prior Publication Data
US 2021/0040115 A1    Feb. 11, 2021

Related U.S. Application Data

(60) Provisional application No. 62/884,797, filed on Aug. 9, 2019.

(51) Int. Cl.
| | |
|---|---|
| C07D 498/04 | (2006.01) |
| A61P 35/00 | (2006.01) |
| C07D 403/12 | (2006.01) |
| C07D 413/12 | (2006.01) |
| C07D 487/04 | (2006.01) |

(52) U.S. Cl.
CPC .......... C07D 498/04 (2013.01); A61P 35/00 (2018.01); C07D 403/12 (2013.01); C07D 413/12 (2013.01); C07D 487/04 (2013.01)

(58) Field of Classification Search
None
See application file for complete search history.

(56) References Cited

U.S. PATENT DOCUMENTS 10,815,206 B2 * 10/2020 Masuda ............... C07D 267/14

FOREIGN PATENT DOCUMENTS

CN    109134448 A  * 1/2019  ............... A61P 1/16

OTHER PUBLICATIONS

Mingzhu et al. CN 109 134 448A—Translated Document, Apr. 2019, pp. 1-10.*
Ermine et al. Genes and Diseases, 2022, vol. 9, pp. 1579-1593.*
CN109134448, Jan. 4, 2019, pp. 1-10, English Translation.*
Patani et al. ((1996), Bioisosterism A rational approach in drug design, Chem. Rev., 96, 3147-3176 (Year: 1996).*
CN 109134448 (English Machine Translation) Details 05142024 (Year: 2018).*

* cited by examiner

*Primary Examiner* — Juliet C Switzer
*Assistant Examiner* — Dawanna Shar-Day White
(74) *Attorney, Agent, or Firm* — United One Law Group LLC; Kongsik Kim; Jhongwoo Peck

(57) ABSTRACT

The invention provides novel substituted heterocyclic compounds represented by Formula I, or a pharmaceutically acceptable salt, solvate, polymorph, ester, tautomer or prodrug thereof, and a composition comprising these compounds. The compounds provided can be used as inhibitors of RIPK1 and the therapeutic methods.

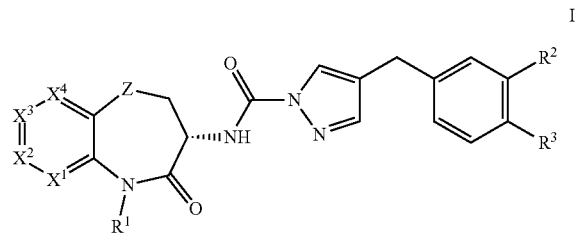

14 Claims, No Drawings
Specification includes a Sequence Listing.

FUSED RING HETEROARYL COMPOUNDS AS RIPK1 INHIBITORS

CROSS-REFERENCE TO RELATED APPLICATION

This application claims the priority to U.S. Provisional Application No. 62/884,797 filed on Aug. 9, 2019, which application is herein incorporated by reference in its entirety.

SEQUENCE LISTING

The present application contains a Sequence Listing which has been submitted electronically in ASCII format and is hereby incorporated by reference in its entirety. The ASCII copy, created on Mar. 24, 2025, is named Seq_LEE-P10004_ST25.txt and is 1,824 bytes in size.

TECHNICAL FIELD

This invention relates to a series of substituted heterocyclic compounds which are inhibitors of RIP1 kinase-mediated disease or disorder and use the therapeutics.

RELATED ART

Receptor-interacting protein-1 (RIP1) kinase is a serine/threonine protein kinase, referred to as RIPK1, RIP1 or RIP. RIP1 kinase has a crucial role whether the cell live or die. RIP1 is involved in the apoptosis and non-apoptotic cell death; necroptosis [1]. The intracellular domains of TNF receptor1 (TNFR1), FAS and TRAIL receptor 2 (TRAILR2) together include death domain (DD), they were stimulated by ligands tumor necrosis factor alpha (TNFα), Fas ligand (FASL) and TRAIL which recruit RIP1 and binding of their DD to that of RIP1. Stimulation of TNFR1 by TNFα leads to the formation of the complex I which leads to the activation of NF-kB has an important role in modulating the RIP1 of activation and activates an important cell survival program [2]. RIP1 activation can lead to cell death pathway by the formation of a RIP1-TNF receptor associated death domain protein (TRADD)-FAS-associated DD protein (FADD)-caspase 8 complexes (complex IIa), which stimulates caspase activation and leads to RIPK1-dependent apoptosis (RDA). [3-9]. If caspase-8 activity is blocked, the recruited protein receptor-interacting serine/threonine-protein kinase 3 (RIPK3) kinase which drives necroptosis by driving formation of a RIP1-RIP3-mixed lineage kinase domain-like (MLKL) complex (complex IIb), which drives the cell lysis and disruption of cell membrane [10-11].

Necroptosis and RIP1 have been serve a crucial checkpoint during embryonic development. The activation of necroptosis and RIP1 may represent an important pathological mechanism and implicated in many human diseases by mediating cell death and inflammation. Necroptosis may also has been related to disordered of pathogenesis of the central nervous system (CNS) diseases, atherosclerosis, Huntington's disease, colitis, steatohepatitis, acute hepatitis, stroke, myocardial infarction, the intestinal epithelium and skin. Therefore, necroptosis inhibitors are a crucial role for clinical drug development. [12-14]

Necroptosis can be inhibited by inactivating RIP1 kinases or RIP3 kinase. The first and often used inhibitor of necroptosis is RIP1-inhibitor necrostatin-1 (Nec-1). Nec-1 demonstrated efficiency in vitro and in vivo. Nec-1 ameliorated renal and brain ischemia/reperfusion injury, ConA-induced hepatitis, DSS-induced colitis and decreased the symptoms of Huntington's disease in a murine study [15-19].

Therefore, the synthesis potent selective inhibitors of RIP1 kinase can be treated of diseases, such as inflammation and necroptotic cell death. [20]

In recent, RIPL kinase inhibitors differ structurally from necrostatin class of compounds [21-22].

References cited above, each of which is hereby incorporated by reference in its entirety:
1. Degterev, A., Hitomi, J., Germscheid, M., Ch'en, I., Korkina, O., Teng, X., Abbott, D., Cuny, G., Yuan, C., Wagner, G., Hedrick, S., Gerber, S., Lugovskoy, A. and Yuan, J. Identification of RIP1 kinase as a specific cellular target of necrostatins. Nat Chem Biol. 4, 313-321 (2008).
2. Ofengeim, D. and Yuan, J. Regulation of RIP1 kinase signalling at the crossroads of inflammation and cell death. Nat. Rev. Mol. Cell Biol. 14, 727-736 (2013).
3. Shan, B., Pan, H., Najafov, A. and Yuan, J. Necroptosis in development and diseases. Genes Dev. 32, 327-340 (2018).
4. Vanden Berghe, T., Linkermann, A., Jouan-Lanhouet, S., Walczak, H. and Vandenabeele, P. Regulated necrosis: the expanding network of non-apoptotic cell death pathways. Nature reviews. Molecular cell biology. 15, 135-147 (2014).
5. Newton, K. RIPK1 and RIPK3: critical regulators of inflammation and cell death. Trends in cell biology. 25, 347-353 (2015).
6. de Almagro, M. C. and Vucic, D. Necroptosis: Pathway diversity and characteristics. Semin Cell Dev Biol. 39, 56-62 (2015).
7. O'Donnell, M. A., Legarda-Addison, D., Skountzos, P., Yeh, W. C. and Ting, A. T. Ubiquitination of RIP1 regulates an NF-kappaB-independent cell-death switch in TNF signaling. Curr Biol. 17, 418-424 (2007).
8. Feoktistova, M., Geserick, P., Kellert, B., Dimitrova, D. P., Langlais, C., Hupe, M., Cain, K., MacFarlane, M., Hacker, G. and Leverkus, M. cIAPs block Ripoptosome formation, a RIP1/caspase-8 containing intracellular cell death complex differentially regulated by cFLIP isoforms. Molecular cell. 43, 449-463 (2011).
9. Bertrand, M. J., Milutinovic, S., Dickson, K. M., Ho, W. C, Boudreault, A., Durkin, J., Gillard, J. W., Jaquith, J. B., Morris, S. J. and Barker, P. A. cIAP1 and cIAP2 facilitate cancer cell survival by functioning as E3 ligases that promote RIP1 ubiquitination. Mol Cell. 30, 689-700 (2008).
10. Cho, Y. S., Challa, S., Moquin, D., Genga, R., Ray, T. D., Guildford, M. and Chan, F. K. Phosphorylation-driven assembly of the RIP1-RIP3 complex regulates programmed necrosis and virus-induced inflammation. Cell. 137, 1112-1123 (2009).
11. Sun, L., Wang, H., Wang, Z., He, S., Chen, S., Liao, D., Wang, L., Yan, J., Liu, W., Lei, X. and Wang, X. Mixed lineage kinase domain-like protein mediates necrosis signaling downstream of RIP3 kinase. Cell. 148, 213-227 (2012).
12. Zhao, J., Jitkaew, S., Cai, Z., Choksi, S., Li, Q., Luo, J. and Liu, Z. G. Mixed lineage kinase domain-like is a key receptor interacting protein 3 downstream component of TNF-induced necrosis. Proceedings of the National Academy of Sciences of the United States of America. 109, 5322-5327 (2012).
13. Sun, L., Wang, H., Wang, Z., He, S., Chen, S., Liao, D., Wang, L., Yan, J., Liu, W., Lei, X. and Wang, X. Mixed 13. Lineage Kinase Domain-like Protein Mediates Necrosis Signaling Downstream of RIP3 Kinase. Cell. 148, 213-227 (2012).
14. Linkermann, A. and Green, D. R. Necroptosis. The New England journal of medicine. 370, 455-465 (2014).
15. Degterev, A., Huang, Z., Boyce, M., Li, Y., Jagtap, P., Mizushima, N. Cuny, G. D., Mitchison, T. J., Moskowitz, M. A. and Yuan, J. Chemical Inhibitor of Nonapoptotic Cell Death with Therapeutic Potential for Ischemic Brain Injury. Nat. Chem. Biol. 1, 112-119 (2005).
16. Linkermann, A., Brasen, J. H., Himmerkus, N., Liu, S., Huber, T. B., Kunzendorf, U. and Krautwald, S. Rip1 (Receptor-Interacting Protein Kinase 1) Mediates Necroptosis and Contributes to Renal Ischemia/Reperfusion Injury. Kidney Int. 81, 751-761 (2012).
17. Jouan-Lanhouet, S., Arshad, M. I., Piquet-Pellorce, C., Martin-Chouly, C., Le Moigne-Muller, G., Van Herreweghe, F., Takahashi, N., Sergent, O., Lagadic-Gossmann, D. and Vandenabeele, P. TRAIL Induces Necroptosis Involving RIPK1/RIPK3-Dependent PARP-1 Activation. Cell Death Differ. 19, 2003-2014 (2012).
18. Gunther, C., Martini, E., Wittkopf, N., Amann, K., Weigmann, B., Neumann, H., Waldner, M. J., Hedrick, S. M., Tenzer, S. and Neurath, M. F. Caspase-8 Regulates TNF-Alpha-Induced Epithelial Necroptosis and Terminal Ileitis. Nature. 477, 335-339 (2011).
19. Zhu, S., Zhang, Y., Bai, G. and Li, H. Necrostatin-1 Ameliorates Symptoms in R6/2 Transgenic Mouse Model of Huntington's Disease. Cell. Death Dis. 2, e115 (2011).
20. Newton, K., Dugger, D. L., Wickliffe, K. E., Kapoor, N., de Almagro, M. C, Vucic, D., Komuves, L., Ferrando, R. E., French, D. M., Webster, J., Roose-Girma, M., Warming, S. and Dixit, V. M. Activity of protein kinase RIPK3 determines whether cells die by necroptosis or apoptosis. Science. 343, 1357-1360 (2014).
21. Harris, P. A., Bandyopadhyay, D., Berger, S. B., Campobasso, N., Capriotti, C. A., Cox, J. A., Dare, L., Finger, J. N., Hoffman, S. J., Kahler, K. M., Lehr, R., Lich, J. D., Nagilla, R., Nolte, R. T., Ouellette, M. T., Pao, C. S., Schaeffer, M. C, Smallwood, A., Sun, H. H., Swift, B. A., Totoritis, R. D., Ward, P., Marquis, R. W., Bertin, J. and Gough, P. J. Discovery of Small Molecule RIP1 Kinase Inhibitors for the Treatment of Pathologies Associated with Necroptosis. ACS medicinal chemistry letters. 4, 1238-1243 (2013).
22. Najjar, M., Suebsuwong, C, Ray, S. S., Thapa, R. J., Maki, J. L., Nogusa, S., Shah, S., Saleh, D., Gough, P. J., Bertin, J., Yuan, J., Balachandran, S., Cuny, G. D. and Degterev, A. Structure Guided Design of Potent and Selective Ponatinib-Based Hybrid Inhibitors for RIPK1. Cell Rep. 24, 1850-1860 (2015).

SUMMARY

This invention provides a compound of formula I, or a pharmaceutically acceptable salt, solvate, polymorph, ester, tautomer or prodrug thereof:

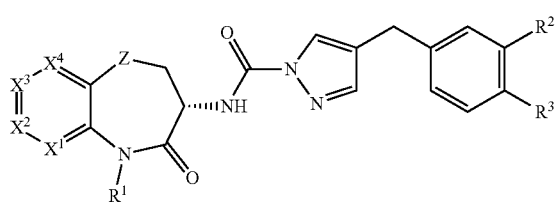

wherein
$R^1$ is H or optionally substituted C1-C6 alkyl;
$R^2$ and $R^3$ are each independently H, methyl, $CF_3$, halogen, or cyano;
$X^1$, $X^2$, $X^3$, and $X^4$ are each independently $CR^4$ or N;
$R^4$ is H, $NH_2$, OH, OMe, halogen, cyano, or C1-C6 alkyl;
Z is $CH_2$, $NR^1$, O, or S;
Compounds of Formula I further include the absolute configuration compounds of Formula IIa and IIb.

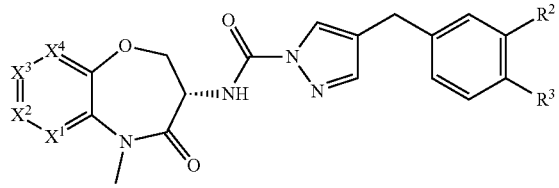

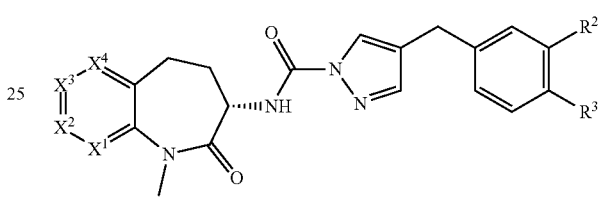

or salt thereof, wherein;
$X^1$, $X^2$, $X^3$, and $X^4$ are each independently $CR^4$ or N;
$R^4$ is H, $NH_2$, OH, OMe, halogen, cyano, or C1-C6 alkyl;
$R^2$ and $R^3$ are each independently H, methyl, $CF_3$, halogen, or cyano;

Compounds of present invention are inhibitors of the RIP1 kinase and, consequently, are useful for treating inflammatory bowel disease (including Crohn's disease and ulcerative colitis), psoriasis, retinal detachment, retinitis pigmentosa, arthritis (including rheumatoid arthritis, spondyloarthritis, gout, osteoarthritis, and systemic onset juvenile idiopathic arthritis (SoJIA)), transplant rejection, organ transplantation (for donors and recipients), multiple sclerosis, tumor necrosis factor receptor-associated periodic syndrome, multiple organ dysfunction syndrome (MODS), thermal injury/burn, systemic inflammatory response syndrome (SIRS), radiation injury, radiotherapy, chemotherapy, pneumonias, hemorrhagic shock, trauma (including multiple trauma), traumatic brain injury, acute pancreatitis, critical illness (in general), sepsis, septic shock, Stevens-Johnson syndrome, toxic epidermal necrolysis, stroke, heat stroke, stroke-associated pneumonia, Multi-Organ Dysfunction Syndrome (MODS), Acute Respiratory Distress Syndrome (ARDS), intestinal obstruction, liver cirrhosis, surgery, major abdominal operations, abdominal aortic aneurysm repair, large bowel resections, ischemia reperfusion injury (including ischemia reperfusion injury of solid organs, (gut, brain, liver, kidney), and limb ischemia), bowel ischemia (small intestine and large intestine), cardiac surgery requiring cardio-pulmonary bypass, autoimmune hepatitis, autoimmune hepatobiliary diseases, autoimmune ITP, Huntington's disease, Alzheimer's disease, ALS, Parkinson's disease, Lewy body disease, spinal muscular atrophy, allergic disease, asthma, atopic dermatitis, type I diabetes, Wegener's granulomatosis, Behcet's disease, interleukin-1 converting enzyme associated fever syndrome, pancreatic cancer, metastatic adenocarcinoma of the pancreas, pancreatic ductal adenocarcinoma, mesothelioma, melanoma, colorectal cancer, acute myeloid leukemia, metastasis, glioblastoma, breast cancer, gallbladder cancer, clear cell renal carcinoma, non-small cell lung carcinoma, and radiation induced necrosis.

In other aspects, the present invention is directed to a pharmaceutical composition comprising an effective amount of a compound of formula I or a pharmaceutically acceptable salt, solvate, polymorph, ester, tautomer or prodrug thereof. In some embodiments, the pharmaceutical composition further comprises a pharmaceutically acceptable carrier, adjuvants and/or excipients. In some embodiments, such a composition may contain at least one of preservatives, agents for delaying absorption, fillers, binders, adsorbents, buffers, disintegrating agents, solubilizing agents, and other carriers, adjuvants and/or excipients as inert ingredients. The composition may be formulated with a method well-known in the art.

In some aspects, the present invention is directed to a method of treating a disease in an individual suffering from said disease comprising administering to said individual a therapeutically effective amount of a composition comprising a compound of formula I or a pharmaceutically acceptable salt, solvate, polymorph, ester, tautomer or prodrug thereof.

In other aspects, the present invention is directed to a method of treating a disorder in a mammal, comprising administering to said mammal a therapeutically effective amount of a compound of formula I or a pharmaceutically acceptable salt, solvate, polymorph, ester, tautomer or prodrug thereof.

In other aspects, the present invention is directed to a method of treating a disorder in a human, comprising administering to said human a therapeutically effective amount of a compound of formula I or a pharmaceutically acceptable salt, solvate, polymorph, ester, tautomer or prodrug thereof.

In other aspects, RIP1 kinase-mediated diseases or disorders are described herein and include inflammatory bowel disease (including Crohn's disease and ulcerative colitis), psoriasis, retinal detachment, retinitis pigmentosa, arthritis (including rheumatoid arthritis, spondylarthritis, gout, osteoarthritis, and systemic onset juvenile idiopathic arthritis (SoJIA)), transplant rejection, organ transplantation (for donors and recipients), multiple sclerosis, tumor necrosis factor receptor-associated periodic syndrome, multiple organ dysfunction syndrome (MODS), thermal injury/burn, systemic inflammatory response syndrome (SIRS), radiation injury, radiotherapy, chemotherapy, pneumonias, hemorrhagic shock, trauma (including multiple trauma), traumatic brain injury, acute pancreatitis, critical illness (in general), sepsis, septic shock, Stevens-Johnson syndrome, toxic epidermal necrolysis, stroke, heat stroke, stroke-associated pneumonia, Multi-Organ Dysfunction Syndrome (MODS), Acute Respiratory Distress Syndrome (ARDS), intestinal obstruction, liver cirrhosis, surgery, major abdominal operations, abdominal aortic aneurysm repair, large bowel resections, ischemia reperfusion injury (including ischemia reperfusion injury of solid organs, (gut, brain, liver, kidney), and limb ischemia), bowel ischemia (small intestine and large intestine), cardiac surgery requiring cardio-pulmonary bypass, autoimmune hepatitis, autoimmune hepatobiliary diseases, autoimmune ITP, Huntington's disease, Alzheimer's disease, ALS, Parkinson's disease, Lewy body disease, spinal muscular atrophy, allergic disease, asthma, atopic dermatitis, type I diabetes, Wegener's granulomatosis, Behcet's disease, and interleukin-1 converting enzyme associated fever syndrome, In other aspects, the present invention is directed to a method of treating a pancreatic cancer, metastatic adenocarcinoma of the pancreas, pancreatic ductal adenocarcinoma, mesothelioma, melanoma, colorectal cancer, acute myeloid leukemia, metastasis, glioblastoma, breast cancer, gallbladder cancer, clear cell renal carcinoma, non-small cell lung carcinoma, and radiation induced necrosis certain the RIP1 kinase-mediated disease or disorder in a mammal, including a human, comprising administering to said mammal a therapeutically effective amount of a compound of formula I, or a pharmaceutically acceptable salt, ester, prodrug, solvate, such as hydrate, polymorph or tautomer thereof.

In other aspects, the present invention is directed to a method of treating a disorder or condition which is modulated by the RIP1 kinase in a mammal, including a human, comprising administering to said mammal an amount of the compound of formula I, or a pharmaceutically acceptable salt, ester, prodrug, solvate, such as hydrate, polymorph or tautomer thereof, effective to modulate said cascade. The appropriate dosage for a particular patient can be determined, according to known methods, by those skilled in the art.

In other aspects, the present invention is directed to use of compound of formula I or a pharmaceutically acceptable salt, ester, prodrug, solvate, such as hydrate, polymorph or tautomer thereof in the preparation of a pharmaceutical composition. The pharmaceutical composition can be used for treating a disorder or condition which is modulated by the RIP1 kinase in a mammal, including a human.

In other aspects, the present invention is directed to a pharmaceutical composition comprising a compound of formula I or a pharmaceutically acceptable salt, solvate, polymorph, ester, tautomer or prodrug thereof. In some embodiments, the pharmaceutical composition is in a form suitable for oral administration. In further or additional embodiments, the pharmaceutical composition is in the form of a tablet, capsule, pill, powder, sustained release formulation, solution and suspension. In some embodiments, the pharmaceutical composition is in a form suitable for parenteral injection, such as a sterile solution, suspension or emulsion; for topical administration as an ointment or cream or for rectal administration as a suppository. In further or additional embodiments, the pharmaceutical composition is in unit dosage forms suitable for single administration of precise dosages. In further or additional embodiments, the amount of compound of formula I is in the range of about 0.001 to about 1000 mg/kg body weight/day. In further or additional embodiments, the amount of compound of formula I is in the range of about 0.5 to about 50 mg/kg body weight/day.

In other aspects, the present invention is directed to a process for preparing a compound of formula I or a pharmaceutically acceptable salt, solvate, polymorph, ester, tautomer or prodrug thereof.

DETAILED DESCRIPTION

The novel features of the invention are set forth with particularity in the appended claims. A better understanding of the features and advantages of the present invention will be obtained by reference to the following detailed description that sets forth illustrative embodiments, in which the principles of the invention are utilized.

While preferred embodiments of the present invention have been shown and described herein such embodiments are provided by way of example only. It should be understood that various alternatives to the embodiments of the invention described herein may be employed in practicing the invention. Those ordinary skilled in the art will appreciate that numerous variations, changes, and substitutions are possible without departing from the invention. It is intended that the following claims define the scope of aspects of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Certain Chemical Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Unless otherwise noted, the use of general chemical terms, such as though not limited to "alkyl," "amine," "aryl," are equivalent to their optionally substituted forms. For example, "alkyl," as used herein, includes optionally substituted alkyl.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, an optionally substituted group may be un-substituted (e.g., $CH_2CH_3$), fully substituted (e.g., $CF_2CF_3$), mono-substituted (e.g., $CH_2CH_2F$) or substituted at a level anywhere in-between fully substituted and mono-substituted (e.g., $CH_2CHF_2$, $CF_2CH_3$, $CFHCHF_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

As used herein, $C_1$-$C_n$, includes $C_1$-$C_2$, $C_1$-$C_3$, ... $C_1$-$C_n$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, isobutyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The terms "heteroatom" or "hetero" as used herein, alone or in combination, refer to an atom other than carbon and hydrogen. Heteroatoms are independently selected from among oxygen, nitrogen, sulfur, phosphorous, silicon, selenium and tin but are not limited to these atoms. In embodiments in which two or more heteroatoms are present, the two or more heteroatoms can be the same as each another, or some or all of the two or more heteroatoms can each be different from the others.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The term "aliphatic" as used herein, alone or in combination, refers to an optionally substituted, straight-chain or branched-chain, non-cyclic, saturated, partially unsaturated, or fully unsaturated nonaromatic hydrocarbon. Thus, the term collectively includes alkyl, alkenyl and alkynyl groups.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "cycloalkyl" as used herein, alone or in combination, refers to an optionally substituted, saturated, hydrocarbon monoradical ring, containing from three to about fifteen ring carbon atoms or from three to about ten ring carbon atoms, though may include additional, non-ring carbon atoms as substituents (e.g. methylcyclopropyl).

A non-limiting example of "cycloalkyl" includes azinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo [4. 1.0]heptyl, 3H-indolyl and quinolizinyl and the like. The terms also include all ring forms of the carbohydrates, including but not limited to the monosaccharides, the disaccharides and the oligosaccharides.

The term "aromatic" as used herein, refers to a planar, cyclic or polycyclic, ring moiety having a delocalized $\pi$-electron system containing 4n+2 $\pi$ electrons, where n is an integer. Aromatic rings can be formed by five, six, seven, eight, nine, or more than nine atoms. Aromatics can be optionally substituted and can be monocyclic or fused-ring polycyclic. The term aromatic encompasses both all carbon containing rings (e.g., phenyl) and those rings containing one or more heteroatoms (e.g., pyridine).

Certain Pharmaceutical Terminology

The term "RIP1 kinase inhibitor" as used herein refers to a compound that exhibits an $IC_{50}$, with respect to RIP1 kinase activity, of no more than about 100 µM or not more than about 50 M, as measured in the kinase assay described generally herein. "$IC_{50}$" is that concentration of inhibitor which reduces the activity of an enzyme to half-maximal level. Compounds described herein have been discovered to exhibit inhibition against RIPK1. Compounds of the present invention preferably exhibit an $IC_{50}$ with respect to RIPK1 of no more than about 10 µM, more preferably, no more than about 5 µM, even more preferably not more than about 1 µM, and most preferably, not more than about 200 nM, as measured in the kinase assay described herein.

The term "selective," "selectively," or "selectivity" as used herein refers to a compound of this invention having a lower $IC_{50}$ value for the enzyme as compared to any other enzymes (e.g., at least 2, 5, 10 or more-fold lower).

The term "subject", "patient" or "individual" as used herein in reference to individuals suffering from a disorder, a condition, and the like, encompasses mammals and non-mammals.

Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical Sciences (current edition), Mack Publishing Co., Easton, Pa. In preferred embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively nontoxic chemical compounds or agents that facilitate the incorporation of a compound into cells or tissues.

The term "agonist," as used herein, refers to a molecule such as a compound, a drug, an enzyme activator or a hormone modulator which enhances the activity of another molecule or the activity of a receptor site.

The term "antagonist," as used herein, refers to a molecule such as a compound, a drug, an enzyme inhibitor, or a hormone modulator, which diminishes, or prevents the action of another molecule or the activity of a receptor site.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the invention, or by separately reacting a purified compound in its free base form with a suitable organic or inorganic acid, and isolating the salt thus formed. Examples of pharmaceutically acceptable salts include those salts prepared by reaction of the compounds described herein with a mineral or organic acid or an inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds of the invention and their pharmaceutically acceptable acid addition salts (See examples at Berge et al., *J. Pharm. Sci.* 1977, 66, 1-19.). Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like.

Illustrative examples of bases include sodium hydroxide, potassium hydroxide, choline hydroxide, sodium carbonate, and the like. Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they may contain. Water or oil-soluble or dispersible products may be obtained by such quaternization. See, for example, Berge et al., supra.

The term "solvate" as used herein refers to a combination of a compound of this invention with a solvent molecule formed by solvation. In some situations, the solvate refers to a hydrate, i.e., the solvent molecule is a water molecule, the combination of a compound of this invention and water forms a hydrate.

The term "polymorph" or "polymorphism" as used herein refers to a compound of this invention present in different crystal lattice forms.

The term "ester" as used herein refers to a derivative of a compound of this invention derived from an oxoacid group and a hydroxyl group, either one of which can be present at the compound of this invention.

The term "tautomer" as used herein refers to an isomer readily interconverted from a compound of this invention by e.g., migration of a hydrogen atom or proton.

The term "pharmaceutically acceptable derivative or prodrug" as used herein, refers to any pharmaceutically acceptable salt, ester, salt of an ester or other derivative of a compound of this invention, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

Pharmaceutically acceptable prodrugs of the compounds described herein include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Various forms of prodrugs are well known in the art. See for example *Design of Prodrugs*, Bundgaard, A. Ed., Elseview, 1985 and *Method in Enzymology*, Widder, K. et al., Ed.; Academic, 1985, vol. 42, p. 309-396; Bundgaard, H. "Design and Application of Prodrugs" in *A Textbook of Drug Design and Development*, Krosgaard-Larsen and H. Bundgaard, Ed., 1991, Chapter 5, p. 113-191; and Bundgaard, H., *Advanced Drug Delivery Review*, 1992, 8, 1-38, each of which is incorporated herein by reference. The prodrugs described herein include, but are not limited to, the following groups and combinations of these groups; amine derived prodrugs: Hydroxy prodrugs include, but are not limited to acyloxyalkyl esters, alkoxycarbonyloxyalkyl esters, alkyl esters, aryl esters and disulfide containing esters.

The terms "enhance" or "enhancing," as used herein, means to increase or prolong either in potency or duration of a desired effect. Thus, in regard to enhancing the effect of therapeutic agents, the term "enhancing" refers to the ability to increase or prolong, either in potency or duration, the effect of other therapeutic agents on a system.

An "enhancing-effective amount," as used herein, refers to an amount adequate to enhance the effect of another therapeutic agent in a desired system.

The terms "pharmaceutical combination", "administering an additional therapy", "administering an additional therapeutic agent" and the like, as used herein, refer to a pharmaceutical therapy resulting from mixing or combining more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent(s) are administered in a single composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from *The Pharmacological Basis of Therapeutics*, 9th Edition, McGraw-Hill (1996).

Experimental Part

NMR spectra were recorded in $CDCl_3$, DMSO-$d_6$ or $CD_3OD$ solution in 5-mm o.d. tubes (Norell, Inc. 507-HP) at 30° C. and were collected on Varian VNMRS-400 at 400 MHz for $^1H$. The chemical shifts (δ) are relative to tetramethylsilane (TMS=0.00 ppm) and expressed in ppm. LC/MS was taken on Ion-trap Mass Spectrometer on FINNIGAN Thermo or ISQ EC, Thermo Fisher U3000 RSLC (Column: YMC Hydrosphere (C18, Ø4.6×50 mm, 3 μm, 120 Å, 40° C.) operating in ESI(+) ionization mode; flow rate=1.0 mL/min. Mobile phase=0.01% heptafluorobutyric acid (HFBA) and 1.0% isopropyl alcohol (IPA) in water or $CH_3CN$.

General Synthetic Scheme for Pyrazole Intermediates

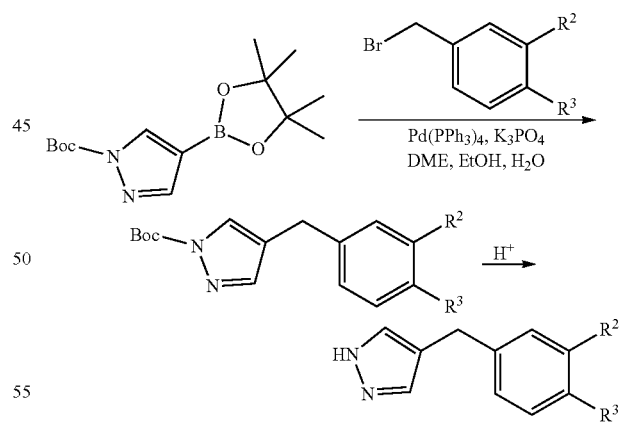

Intermediate 1: 4-benzyl-1H-pyrazole

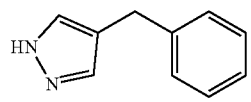

Step A: tert-butyl 4-benzyl-1H-pyrazole-1-carboxylate

To a solution of tert-butyl 4-(4,4,5,5-tetramethyl-1,3,2-dioxaborolan-2-yl)-1H-pyrazole-1-carboxylate (4.50 g, 15.3 mmol), $K_3PO_4$ (9.74 g, 45.9 mmol) and (bromomethyl)benzene (2.62 g, 15.3 mmol) in a mixture of DME (30 mL), EtOH (7.5 mL) and $H_2O$ (7.5 mL) was added $Pd(PPh_3)_4$ (2.30 g, 1.99 mmol) at room temperature. The reaction mixture was stirred at 55° C. for 16 hours. After diluted with water, the mixture was extracted with EtOAc twice. The combined organic layers were dried over $Na_2SO_4$, filtered and concentrated in vacuo. The residue was purified by column chromatography on $SiO_2$ (pet.Ether:EtOAc=10:1) to afford tert-butyl 4-benzyl-1H-pyrazole-1-carboxylate (2.20 g, 55%) as a colorless oil. $^1$H-NMR (400 MHz, $CDCl_3$): δ 7.98 (1H, s), 7.65 (1H, s), 7.14-7.12 (2H, m), 6.99-6.95 (3H, m), 3.70 (2H, s), 1.50 (9H, s).

Step B: 4-benzyl-1H-pyrazole

To a solution of tert-butyl 4-benzyl-1H-pyrazole-1-carboxylate (2.20 g, 8.52 mmol) in EtOAc (5.0 mL) was added HCl (3.0 M in EtOAc, 8.5 mL, 26 mmol) at room temperature. The reaction mixture was stirred at room temperature for 3 hours. A precipitated solid was collected by filtration, washed with EtOAc, and dried under vacuum to afford 4-benzyl-1H-pyrazole (1.18 g, 71%) as a white solid. $^1$H-NMR (400 MHz, DMSO-$d_6$): δ 13.0 (2H, brs), 7.91 (2H, s), 7.31-7.27 (2H, m), 7.22-7.17 (3H, m), 3.80 (2H, s).

Intermediate 2: 4-(3-fluorobenzyl)-1H-pyrazole

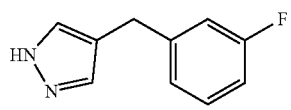 [SMILES: Fc1cccc(Cc2cn[nH]c2)c1]

Step A: tert-butyl 4-(3-fluorobenzyl)-1H-pyrazole-1-carboxylate

To a solution of tert-butyl 4-(4,4,5,5-tetramethyl-1,3,2-dioxaborolan-2-yl)-1H-pyrazole-1-carboxylate (1.50 g, 5.10 mmol), $K_3PO_4$ (3.25 g, 15.3 mmol) and 1-(bromomethyl)-3-fluorobenzene (964 mg, 5.10 mmol) in a mixture of DME (20 mL), EtOH (5.0 mL) and $H_2O$ (5.0 mL) was added $Pd(PPh_3)_4$ (766 mg, 0.663 mmol) at room temperature. The reaction mixture was stirred at 55° C. for 16 hours. After diluted with water, the mixture was extracted with EtOAc twice. The combined organic layers were dried over $Na_2SO_4$, filtered and concentrated in vacuo. The residue was purified by column chromatography on $SiO_2$ (pet. Ether:EtOAc=5:1) to afford tert-butyl 4-(3-fluorobenzyl)-1H-pyrazole-1-carboxylate (600 mg, 43%) as a yellow oil. LC-MS: m/z=177 [M+H-Boc]$^+$.

Step B: 4-(3-fluorobenzyl)-1H-pyrazole

To a solution of tert-butyl 4-(3-fluorobenzyl)-1H-pyrazole-1-carboxylate (600 mg, 2.17 mmol) in EtOAc (2.0 mL) was added HCl (3.0 M in EtOAc, 2.0 mL, 6.00 mmol) at room temperature. The reaction mixture was stirred at room temperature for 3 hours. The mixture was concentrated in vacuo. The residue was purified by prep-HPLC (neutral) to afford 4-(3-fluorobenzyl)-1H-pyrazole (133 mg, 35%) as a white solid. $^1$H-NMR (400 MHz, DMSO-$d_6$): δ 12.60 (1H, s), 7.45-7.28 (3H, m), 7.06-6.96 (3H, m), 3.80 (2H, s).

Intermediate 3: 4-(3-chlorobenzyl)-1H-pyrazole hydrochloride

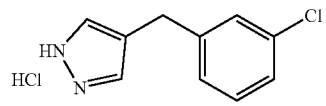

Step A: tert-butyl 4-(3-chlorobenzyl)-1H-pyrazole-1-carboxylate

To a solution of tert-butyl 4-(4,4,5,5-tetramethyl-1,3,2-dioxaborolan-2-yl)-1H-pyrazole-1-carboxylate (1.50 g, 5.10 mmol), $K_3PO_4$ (3.25 g, 15.3 mmol) and 1-(bromomethyl)-3-chlorobenzene (1.05 g, 5.10 mmol) in a mixture of DME (20 mL), EtOH (5.0 mL) and $H_2O$ (5.0 mL) was added $Pd(PPh_3)_4$ (766 mg, 0.66 mmol) at room temperature. The reaction mixture was stirred at 55° C. for 16 hours and cooled to room temperature. After diluted with water, the mixture was extracted with EtOAc twice. The combined organic layers were dried over $Na_2SO_4$, filtered and concentrated in vacuo. The residue was purified by column chromatography on $SiO_2$ (pet. Ether:EtOAc=5:1) to afford tert-butyl 4-(3-chlorobenzyl)-1H-pyrazole-1-carboxylate (500 mg, 33%) as a yellow oil. LC-MS: m/z=193 [M+H-Boc]$^+$.

Step B: 4-(3-chlorobenzyl)-1H-pyrazole hydrochloride

To a solution of tert-butyl 4-(3-chlorobenzyl)-1H-pyrazole-1-carboxylate (500 mg, 1.71 mmol) in EtOAc (3.0 mL) was added HCl (3.0 M in EtOAc, 3.0 mL, 9.0 mmol) at room temperature. The reaction mixture was stirred at room temperature for 3 hours and concentrated in vacuo. The residue was purified by prep-HPLC (neutral) to afford 4-(3-chlorobenzyl)-1H-pyrazole, which was changed to the corresponding HCl salt form by adding several drops of HCl (1 M in water). The mixture was lyophilized followed by dried under vacuum to afford 4-(3-chlorobenzyl)-1H-pyrazole hydrochloride (92 mg, 24%) as a white solid. $^1$H-NMR (400 MHz, DMSO-$d_6$): δ 10.75 (2H, br), 7.76 (2H, s), 7.33-7.28 (2H, m), 7.26-7.19 (2H, m), 3.84 (2H, s).

Intermediate 4: 4-(3-methylbenzyl)-1H-pyrazole hydrochloride

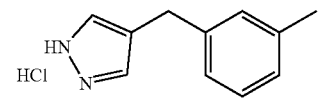

Step A: tert-butyl 4-(3-methylbenzyl)-1H-pyrazole-1-carboxylate

To a solution of tert-butyl 4-(4,4,5,5-tetramethyl-1,3,2-dioxaborolan-2-yl)-1H-pyrazole-1-carboxylate (1.00 g, 3.40 mmol), K$_3$PO$_4$ (2.17 g, 10.2 mmol) and 1-(bromomethyl)-3-methylbenzene (629 mg, 3.40 mmol) in a mixture of DME (20 mL), EtOH (5.0 mL) and H$_2$O (5.0 mL) was added Pd(PPh$_3$)$_4$ (511 mg, 0.442 mmol) at room temperature. The reaction mixture was stirred at 55° C. for 16 hours and cooled to room temperature. After diluted with water, the mixture was extracted with EtOAc twice. The combined organic layers were dried over Na$_2$SO$_4$, filtered and concentrated in vacuo. The residue was purified by column chromatography on SiO$_2$ (pet. Ether:EtOAc=5:1) to afford tert-butyl 4-(3-methylbenzyl)-1H-pyrazole-1-carboxylate (500 mg, 54%) as a yellow oil. $^1$H-NMR (400 MHz, CDCl$_3$): δ 7.98 (1H, s), 7.65 (1H, s), 7.14-7.12 (1H, m), 6.99-6.95 (3H, m), 3.70 (2H, s), 2.26 (3H, s), 1.50 (9H, s).

Step B: 4-(3-methylbenzyl)-1H-pyrazole hydrochloride

To a solution of tert-butyl 4-(3-methylbenzyl)-1H-pyrazole-1-carboxylate (500 mg, 1.84 mmol) in EtOAc (2.0 mL) was added HCl (3.0 M in EtOAc, 2.0 mL, 6.0 mmol) at room temperature. The reaction mixture was stirred at room temperature for 3 hours. A precipitated solid was collected by filtration, washed with EtOAc, and dried under vacuum to afford 4-(3-methylbenzyl)-1H-pyrazole hydrochloride (297 mg, 78%) as a white solid. $^1$H-NMR (400 MHz, DMSO-d$_6$): δ 13.21 (2H, br), 7.91 (2H, s), 7.19-7.15 (1H, m), 7.04-6.99 (3H, m), 3.80 (2H, s), 2.26 (3H, s).

Intermediate 5:
4-(3-(trifluoromethyl)benzyl)-1H-pyrazole hydrochloride

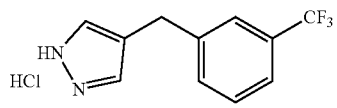 [SMILES: Cl ; FC(F)(F)c1cccc(Cc2cn[nH]c2)c1]

Step A: tert-butyl 4-(3-(trifluoromethyl)benzyl)-1H-pyrazole-1-carboxylate

To a solution of tert-butyl 4-(4,4,5,5-tetramethyl-1,3,2-dioxaborolan-2-yl)-1H-pyrazole-1-carboxylate (1.50 g, 5.10 mmol), K$_3$PO$_4$ (3.25 g, 15.3 mmol) and 1-(bromomethyl)-3-(trifluoromethyl)benzene (1.22 g, 5.10 mmol) in a mixture of DME (20 mL), EtOH (5.0 mL) and H$_2$O (5.0 mL) was added Pd(PPh$_3$)$_4$ (766 mg, 0.66 mmol) at room temperature. The reaction mixture was stirred at 55° C. for 16 hours and cooled to room temperature. After diluted with water, the mixture was extracted with EtOAc twice. The combined organic layers were dried over Na$_2$SO$_4$, filtered and concentrated in vacuo. The residue was purified by column chromatography on SiO$_2$ (pet. Ether:EtOAc=5:1) to afford tert-butyl 4-(3-(trifluoromethyl)benzyl)-1H-pyrazole-1-carboxylate (800 mg, 48%) as a yellow oil. LC-MS: m/z=227 [M+H−Boc]$^+$.

Step B: 4-(3-(trifluoromethyl)benzyl)-1H-pyrazole hydrochloride

To a solution of tert-butyl 4-(3-fluorobenzyl)-1H-pyrazole-1-carboxylate (800 mg, 2.45 mmol) in EtOAc (3.0 mL) was added HCl (3.0 M in EtOAc, 3.0 mL, 9.0 mmol) at room temperature. The reaction mixture was stirred at room temperature for 3 hours. After concentration in vacuo, the residue was purified by prep-HPLC (neutral) to afford 4-(3-fluorobenzyl)-1H-pyrazole, which was treated with several drops of HCl (1 M in water) followed by lyophilization and dried under vacuum to afford 4-(3-(trifluoromethyl)benzyl)-1H-pyrazole hydrochloride (72 mg, 11%) as a white solid. $^1$H-NMR (400 MHz, DMSO-d$_6$): δ 8.50 (2H, brs), 7.69-7.68 (2H, s), 7.56-7.53 (4H, m), 3.92 (2H, s).

Intermediate 6:
3-((1H-pyrazol-4-yl)methyl)benzonitrile

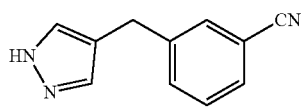

Step A: tert-butyl 4-(3-cyanobenzyl)-1H-pyrazole-1-carboxylate

To a solution of tert-butyl 4-(4,4,5,5-tetramethyl-1,3,2-dioxaborolan-2-yl)-1H-pyrazole-1-carboxylate (2.00 g, 6.80 mmol) in DME (56 mL), EtOH (14 mL) and H$_2$O (14 mL) was added 4-(bromomethyl)benzonitrile (1.33 g, 6.80 mmol), K$_3$PO$_4$ (4.32 g, 20.4 mmol) and Pd(PPh$_3$)$_4$ (1.01 g, 0.880 mmol) at room temperature. The reaction mixture was stirred at 55° C. for 20 hours. After evaporation of DME and EtOH, the residue was extracted with EtOAc twice. The combined organic layers were dried over Na$_2$SO$_4$, filtered, concentrated to afford tert-butyl 4-(3-cyanobenzyl)-1H-pyrazole-1-carboxylate (1.80 g, 93%) as a colorless oil. LC-MS: m/z=184 (M+H−Boc)$^+$.

Step B: 3-((1H-pyrazol-4-yl)methyl)benzonitrile

To a solution of tert-butyl 4-(3-cyanobenzyl)-1H-pyrazole-1-carboxylate (1.80 g, 6.36 mmol) in DCM (10 mL) was added TFA (5.0 mL, 65 mmol) at room temperature. The reaction mixture was stirred at room temperature for 20 hours. After neutralization with saturated aq. Na$_2$CO$_3$ solution, the resulting mixture was extracted with DCM twice. The combined organic layers were dried over Na$_2$SO$_4$ and concentrated in vacuo. The residue was purified by prep-HPLC to afford 3-((1H-pyrazol-4-yl)methyl)benzonitrile (101 mg, 9%) as a white solid. $^1$H-NMR (400 MHz, DMSO-d$_6$+D$_2$O): δ 7.65-7.62 (2H, m), 7.60-7.58 (1H, m), 7.52-7.48 (3H, m), 3.89 (2H, s).

Intermediate 7: 4-(4-fluorobenzyl)-1H-pyrazole

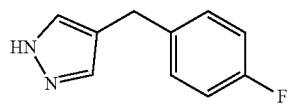 [SMILES: Fc1ccc(Cc2cn[nH]c2)cc1]

Step A: tert-butyl 4-(3-cyanobenzyl)-1H-pyrazole-1-carboxylate

To a solution of tert-butyl 4-(4,4,5,5-tetramethyl-1,3,2-dioxaborolan-2-yl)-1H-pyrazole-1-carboxylate (860 mg, 2.92 mmol), K$_3$PO$_4$ (1.86 g, 8.76 mmol) and 1-(bromomethyl)-4-fluorobenzene (552 mg, 2.92 mmol) in a mixture of DME (12 mL), EtOH (3.0 mL) and H₂O (3.0 mL) was added Pd(PPh₃)₄ (438 mg, 0.379 mmol) at room temperature. The reaction mixture was stirred at 55° C. for 16 hours. After evaporation of DME and EtOH, the residue was extracted with EtOAc twice. The combined organic layers were dried over Na₂SO₄, filtered and concentrated in vacuo. The residue was purified by column chromatography on SiO₂ (pet. Ether:EtOAc=1:5) to afford tert-butyl 4-(4-fluorobenzyl)-1H-pyrazole-1-carboxylate (500 mg, 62%) as a yellow solid. ¹H-NMR (400 MHz, CDCl₃): δ 7.81 (11H, s), 7.53 (1H, s), 7.16-7.12 (2H, m), 7.00-6.95 (2H, m), 3.79 (2H, s), 1.63 (9H, s).

Step B: 4-(4-fluorobenzyl)-1H-pyrazole

To a solution of tert-butyl 4-(4-fluorobenzyl)-11H-pyrazole-1-carboxylate (400 mg, 1.45 mmol) in EtOAc (5.0 mL) was added HCl (3.0 M in EtOAc, 1.5 mL, 4.5 mmol) at room temperature. The reaction mixture was stirred at room temperature for 3 hours. After concentration in vacuo, the residue was purified by prep-HPLC (neutral) to afford 4-(4-fluorobenzyl)-1H-pyrazole (182 mg, 71%) as a white solid. ¹H-NMR (400 MHz, DMSO-d₆): δ 12.58 (11H, s), 7.41 (2H, s), 7.25-7.21 (2H, m), 7.11-7.05 (2H, m), 3.76 (2H, s).

Intermediate 8: 4-(4-fluorobenzyl)-1H-pyrazole

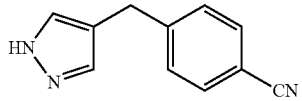 [SMILES: N#Cc1ccc(Cc2cn[nH]c2)cc1]

Step A: tert-butyl 4-(3-cyanobenzyl)-1H-pyrazole-1-carboxylate

To a solution of tert-butyl 4-(4,4,5,5-tetramethyl-1,3,2-dioxaborolan-2-yl)-1H-pyrazole-1-carboxylate (2.00 g, 6.80 mmol) in a mixture of DME (56 mL), EtOH (14 mL) and H₂O (14 mL) was added 4-(bromomethyl)benzonitrile (1.33 g, 6.80 mmol), K₃PO₄ (4.32 g, 20.4 mmol) and Pd(PPh₃)₄ (1.02 g, 0.88 mmol) at room temperature. The reaction mixture was stirred at 55° C. for 20 hours. After evaporation of DME and EtOH, the residue was extracted with EtOAc twice. The combined organic layers were dried over Na₂SO₄, filtered, and concentrated to afford tert-butyl 4-(4-fluorobenzyl)-1H-pyrazole-1-carboxylate (1.50 g, 78%) as an off-white solid. LC-MS: m/z=184 (M+H−Boc)⁺.

Step B: 4-(4-fluorobenzyl)-1H-pyrazole

To a solution of tert-butyl 4-(4-cyanobenzyl)-1H-pyrazole-1-carboxylate (1.50 g, 5.30 mmol) in DCM (10 mL) was added TFA (5.0 mL) at room temperature. The reaction mixture was stirred at room temperature for 20 hours. After neutralization with saturated aq. Na₂CO₃ solution, the resulting mixture was extracted with DCM twice. The combined organic layers were dried over Na₂SO₄, filtered, and concentrated in vacuo. The residue was purified by prep-HPLC to afford 4-((1H-pyrazol-4-yl)methyl)benzonitrile (182 mg, 18%) as a white solid. ¹H-NMR (400 MHz, DMSO-d₆+D₂O): δ 7.73 (2H, d, J=8.4 Hz), 7.45 (2H, br), 7.41 (2H, d, J=8.4 Hz), 3.87 (2H, s).

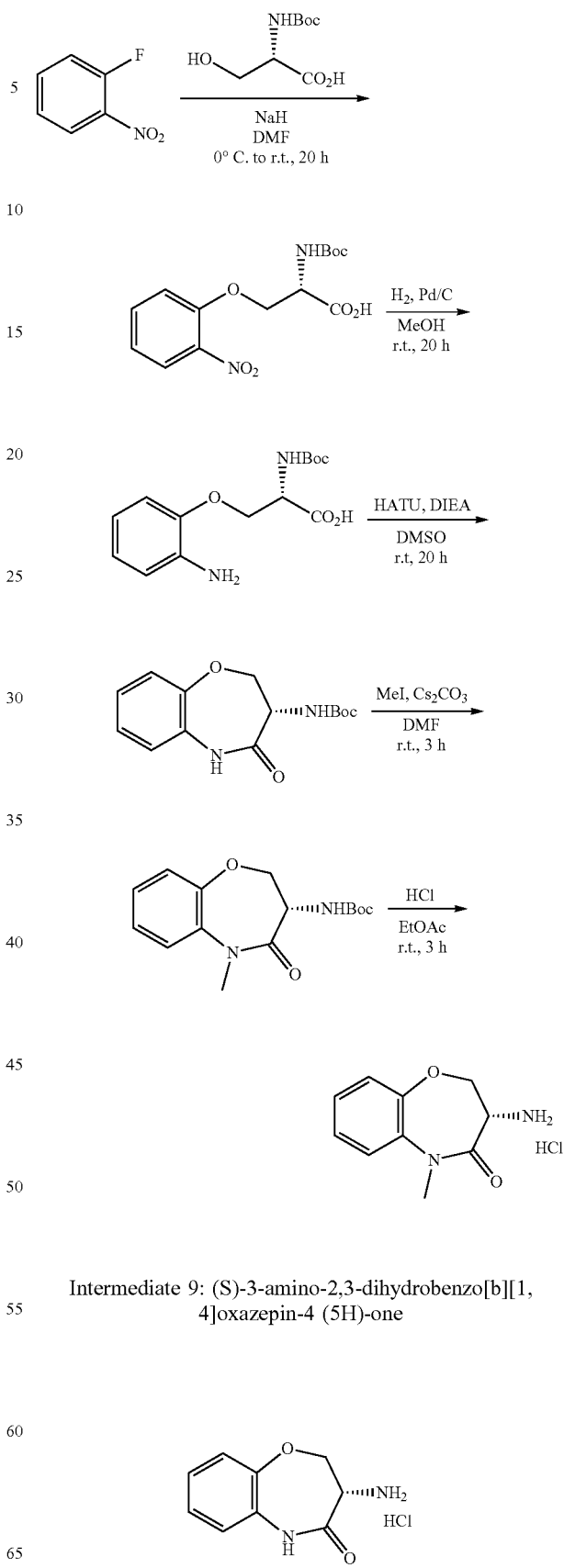

Intermediate 9: (S)-3-amino-2,3-dihydrobenzo[b][1,4]oxazepin-4(5H)-one

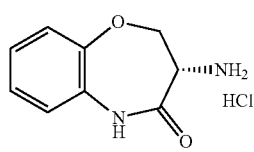 [SMILES: N[C@H]1COc2ccccc2NC1=O ; Cl]

Step A: (S)-2-((tert-butoxycarbonyl)amino)-3-(2-nitrophenoxy)propanoic acid

To a suspension of NaH (60 wt %, 4.90 g, 122 mmol) in dry DMF (150 mL) was slowly added a solution of N-Boc-L-serine (10.0 g, 48.7 mmol) in dry DMF at 0° C. under $N_2$ atmosphere. Once gas evolution had ceased, 1-fluoro-2-nitrobenzene (5.10 mL, 48.7 mmol) was added in one portion. The reaction mixture was stirred at room temperature for 20 hours and quenched with 0.5 M aq. HCl solution. The mixture was extracted with EtOAc three times. The combined organic layers were washed with brine and water, dried over $Na_2SO_4$, filtered and concentrated in vacuo. The residue was purified by column chromatography on $SiO_2$ (pet. Ether:EtOAc=5:1 to DCM:MeOH=20:1) to afford (S)-2-((tert-butoxycarbonyl)amino)-3-(2-nitrophenoxy)propanoic acid (10.0 g, 62%) as a brown solid. LC-MS: m/z=271.0 [M+H-tBu]$^+$.

Step B: (S)-3-(2-aminophenoxy)-2-((tert-butoxycarbonyl)amino)propanoic acid

A suspension of (S)-2-((tert-butoxycarbonyl)amino)-3-(2-nitrophenoxy)propanoic acid (9.00 g, 27.6 mmol) and Pd/C (10 wt %, 900 mg) in MeOH (50 mL) was stirred at room temperature for 20 hours under hydrogen atmosphere (1 atm). After filtered through a 0.45 um PTFE needle filter (MeOH flushed), the filtrate was concentrated in vacuo. The residue was purified by column chromatography on $SiO_2$ (pet. Ether:EtOAc=1:1) to afford (S)-3-(2-aminophenoxy)-2-((tert-butoxycarbonyl)amino)propanoic acid (4.00 g, 48%) as an off-white solid. LC-MS: m/z=297.1 [M+H]$^+$.

Step C: (S)-tert-butyl (4-oxo-2,3,4,5-tetrahydrobenzo[b][1,4]oxazepin-3-yl) carbamate To a solution of (S)-3-(2-aminophenoxy)-2-((tert-butoxycarbonyl)amino)propanoic acid (4.00 g, 13.5 mmol) in DMSO (20 mL) was added DIPEA (5.23 g, 40.5 mmol) followed by HATU (5.13 g, 13.5 mmol) at room temperature. The reaction mixture was stirred at room temperature for 30 min. After diluted with $H_2O$ (300 mL), the mixture was extracted with EtOAc (100 mL×3). The combined organic layers were dried over $Na_2SO_4$, filtered and concentrated in vacuo. The residue was purified by column chromatography on $SiO_2$ (pet. Ether:EtOAc=5:1) to afford (S)-tert-butyl (4-oxo-2,3,4,5-tetrahydrobenzo[b][1,4]oxazepin-3-yl) carbamate (2.00 g, 53%) as an off-white solid. $^1$H-NMR (400 MHz, DMSO-d$_6$): δ 9.91 (1H, s), 7.14-7.07 (5H, m), 4.33-4.27 (3H, m), 1.35 (9H, s).

Step D: (S)-3-amino-2,3-dihydrobenzo[b][1,4]oxazepin-4 (5H)-one

To a solution of (S)-tert-butyl (5-methyl-4-oxo-2,3,4,5-tetrahydrobenzo[b][1,4]oxazepin-3-yl) carbamate (2.00 g, 7.19 mmol) in EtOAc (5.0 mL) was added HCl (5 M in EtOAc, 10 mL) at room temperature. The reaction mixture was stirred at room temperature for 3 hours and concentrated in vacuo to afford (S)-3-amino-2,3-dihydrobenzo[b][1,4]oxazepin-4 (5H)-one (1.30 g, 84%) as a brown solid. $^1$H-NMR (400 MHz, DMSO-d$_6$): δ 10.50 (1H, s), 8.73 (3H, s), 7.14 (4H, s), 4.68-4.63 (1H, m), 4.45-4.40 (11H, m), 4.30-4.26 (1H, m).

Intermediate 10: (S)-3-amino-5-methyl-2,3-dihydrobenzo[b][1,4]oxazepin-4 (5H)-one hydrochloride

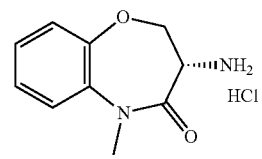

Step A: (S)-tert-butyl (5-methyl-4-oxo-2,3,4,5-tetrahydrobenzo[b][1,4]oxazepin-3-yl) carbamate To a solution of (S)-tert-butyl (4-oxo-2,3,4,5-tetrahydrobenzo[b][1,4]oxazepin-3-yl) carbamate (2.00 g, 7.19 mmol) in DMF (20 mL) was added $Cs_2CO_3$ (3.20 g, 9.90 mmol) followed by MeI (1.20 g, 8.50 mmol) dropwise at room temperature under $N_2$ atmosphere. The reaction mixture was stirred at room temperature for 3 hours. After quenched with cold $H_2O$ (100 mL), a precipitated solid was collected by filtration, and washed with water. The solid was purified by reversed column on C18 (MeCN:$H_2O$) to afford (S)-tert-butyl (5-methyl-4-oxo-2,3,4,5-tetrahydrobenzo[b][1,4]oxazepin-3-yl) carbamate (1.20 g, 57%) as a light yellow solid. $^1$H-NMR (400 MHz, DMSO-d$_6$): δ 7.47-7.45 (1H, m), 7.32-7.13 (4H, m), 4.37-4.27 (3H, m), 3.28 (3H, s), 1.34 (9H, s).

Step B: (S)-3-amino-5-methyl-2,3-dihydrobenzo[b][1,4]oxazepin-4 (5H)-one hydrochloride To a solution of (S)-tert-butyl (5-methyl-4-oxo-2,3,4,5-tetrahydrobenzo[b][1,4]oxazepin-3-yl) carbamate (1.20 g, 4.10 mmol) in EtOAc (5.0 mL) was added HCl (5 M in EtOAc, 10 mL, 50 mmol) at room temperature. The reaction mixture was stirred at room temperature for 3 hours and concentrated in vacuo to afford (S)-3-amino-5-methyl-2,3-dihydrobenzo[b][1,4]oxazepin-4 (5H)-one hydrochloride (820 mg, 87%) as a brown solid. $^1$H-NMR (400 MHz, MeOH-d$_4$): δ 8.74 (3H, s), 7.53-7.50 (1H, m), 7.36-7.25 (3H, m), 4.67-4.63 (11H, m), 4.48 (1H, t, J=11.2 Hz), 4.21-4.16 (11H, m), 3.34 (3H, s).

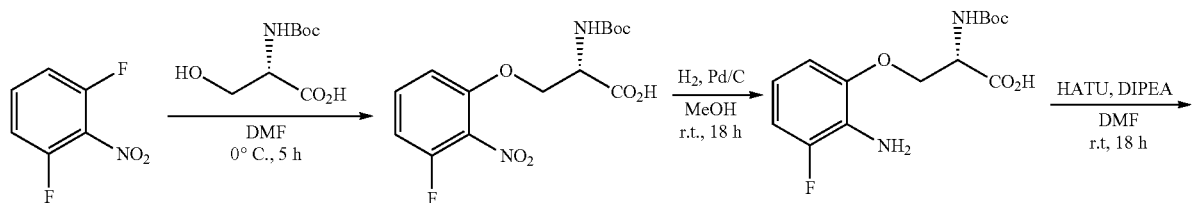

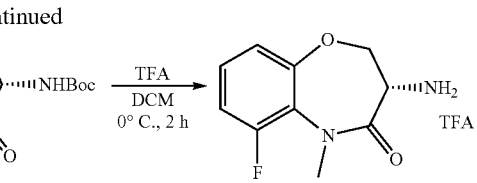

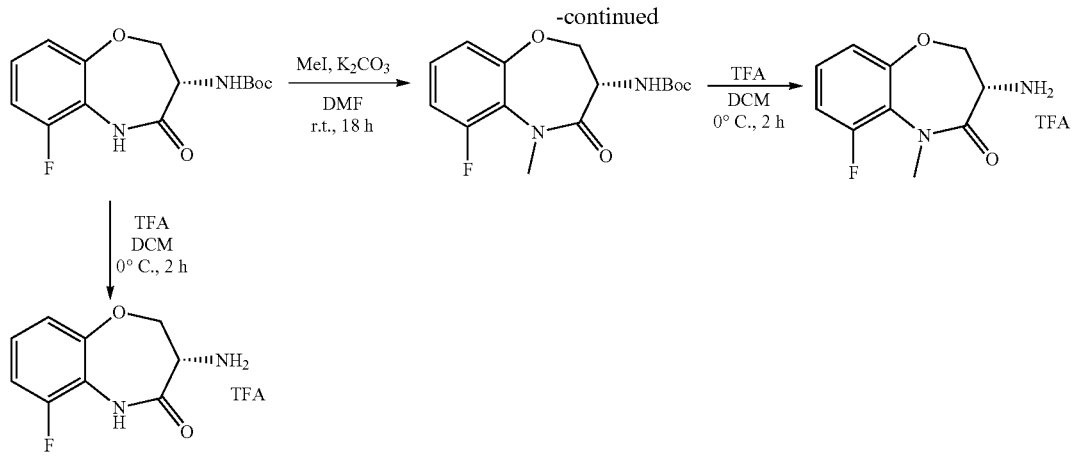

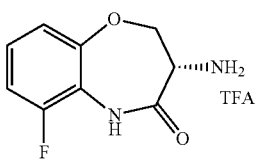 [SMILES: N[C@H]1COc2cccc(F)c2NC1=O ; "TFA"]

Intermediate 11: (S)-3-amino-6-fluoro-2,3-dihydrobenzo[b][1,4]oxazepin-4 (5H)-one 2,2,2-trifluoroacetate

Step A: (S)-2-(tert-butoxycarbonylamino)-3-(3-fluoro-2 nitrophenoxy)propanoic acid To a suspension of NaH (55 wt %, 823 mg, 18.9 mmol) in DMF (10 mL) was slowly added a solution of N-Boc-L-serine (1.55 g, 7.54 mmol) in DMF (5.0 mL) at 0° C. The mixture was stirred at 0° C. for 1 hour. After addition of a solution of 1,3-difluoro-2-nitrobenzene (1.00 g, 6.29 mmol) in DMF (5.0 mL) at 0° C., the reaction mixture was stirred at 0° C. for 4 hours. After quenched with 0.5 M aq. HCl at 0° C., the mixture was extracted with EtOAc, washed with water and brine, dried over $Na_2SO_4$, filtered and concentrated in vacuo. The residue was purified by column chromatography on $SiO_2$ (Hexanes:EtOAc=1:1 to 1:3) to afford (S)-2-(tert-butoxycarbonylamino)-3-(3-fluoro-2-nitrophenoxy)propanoic acid (1.20 g, 55%) as a yellow oil. $^1$H-NMR (400 MHz, $CDCl_3$): δ 9.38 (1H, brs), 7.40 (1H, q, J=7.6 Hz), 6.87-6.82 (2H, m), 5.54 (1H, d, J=7.6 Hz), 4.73 (1H, d, J=8.4 Hz), 4.58 (1H, dd, J=9.2, 2.4 Hz), 4.41 (1H, dd, J=9.0, 2.6 Hz), 1.45 (9H, s).

Step B: (S)-3-(2-amino-3-fluorophenoxy)-2-(tert-butoxycarbonylamino)propanoic acid A suspension of (S)-2-(tert-butoxycarbonylamino)-3-(3-fluoro-2-nitrophenoxy)propanoic acid (1.60 g, 4.65 mmol) and Pd/C (10 wt %, 495 mg, 0.465 mmol) in MeOH (15 mL) was stirred at room temperature for 18 hours under $H_2$ atmosphere (1 atm). After filtered through a Celite pad while washing with MeOH, the filtrate was concentrated in vacuo to afford (S)-3-(2-amino-3-fluorophenoxy)-2-(tert-butoxycarbonylamino)propanoic acid (1.46 g, 100%) as a yellow oil. $^1$H-NMR (400 MHz, DMSO-$d_6$): δ 7.54 (1H, d, J=8.4 Hz), 6.68-6.61 (2H, m), 6.48-6.42 (1H, m), 4.80 (2H, brs), 4.43-4.41 (1H, m), 4.32-4.28 (1H, m), 3.98 (1H, dd, J=9.2, 2.8 Hz), 1.36 (9H, s).

Step C: tert-butyl 6-fluoro-4-oxo-2,3,4,5-tetrahydrobenzo[b][1,4]oxazepin-3-ylcarbamate To a solution of (S)-3-(2-amino-3-fluorophenoxy)-2-(tert-butoxycarbonylamino)propanoic acid (1.40 g, 4.45 mmol) in DMF (15 mL) was added DIPEA (2.33 mL, 13.4 mmol) followed by HATU (2.54 g, 6.68 mmol) at 0° C. The reaction mixture was stirred at room temperature for 2 hours. After quenched with water, the mixture was extracted with EtOAc. The separated organic layer was washed with brine, dried over $Na_2SO_4$, filtered and concentrated in vacuo. The residue was purified by column chromatography on $SiO_2$ (Hexanes:EtOAc=4:1) to afford (S)-tert-butyl 6-fluoro-4-oxo-2,3,4,5-tetrahydrobenzo[b][1,4]oxazepin-3-ylcarbamate (328 mg, 25%) as a white solid. $^1$H-NMR (400 MHz, $CDCl_3$): δ 7.35 (1H, s), 7.08 (1H, q, J=8.4 Hz), 6.93-6.87 (2H, m), 5.52 (1H, s), 4.70-4.62 (2H, m), 4.23 (1H, t, J=10.0 Hz), 1.44 (9H, s).

Step D: (S)-3-amino-6-fluoro-2,3-dihydrobenzo[b][1,4]oxazepin-4 (5H)-one TFA To a solution of tert-butyl 6-fluoro-4-oxo-2,3,4,5-tetrahydrobenzo[b][1,4]oxazepin-3-ylcarbamate (178 mg, 0.601 mmol) in DCM (1.2 mL) was added TFA (0.93 mL, 12 mmol) at 0° C. The reaction mixture was stirred at 0° C. for 2 hours, and then concentrated in vacuo to afford (S)-3-amino-6-fluoro-2,3-dihydrobenzo[b][1,4]oxazepin-4 (5H)-one TFA as a brown oil. $^1$H-NMR (400 MHz, DMSO-$d_6$): δ 10.5 (1H, s), 8.44 (2H, s), 7.26-7.20 (1H, m), 7.17-7.13 (1H, m), 7.09-7.06 (1 H, m), 4.56-4.53 (1H, m), 4.49-4.46 (2H, m).

Intermediate 12: (S)-3-amino-6-fluoro-5-methyl-2,3-dihydrobenzo[b][1,4]oxazepin-4 (5H)-one TFA

Step A: Preparation of (S)-tert-butyl 6-fluoro-5-methyl-4-oxo-2,3,4,5 tetrahydrobenzo[b][1,4]oxazepin-3-ylcarbamate To a solution of (S)-tert-butyl 6-fluoro-4-oxo-2,3,4,5-tetrahydrobenzo[b][1,4]oxazepin-3-ylcarbamate (146 mg, to afford (S)-3-amino-butyl 6-fluoro-4-oxo-2,3,4,5-tetrahydrobenzo[b][1,4]oxazepin-3-ylcarbamate TFA (62 mg, 100%) as a brown oil. $^1$H-NMR (400 MHz, DMSO-$d_6$): δ 8.41 (2H, s), 7.40 (1H, q, J=7.5 Hz), 7.28 (1H, t, J=9.4 Hz), 7.14 (1H, d, J=8.4 Hz), 4.49-4.42 (3H, m), 3.25 (3H, d, J=2.0 Hz).

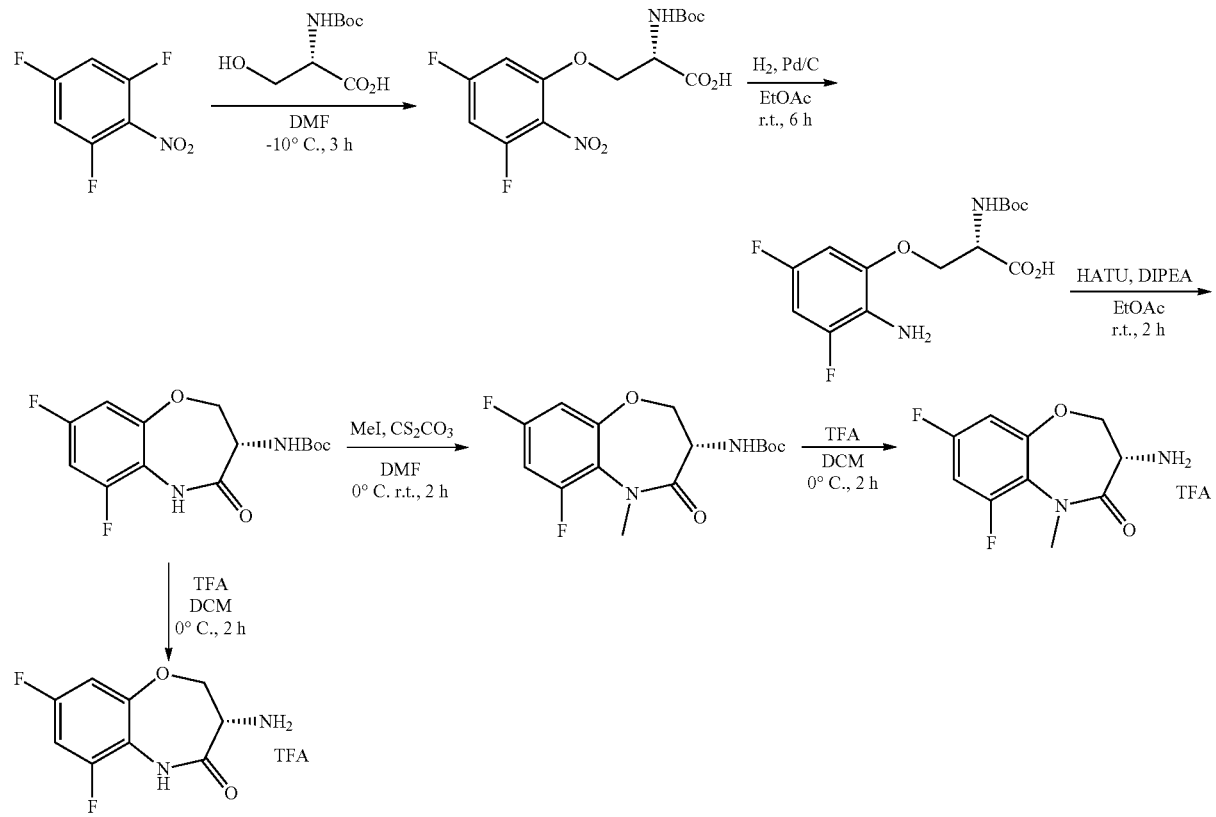

0.493 mmol) in DMF (4.9 mL) was added $K_2CO_3$ (82.0 mg, 0.591 mmol) and MeI (0.0370 mL, 0.591 mmol) at room temperature. The reaction mixture was stirred for 18 hours at room temperature. After diluted with water, the mixture was extracted with EtOAc. The separated organic layer was dried over $Na_2SO_4$, filtered and concentrated in vacuo. The residue was purified by column chromatography on $SiO_2$ (Hexanes:EtOAc=6:1) to afford (S)-tert-butyl 6-fluoro-5-methyl-4-oxo-2,3,4,5-tetrahydrobenzo[b][1,4]oxazepin-3-ylcarbamate (95 mg, 62%) as a colorless oil. $^1$H-NMR (400 MHz, CDCl$_3$): δ 7.21 (1H, q, J=7.6 Hz), 7.01-6.96 (2H, m), 5.51 (1H, d, J=6.8 Hz), 4.71-7.64 (1H, m), 4.55 (1H, t, J=8.6 Hz), 4.15 (1H, t, J=10.6 Hz), 3.35 (3H, d, J=2.4 Hz), 1.40 (9H, s).

Step B: (S)-3-amino-6-fluoro-5-methyl-2,3-dihydrobenzo[b][1,4]oxazepin-4 (5H)-one TFA To a solution of (S)-tert-butyl 6-fluoro-5-methyl-4-oxo-2,3,4,5-tetrahydrobenzo[b][1,4]oxazepin-3-ylcarbamate (63.0 mg, 0.203 mmol) in DCM (2.0 mL) was added TFA (0.31 mL, 4.1 mmol) at 0° C. The reaction mixture was stirred at 0° C. for 2 hours, and then concentrated in vacuo

Intermediate 13: 3-amino-6,8-difluoro-2,3-dihydrobenzo[b][1,4]oxazepin-4 (5H)-one TFA

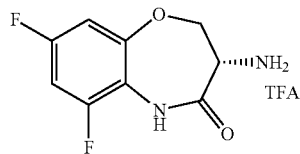 [SMILES: N[C@H]1COc2cc(F)cc(F)c2NC1=O ; "TFA"]

Step A: (S)-2-(tert-butoxycarbonylamino)-3-(3,5-difluoro-2-nitrophenoxy)propanoic acid To a suspension of NaH (55 wt %, 1.55 g, 35.6 mmol) in DMF (20 mL) was slowly added a solution of N-Boc-L-serine (3.48 g, 16.9 mmol) in DMF (5.0 mL) at −10° C. The mixture was stirred at −10° C. for 1 hour. After addition of a solution of 1,3,5-trifluoro-2-nitrobenzene (3.00 g, 16.9 mmol) in DMF (5.0 mL) at −10° C., the reaction mixture was stirred at −10° C. for 2 hours. After quenched with 0.5 M aq. HCl at −10° C., the mixture was extracted with EtOAc, washed with water and brine, dried over $Na_2SO_4$, filtered and concentrated in vacuo. The residue was purified by column chromatography on SiO$_2$ (Hexanes:EtOAc=5:1 to 1:1) to afford (S)-2-(tert-butoxycarbonylamino)-3-(3,5-difluoro-2-nitrophenoxy)propanoic acid (4.60 g, 75%) as a yellow oil. $^1$H-NMR (400 MHz, CDCl$_3$): δ 6.64-6.59 (2H, m), 5.49 (1H, d, J=7.2 Hz), 4.74 (1H, d, J=7.2 Hz), 4.55 (1H, d, J=6.8 Hz), 4.40 (1H, dd, J=9.6, 3.2 Hz), 1.46 (9H, s).

Step B: (S)-3-(2-amino-3,5-difluorophenoxy)-2-(tert-butoxycarbonylamino)propanoic acid A suspension of (S)-2-(tert-butoxycarbonylamino)-3-(3,5-difluoro-2-nitrophenoxy)propanoic acid (500 mg, 1.38 mmol) and Pd/C (5 wt %, 100 mg) in EtOAc (20 mL) was stirred at room temperature for 6 hours under H$_2$ atmosphere (1 atm). The reaction mixture was filtered through a Celite pad and washed with EtOAc (40 mL) to afford a solution of (S)-3-(2-amino-3,5-difluorophenoxy)-2-(tert-butoxycarbonylamino)propanoic acid (460 mg, 100%) in EtOAc (40 mL), which was used for next step without concentration. LC-MS: m/z=332.78 [M+H]$^+$.

Step C: tert-butyl 6,8-difluoro-4-oxo-2,3,4,5-tetrahydrobenzo[b][1,4]oxazepin-3-ylcarbamate To a solution of (S)-3-(2-amino-3,5-difluorophenoxy)-2-(tert-butoxycarbonylamino)propanoic acid (460 mg, 1.38 mmol) in EtOAc (40 mL) was added DIPEA (723 μL, 4.14 mmol) followed by HATU (787 mg, 2.07 mmol) at 0° C. The reaction mixture was stirred at room temperature for 2 hours. After concentration in vacuo, the residue was purified by column chromatography on SiO$_2$ (Hexanes:EtOAc=4:1 to 3:1) to afford tert-butyl 6,8-difluoro-4-oxo-2,3,4,5-tetrahydrobenzo[b][1,4]oxazepin-3-ylcarbamate (300 mg, 69%) as a white solid. $^1$H-NMR (400 MHz, CDCl$_3$): δ 7.22 (1H, brs), 6.71-6.66 (2H, m), 5.52 (1H, brs), 4.69-4.61 (2H, m), 4.25 (1H, t, J=9.6 Hz), 1.44 (9H, s).

Step D: 3-amino-6,8-difluoro-2,3-dihydrobenzo[b][1,4]oxazepin-4 (5H)-one TFA To a solution of tert-butyl 6,8-difluoro-4-oxo-2,3,4,5-tetrahydrobenzo[b][1,4]oxazepin-3-ylcarbamate (60 mg, 0.191 mmol) in DCM (5.0 mL) was added TFA (294 μL, 3.82 mmol) at 0° C. The mixture was stirred at room temperature for 2 hours and concentrated in vacuo to afford 3-amino-6,8-difluoro-2,3-dihydrobenzo[b][1,4]oxazepin-4 (5H)-one TFA (60 mg, 96%) as a yellow oil. LC-MS: m/z=214.93 [M+H]$^+$.

Intermediate 14: 3-amino-6,8-difluoro-5-methyl-2,3-dihydrobenzo[b][1,4]oxazepin-4 (5H)-one TFA

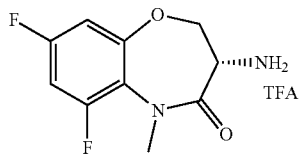 [SMILES: CN1C(=O)[C@@H](N)COc2cc(F)cc(F)c21 ; "TFA"]

Step A: (S)-tert-butyl 6,8-difluoro-5-methyl-4-oxo-2,3,4,5-tetrahydrobenzo[b][1,4]oxazepin-3-ylcarbamate A mixture of tert-butyl 6,8-difluoro-4-oxo-2,3,4,5-tetrahydrobenzo[b][1,4]oxazepin-3-ylcarbamate (150 mg, 0.477 mmol) and Cs$_2$CO$_3$ (187 mg, 0.573 mmol) in DMF (4.0 mL) was stirred at 0° C. for 5 minutes. After addition of a solution of MeI (36.0 μL, 0.573 mmol) in DMF (1.0 mL), the reaction mixture was stirred at 0° C. for 1 hour and then at room temperature for further 1 hour. After quenched with water, the mixture was extracted with EtOAc, dried over Na$_2$SO$_4$, filtered and concentrated in vacuo. The residue was purified by column chromatography on SiO$_2$ (Hexanes:EtOAc=2:1) to afford (S)-tert-butyl 6,8-difluoro-5-methyl-4-oxo-2,3,4,5-tetrahydrobenzo[b][1,4]oxazepin-3-ylcarbamate (120 mg, 77%) as a colorless oil. $^1$H-NMR (400 MHz, CDCl$_3$): δ 6.80-6.73 (2H, m), 5.51 (1H, d, J=6.0 Hz), 4.70-4.64 (1H, m), 4.54 (1H, dd, J=9.2, 6.8 Hz), 4.17 (1H, t, J=10.4 Hz), 3.32 (3H, d, J=2.4 Hz), 1.41 (9H, s).

Step B: 3-amino-6,8-difluoro-5-methyl-2,3-dihydrobenzo[b][1,4]oxazepin-4 (5H)-one TFA To a solution of tert-butyl 6,8-difluoro-5-methyl-4-oxo-2,3,4,5-tetrahydrobenzo[b][1,4]oxazepin-3-ylcarbamate (80 mg, 0.244 mmol) in DCM (5.0 mL) was added TFA (375 μL, 4.87 mmol) at 0° C. The reaction mixture was stirred at room temperature for 2 hours and concentrated in vacuo to afford 3-amino-6,8-difluoro-5-methyl-2,3-dihydrobenzo[b][1,4]oxazepin-4 (5H)-one TFA (83 mg, 100%) as a yellow oil. $^1$H-NMR (400 MHz, CDCl$_3$): δ 6.80-6.73 (2H, m), 5.51 (1H, d, J=6.0 Hz), 4.70-4.64 (1H, m), 4.54 (1H, dd, J=9.2, 6.8 Hz), 4.17 (1H, t, J=10.4 Hz), 3.32 (3H, d, J=2.4 Hz), 1.41 (9H, s).

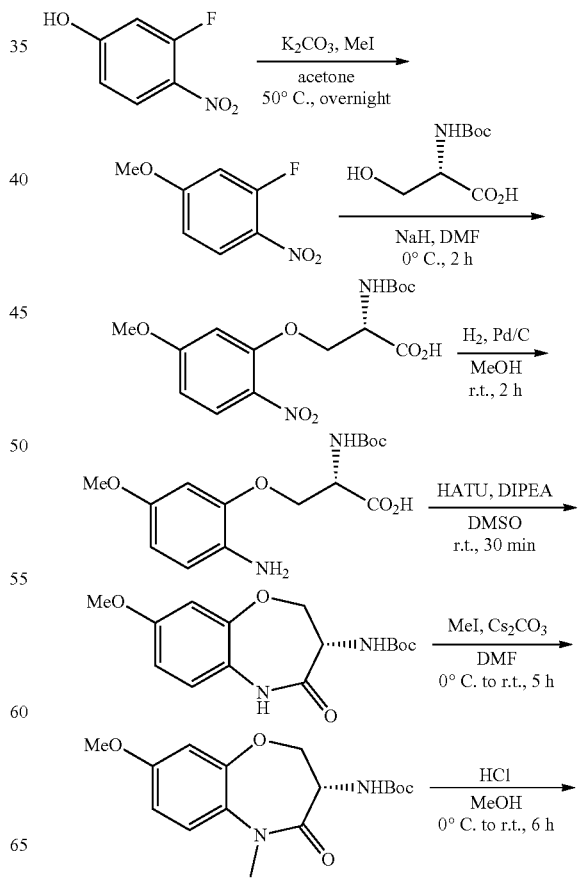

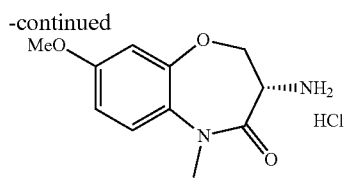

Intermediate 15: (S)-3-amino-8-methoxy-5-methyl-2,3-dihydrobenzo[b][1,4]oxazepin-4 (5H)-one hydrochloride

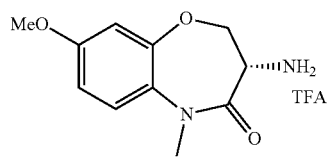 [SMILES: COc1ccc2c(c1)OC[C@H](N)C(=O)N2C ; "TFA"]

Step A: 2-fluoro-4-methoxy-1-nitrobenzene

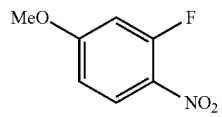 [SMILES: COc1ccc([N+](=O)[O-])c(F)c1]

To a solution of 3-fluoro-4-nitrophenol (1.00 g, 6.37 mmol) in acetone (20 mL) was added K$_2$CO$_3$ (4.40 g, 31.8 mmol) followed by MeI (0.796 mL, 12.7 mmol). The reaction mixture was stirred at 50° C. overnight. After dilution with DCM, the mixture was filtered through a Celite pad and washed with DCM. The filtrate was concentrated in vacuo. The residue was dissolved in EtOAc, washed with 1 N aq. NaOH, dried over Na$_2$SO$_4$, filtered and concentrated in vacuo to afford 2-fluoro-4-methoxy-1-nitrobenzene (900 mg, 83%) as a colorless oil. $^1$H-NMR (400 MHz, CDCl$_3$): δ 8.10 (1H, t, J=8.8 Hz), 6.79-6.72 (2H, m), 3.91 (3H, s).

Step B: 2. Preparation of (S)-2-(tert-butoxycarbonylamino)-3-(5-methoxy-2-nitrophenoxy) propanoic acid To a suspension of NaH (55 wt %, 213 mg, 4.87 mmol) in dry DMF was slowly added a solution of N-Boc-L-serine (500 mg, 2.44 mmol) in dry DMF (10 mL) at 0° C. The mixture was stirred at room temperature for 30 minutes and cooled to 0° C. After addition of a solution of 2-fluoro-4-methoxy-1-nitrobenzene (417 mg, 2.44 mmol) in dry DMF (5.0 mL) at 0° C., the reaction mixture was stirred at 0° C. for 2 hours. After quenched with 0.5 M aq. HCl, the mixture was extracted with EtOAc, washed with brine, dried over Na$_2$SO$_4$, filtered, and concentrated in vacuo. The residue was purified by column chromatography SiO$_2$ (Hexanes:EtOAc=4:1 to 1:1) to afford (S)-2-(tert-butoxycarbonylamino)-3-(5-methoxy-2-nitrophenoxy)propanoic acid (400 mg, 46%) as a yellow oil. LC-MS: m/z=257.05 [M+H]$^+$.

Step C: (S)-3-(2-amino-5-methoxyphenoxy)-2-(tert-butoxycarbonylamino)propanoic acid A suspension of (S)-2-(tert-butoxycarbonylamino)-3-(5-methoxy-2-nitrophenoxy)propanoic acid (400 mg, 1.12 mmol) and Pd/C (5 wt %, 50 mg) in MeOH (10 mL) was stirred at room temperature for 2 hours under H$_2$ atmosphere (1 atm). After filtration through a Celite pad while washing with MeOH, the filtrate was concentrated in vacuo to afford (S)-3-(2-amino-5-methoxyphenoxy)-2-(tert-butoxycarbonylamino)propanoic acid (200 mg, 55%) as a black solid. LC-MS: m/z=326.92 [M+H]$^+$.

Step D: (S)-tert-butyl 8-methoxy-4-oxo-2,3,4,5-tetrahydrobenzo[b][1,4]oxazepin-3-ylcarbamate To solution of (S)-3-(2-amino-5-methoxyphenoxy)-2-(tert-butoxycarbonylamino)propanoic acid (200 mg, 0.613 mmol) in DMSO (3.0 mL) was added DIPEA (321 μL, 1.84 mmol) followed by HATU (233 mg, 0.613 mmol) at 0° C. The reaction mixture was stirred at room temperature for 30 minutes. After quenched with ice-water, the mixture was extracted with EtOAc, dried over Na$_2$SO$_4$, filtered and concentrated in vacuo. The residue was purified by column chromatography SiO$_2$ (Hexanes:EtOAc=2:1) to afford (S)-tert-butyl 8-methoxy-4-oxo-2,3,4,5-tetrahydrobenzo[b][1,4]oxazepin-3-ylcarbamate (100 mg, 53%) as a white solid. $^1$H-NMR (400 MHz, CDCl$_3$): δ 7.43 (1H, brs), 7.07 (1H, d, J=8.8 Hz), 6.70 (1H, dd, J=8.8, 2.8 Hz), 5.45 (1H, d, J=6.8 Hz), 4.73-4.66 (1H, m), 4.61 (1H, t, J=9.6 Hz), 4.16 (1H, t, J=10.0 Hz), 3.78 (3H, s), 1.42 (9H, s).

Step E: (S)-tert-butyl 8-methoxy-5-methyl-4-oxo-2,3,4,5-tetrahydrobenzo[b][1,4]oxazepin-3-ylcarbamate To a solution of (S)-tert-butyl 8-methoxy-4-oxo-2,3,4,5-tetrahydrobenzo[b][1,4]oxazepin-3-ylcarbamate (100 mg, 0.324 mmol) in DMF (5.0 mL) was added Cs$_2$CO$_3$ (106 mg, 0.324 mmol) followed by a solution of MeI (20.3 μL, 0.324 mmol) in DMF (1.0 mL) at 0° C. The reaction mixture was stirred for 4 hours at 0° C. and then at room temperature for 1 hour. After quenched with ice-water, the mixture was extracted with EtOAc, dried over Na$_2$SO$_4$, filleted, and concentrated in vacuo. The residue was purified by column chromatography on SiO$_2$ (Hexanes:EtOAc=3:1) to afford (S)-tert-butyl 8-methoxy-5-methyl-4-oxo-2,3,4,5-tetrahydrobenzo[b][1,4]oxazepin-3-ylcarbamate (100 mg, 96%) as a colorless oil. $^1$H-NMR (400 MHz, CDCl$_3$): δ 7.09 (1H, d, J=8.4 Hz), 6.74 (1H, d, J=8.4 Hz), 6.69 (1H, s), 5.50 (1H, d, J=6.0 Hz), 4.69-4.63 (1H, m), 4.57 (1H, t, J=9.2 Hz), 4.15 (1H, t, J=10.0 Hz), 3.80 (3H, s), 3.36 (3H, s), 1.40 (9H, s).

Step F: (S)-3-amino-8-methoxy-5-methyl-2,3-dihydrobenzo[b][1,4]oxazepin-4 (5H)-one hydrochloride To a solution of (S)-tert-butyl 8-methoxy-5-methyl-4-oxo-2,3,4,5-tetrahydrobenzo[b][1,4]oxazepin-3-ylcarbamate (50.0 mg, 0.155 mmol) in MeOH (3.0 mL) was added HCl (2 M in diethyl ether, 1.55 mL, 3.10 mmol) at 0° C. The reaction mixture was stirred at room temperature for 6 hours and then concentrated in vacuo to afford (S)-3-amino-8-methoxy-5-methyl-2,3-dihydrobenzo[b][1,4]oxazepin-4 (5H)-one hydrochloride (40 mg, 100%) as a white solid. LC-MS: m/z=223.05 [M+H]$^+$.

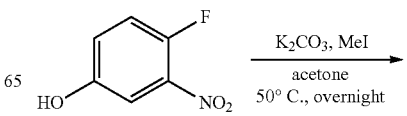

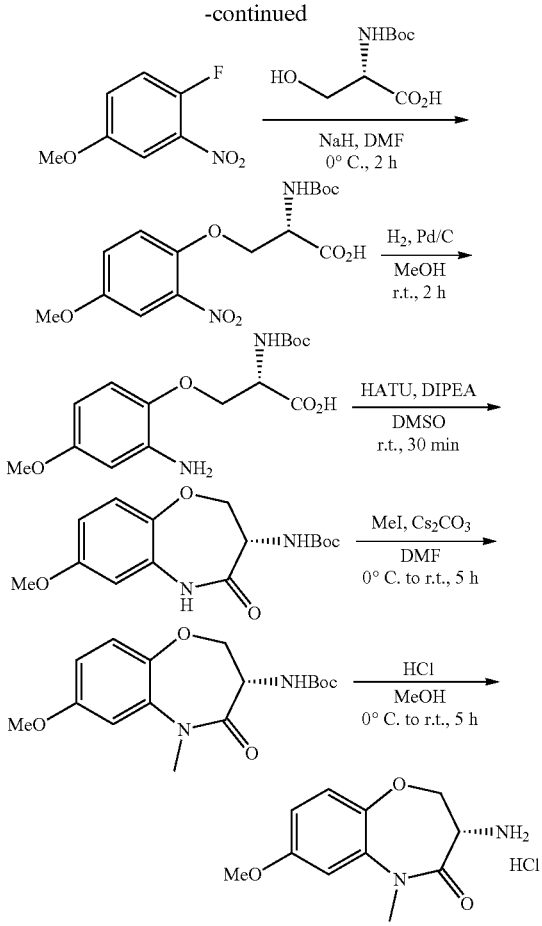

Intermediate 16: (S)-3-amino-7-methoxy-5-methyl-2,3-dihydrobenzo[b][1,4]oxazepin-4 (5H)-one hydrochloride

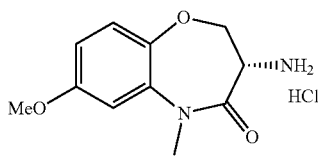 [SMILES: COc1ccc2c(c1)N(C)C(=O)[C@@H](N)CO2 ; Cl]

Step A: 1-fluoro-4-methoxy-2-nitrobenzene

To a solution of 4-fluoro-3-nitrophenol (1.00 g, 6.37 mmol) in acetone (30 mL) was added $K_2CO_3$ (4.40 g, 31.8 mmol) followed by MeI (0.796 mL, 12.7 mmol) at room temperature. The reaction mixture was stirred at 50° C. overnight. After dilution with DCM, the mixture was filtered through a Celite pad and washed with DCM. The filtrate was concentrated in vacuo. The residue was diluted with EtOAc, washed with 1 N aq. NaOH, dried over $Na_2SO_4$, filtered and concentrated in vacuo to afford 1-fluoro-4-methoxy-2-nitrobenzene (1.00 g, 92%) as a colorless oil. $^1$H-NMR (400 MHz, CDCl$_3$): δ 7.54-7.52 (11H, m) 7.23-7.14 (2H, m), 3.86 (3H, s).

Step B: 2. (S)-2-(tert-butoxycarbonylamino)-3-(4-methoxy-2-nitrophenoxy)propanoic acid To a suspension of NaH (55 wt %, 460 mg, 10.54 mmol) in dry DMF (20 mL) was slowly added a solution of N-Boc-L-serine (1.00 g, 4.87 mmol) in dry DMF (5.0 mL) at 0° C. The mixture was stirred at room temperature for 30 minutes and cooled to 0° C. After addition of a solution of 1-fluoro-4-methoxy-2-nitrobenzene (900 mg, 5.26 mmol) in dry DMF (5.0 mL) at 0° C., the reaction mixture was stirred at 0° C. for 2 hours. After quenched with 0.5 M aq. HCl, the mixture was extracted with EtOAc, washed with brine, dried over $Na_2SO_4$, filtered, and concentrated in vacuo. The residue was purified by column chromatography on $SiO_2$ (Hexanes:EtOAc=4:1 to 1:1) to afford (S)-2-(tert-butoxycarbonylamino)-3-(4-methoxy-2-nitrophenoxy)propanoic acid (900 mg, 48%) as a yellow oil. LC-MS: m/z=257.01 $[M+H]^+$.

Step C: (S)-3-(2-amino-4-methoxyphenoxy)-2-(tert-butoxycarbonylamino)propanoic acid A suspension of (S)-2-(tert-butoxycarbonylamino)-3-(4-methoxy-2-nitrophenoxy)propanoic acid (350 mg, 0.982 mmol) and Pd/C (5 wt %, 50 mg) in MeOH (10 mL) was stirred at room temperature for 2 hours under $H_2$ atmosphere (1 atm). After filtration through a Celite pad while washing with MeOH, the filtrate was concentrated in vacuo to afford (S)-3-(2-amino-4-methoxyphenoxy)-2-(tert-butoxycarbonylamino)propanoic acid (200 mg, 62%) as a black solid. LC-MS: m/z=326.89 $[M+H]^+$.

Step D: (S)-tert-butyl 7-methoxy-4-oxo-2,3,4,5-tetrahydrobenzo[b][1,4]oxazepin-3-ylcarbamate To solution of (S)-3-(2-amino-4-methoxyphenoxy)-2-(tert-butoxycarbonylamino)propanoic acid (320 mg, 0.981 mmol) in DMSO (3.0 mL) was added DIPEA (514 µL, 2.94 mmol) followed by HATU (373 mg, 0.981 mmol) at 0° C. The reaction mixture was stirred at room temperature for 30 minutes. After quenched with ice-water, the mixture was extracted with EtOAc, dried over $Na_2SO_4$, filtered and concentrated in vacuo. The residue was purified by column chromatography on $SiO_2$ (Hexanes:EtOAc=2:1) to afford (S)-tert-butyl 7-methoxy-4-oxo-2,3,4,5-tetrahydrobenzo[b][1,4]oxazepin-3-ylcarbamate (200 mg, 66%) as a white solid. $^1$H-NMR (400 MHz, CDCl$_3$): δ 7.17 (1H, brs), 6.90 (1H, d, J=8.8 Hz), 6.68-6.64 (2H, m), 5.48 (1H, brs), 4.69-4.61 (2H, m), 4.21 (1H, t, J=9.6 Hz), 3.79 (3H, s), 1.42 (9H, s).

Step E: (S)-tert-butyl 7-methoxy-5-methyl-4-oxo-2,3,4,5-tetrahydrobenzo[b][1,4]oxazepin-3-ylcarbamate To a solution of (S)-tert-butyl 7-methoxy-4-oxo-2,3,4,5-tetrahydrobenzo[b][1,4]oxazepin-3-ylcarbamate (200 mg, 0.649 mmol) in DMF (5.0 mL) was added $Cs_2CO_3$ (254 mg, 0.778 mmol) followed by a solution of MeI (48.7 µL, 0.778 mmol) in DMF (1.0 mL) at 0° C. The reaction mixture was stirred for 4 hours at 0° C. and then at room temperature for further 1 hour. After quenched with ice-water, the mixture was extracted with EtOAc, dried over $Na_2SO_4$, filtered, and concentrated in vacuo. The residue was purified by column chromatography on $SiO_2$ (Hexanes:EtOAc=3:1) to afford (S)-tert-butyl 7-methoxy-5-methyl-4-oxo-2,3,4,5-tetrahydrobenzo[b][1,4]oxazepin-3-ylcarbamate (150 mg, 72%) as a colorless oil. LC-MS: m/z=[M+H]⁺.

Step F: (S)-3-amino-7-methoxy-5-methyl-2,3-dihydrobenzo[b][1,4]oxazepin-4 (5H)-one hydrochloride To a solution of (S)-tert-butyl 7-methoxy-5-methyl-4-oxo-2,3,4,5-tetrahydrobenzo [b][1,4]oxazepin-3-ylcarbamate (40 mg, 0.124 mmol) in MeOH (3.0 mL) was added HCl (2 M in Et$_2$O, 1.24 mL, 2.48 mmol) at 0° C. The reaction mixture was stirred at room temperature for 5 hours and concentrated in vacuo to afford (S)-3-amino-7-methoxy-5-methyl-2,3-dihydrobenzo[b][1,4]oxazepin-4 (5H)-one hydrochloride (32 mg, 100%) as a white solid. LC-MS: m/z=223.05 [M+H]⁺.

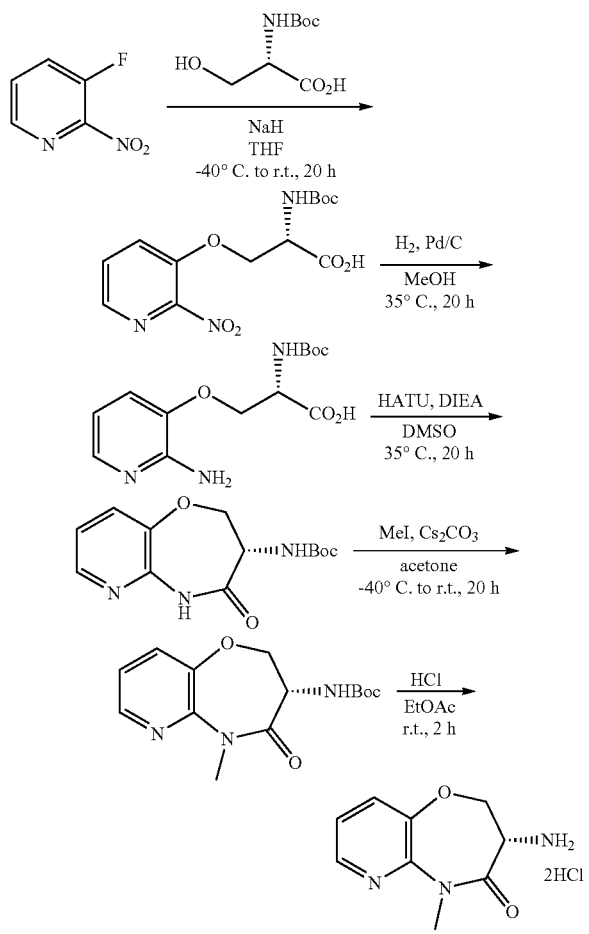

Intermediate 17: (S)-3-amino-5-methyl-2,3-dihydropyrido[3,2-b][1,4]oxazepin-4 (5H)-one dihydrochloride

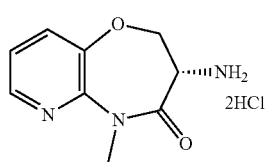

Step A: (S)-2-((tert-butoxycarbonyl)amino)-3-((2-nitropyridin-3-yl)oxy)propanoic acid To a solution of N-Boc-L-serine (22.8 g, 111 mmol) in dry THF (200 mL) was slowly added NaH (60 wt %, 8.31 g, 207 mmol) in portions at −40° C. The mixture was stirred at 0° C. for 2 hours and then cooled to −40° C. After slow addition of a solution of 3-fluoro-2-nitropyridine (15.0 g, 101 mmol) in dry THF (100 mL) at −40° C., the reaction mixture was stirred at room temperature for 20 hours. After quenched with water, the mixture was acidified until pH 6 with 1 M aq. HCl solution and then extracted with EtOAc (300 mL×3). The combined organic layers were washed with brine and water, dried over Na$_2$SO$_4$, filtered and concentrated in vacuo. The residue was purified on SiO$_2$ (DCM:MeOH=20:1) to afford (S)-2-((tert-butoxycarbonyl)amino)-3-((2-nitropyridin-3-yl)oxy)propanoic acid (21.1 g, 61%) as a yellow semi-solid. ¹H-NMR (400 MHz, DMSO-d$_6$): δ 8.12 (1H, d, J=4.0 Hz), 7.98 (1H, d, J=8.0 Hz), 7.76 (1H, dd, J=8.8, 4.8 Hz), 7.17 (1H, d, J=7.6 Hz), 4.50-4.48 (1H, m), 4.43-4.39 (2H, m), 1.37 (9H, s).

Step B: (S)-3-((2-aminopyridin-3-yl)oxy)-2-((tert-butoxycarbonyl)amino)propanoic acid A suspension of (S)-2-((tert-butoxycarbonyl)amino)-3-((2-nitropyridin-3-yl)oxy)propanoic acid (21.1 g, 64.5 mmol) and Pd/C (10 wt %, 2.11 g) in MeOH (100 mL) was stirred at 35° C. for 20 hours under hydrogen atmosphere (1 atm). After filtration through a 0.45 um PTFE needle filter washing with DCM/MeOH+AcOH (v/v=20:1), the filtrate was concentrated in vacuo to afford (S)-3-((2-aminopyridin-3-yl)oxy)-2-((tert-butoxycarbonyl)amino)propanoic acid (19.6 g, >99%) as a grey semi-solid. ¹H-NMR (400 MHz, DMSO-d$_6$): δ 7.57 (1H, d, J=9.2 Hz), 7.49 (1H, d, J=4.4 Hz), 6.98 (1H, d, J=7.6 Hz), 6.46 (1H, dd, J=7.6, 5.2 Hz), 5.89 (2H, br), 4.48-4.45 (1H, m), 4.34 (1H, dd, J=9.2, 4.4 Hz), 3.98 (1H, dd, J=9.6, 3.2 Hz), 1.40 (9H, s).

Step C: (S)-tert-butyl (4-oxo-2,3,4,5-tetrahydropyrido[3,2-b][1,4]oxazepin-3-yl)carbamate To a solution of (S)-3-((2-aminopyridin-3-yl)oxy)-2-((tert-butoxycarbonyl)amino)propanoic acid (9.00 g, 25.1 mmol) in DMSO (20 mL) was added DIPEA (9.71 g, 75.3 mmol) followed by HATU (9.54 g, 25.1 mmol) at room temperature. The reaction mixture was stirred at 35° C. for 20 hours. After dilution with H$_2$O (100 mL), the mixture was extracted with EtOAc (100 mL×3). The combined organic layers were dried over Na$_2$SO$_4$, filtered and concentrated in vacuo. The residue was purified by column chromatography on SiO$_2$ (pet. ether:EtOAc=5:1) to afford (S)-tert-butyl (4-oxo-2,3,4,5-tetrahydropyrido[3,2-b][1,4]oxazepin-3-yl) carbamate (1.80 g, 25%) as a white solid. ¹H-NMR (400 MHz, DMSO-d$_6$): δ 10.37 (1H, s), 8.14 (1H, d, J=4.4 Hz), 7.54 (1H, d, J=7.6 Hz), 7.17-7.14 (2H, m), 4.39-4.29 (3H, m), 1.37 (9H, s).

Step D: (S)-tert-butyl (5-methyl-4-oxo-2,3,4,5-tetrahydropyrido[3,2-b][1,4]oxazepin-3-yl)carbamate To a solution of (S)-tert-butyl (4-oxo-2,3,4,5-tetrahydropyrido[3,2-b][1,4]oxazepin-3-yl)carbamate (1.80 g, 6.45 mmol) in acetone (100 mL) was added Cs$_2$CO$_3$ (2.30 g, 7.09 mmol) followed by a solution of MeI (1.11 g, 7.83 mmol) in acetone (8.0 mL) dropwise at −40° C. The reaction mixture was stirred at −40° C. for 1 hour and then at room temperature for 20 hours. After quenched with H₂O, the mixture was extracted with EtOAc (30 mL×3). The combined organic layers were dried over Na₂SO₄, filtered and concentrated in vacuo. The residue was purified by column chromatography on SiO₂ (pet. ether:EtOAc=5:1) to afford (S)-tert-butyl (5-methyl-4-oxo-2,3,4,5-tetrahydropyrido[3,2-b][1,4]oxazepin-3-yl)carbamate (705 mg, 37%) as a white solid. ¹H-NMR (400 MHz, DMSO-d₆): δ 8.34 (1H, dd, J=4.8, 1.2 Hz), 7.65 (1H, dd, J=8.0, 1.6 Hz), 7.31-7.25 (2H, m), 4.42-4.35 (3H, m), 3.32 (3H, s), 1.35 (9H, s).

Step E: (S)-3-amino-5-methyl-2,3-dihydropyrido[3,2-b][1,4]oxazepin-4 (5H)-one dihydrochloride To a solution of (S)-tert-butyl (5-methyl-4-oxo-2,3,4,5-tetrahydropyrido[3,2-b][1,4]oxazepin-3-yl)carbamate (700 mg, 2.38 mmol) in EtOAc (5.0 mL) was added HCl (6 M in EtOAc, 10 mL, 60 mmol) at room temperature. The reaction mixture was stirred at room temperature for 2 hours and concentrated in vacuo to afford (S)-3-amino-5-methyl-2,3-dihydropyrido[3,2-b][1,4]oxazepin-4 (5H)-one dihydrochloride (450 mg, 82%) as a white solid. ¹H-NMR (400 MHz, DMSO-d₆+D₂O): δ 8.39 (1H, d, J=4.4 Hz), 7.76 (1H, d, J=8.0 Hz), 7.39-7.37 (1H, m), 4.70 (1H, t, J=8.0 Hz), 4.55 (1H, t, J=10.0 Hz), 4.43-4.39 (1H, m), 3.40 (3H, s).

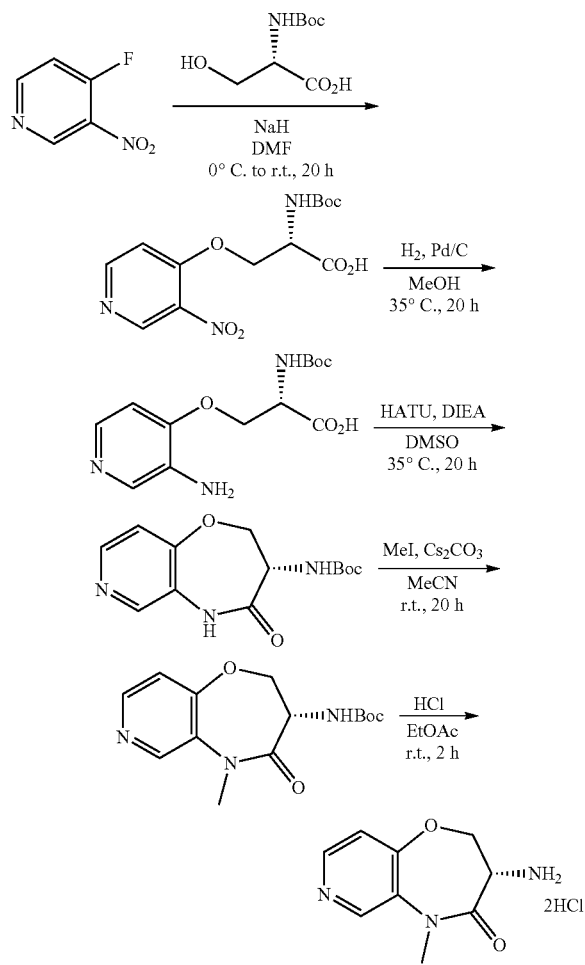

Intermediate 18: (S)-3-amino-5-methyl-2,3-dihydropyrido[4,3-b][1,4]oxazepin-4 (5H)-one dihydrochloride

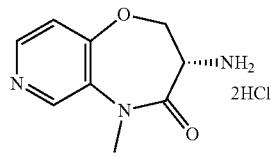

Step A: (S)-2-((tert-butoxycarbonyl)amino)-3-((3-nitropyridin-4-yl)oxy)propanoic acid To a suspension of NaH (60 wt %, 15.7 g, 394 mmol) in dry DMF (200 mL) was slowly added a solution of N-Boc-L-serine (32.2 g, 157 mmol) in dry DMF (50 mL) at 0° C. The mixture was stirred at 0° C. for 1 hour. After slow addition of a solution of 1-fluoro-2-nitrobenzene (25.0 g, 157 mmol) in DMF (50 mL), the reaction mixture was stirred at room temperature for 20 hours. After quenched with water, the mixture was neutralized with 1 M aq. HCl solution and then extracted with EtOAc (200 mL×3). The combined organic layers were washed with brine and water, dried over Na₂SO₄, filtered and concentrated in vacuo to afford (S)-2-((tert-butoxycarbonyl)amino)-3-((3-nitropyridin-4-yl)oxy)propanoic acid (44 g, 76%) as a brown oil. ¹H-NMR (400 MHz, DMSO-d₆): δ 13.0 (1H, brs), 8.97 (1H, s), 8.66 (1H, d, J=6.0 Hz), 7.46 (1H, d, J=6.0 Hz), 7.19 (11H, d, J=3.6 Hz), 4.54-4.45 (3H, m), 1.38 (9H, s).

Step B: (S)-3-((3-aminopyridin-4-yl)oxy)-2-((tert-butoxycarbonyl)amino)propanoic acid A suspension of (S)-2-((tert-butoxycarbonyl)amino)-3-((3-nitropyridin-4-yl)oxy)propanoic acid (40.0 g, 122 mmol) and Pd/C (10 wt %, 4.00 g) in MeOH (50 mL) was stirred at 35° C. for 20 hours under hydrogen atmosphere (1 atm). After filtration through a 0.45 um PTFE needle filter washing with MeOH, the filtrate was concentrated in vacuo to afford (S)-3-((3-aminopyridin-4-yl)oxy)-2-((tert-butoxycarbonyl)amino)propanoic acid (35.5 g, 98%) as a brown solid. ¹H-NMR (400 MHz, DMSO-d₆): δ 7.83 (1H, s), 7.69 (1H, d, J=5.2 Hz), 7.44 (1H, d, J=8.8 Hz), 6.79 (11H, d, J=5.2 Hz), 4.47-4.43 (1H, m), 4.39 (1H, dd, J=9.6, 4.4 Hz), 4.07 (1 H, dd, J=9.6, 3.2 Hz), 1.40 (9H, s).

Step C: (S)-tert-butyl (4-oxo-2,3,4,5-tetrahydropyrido[4,3-b][1,4]oxazepin-3-yl)carbamate To a solution of (S)-3-((3-aminopyridin-4-yl)oxy)-2-((tert-butoxycarbonyl)amino)propanoic acid (35.0 g, 117 mmol) in DMSO (100 mL) was added DIPEA (45.9 g, 353 mmol) followed by HATU (44.7 g, 117 mmol) at room temperature. The reaction mixture was stirred at 35° C. for 20 hours. After diluted with H₂O (300 mL), the mixture was extracted with EtOAc (300 mL×3). The combined organic layers were dried over Na₂SO₄, filtered and concentrated in vacuo. The residue was purified by column chromatography on SiO₂ (pet. ether:EtOAc=1:1) to afford (S)-tert-butyl (4-oxo-2,3,4,5-tetrahydropyrido[4,3-b][1,4]oxazepin-3-yl)carbamate (2.50 g, 7%) as a white solid. ¹H-NMR (400 MHz, DMSO-d₆): δ 10.25 (1H, s), 8.32 (1H, s), 8.12 (1H, d, J=5.2 Hz), 7.12 (1H, d, J=6.8 Hz), 7.03 (1H, d, J=5.6 Hz), 4.38-4.33 (3H, m), 1.39 (9H, s).

Step D: (S)-tert-butyl (5-methyl-4-oxo-2,3,4,5-tetra-hydropyrido[4,3-b][1,4]oxazepin-3-yl)carbamate To a solution of (S)-tert-butyl (4-oxo-2,3,4,5-tetrahydro-pyrido[4,3-b][1,4]oxazepin-3-yl)carbamate (2.00 g, 7.16 mmol) in MeCN (10 mL) was added Cs$_2$CO$_3$ (4.66 g, 14.3 mmol) followed by MeI (1.11 g, 7.83 mmol) in MeCN (10 mL) dropwise at room temperature. The reaction mixture was stirred at room temperature for 20 hours. After quenched with water, the mixture was extracted with EtOAc (20 mL×3). The combined organic layers were dried over Na$_2$SO$_4$, filtered and concentrated in vacuo. The residue was purified by column chromatography on SiO$_2$ (pet. ether: EtOAc=1:1) to afford (S)-tert-butyl (5-methyl-4-oxo-2,3,4,5-tetrahydropyrido[4,3-b][1,4]oxazepin-3-yl)carbamate (600 mg, 28%) as a white solid. $^1$H-NMR (400 MHz, DMSO-d$_6$): δ 8.71 (1H, s), 8.41 (1H, d, J=4.4 Hz), 7.21 (1H, d, J=5.2 Hz), 7.18 (1H, d, J=5.6 Hz), 4.42-4.38 (3H, m), 3.33 (3H, s), 1.35 (9H, s).

Step E: (S)-3-amino-5-methyl-2,3-dihydropyrido[4,3-b][1,4]oxazepin-4 (5H)-one dihydrochloride To a solution of (S)-tert-butyl (5-methyl-4-oxo-2,3,4,5-tetrahydropyrido[4,3-b][1,4]oxazepin-3-yl)carbamate (600 mg, 2.04 mmol) in EtOAc (5.0 mL) was added HCl (5 M solution in EtOAc, 6.0 mL, 30 mmol) at room temperature. The reaction mixture was stirred at room temperature for 2 hours and concentrated in vacuo to afford (S)-3-amino-5-methyl-2,3-dihydropyrido[4,3-b][1,4]oxazepin-4 (5H)-one dihydrochloride (300 mg, 64%) as a white solid. $^1$H-NMR (400 MHz, DMSO-d$_6$+D$_2$O): δ 7.98 (1H, d, J=6.4 Hz), 7.98 (1H, s), 6.95 (1H, d, J=6.8 Hz), 4.41 (1H, m), 3.87 (1H, d, J=3.2 Hz), 3.85 (1H, d, J=3.2 Hz), 3.28 (3H, s).

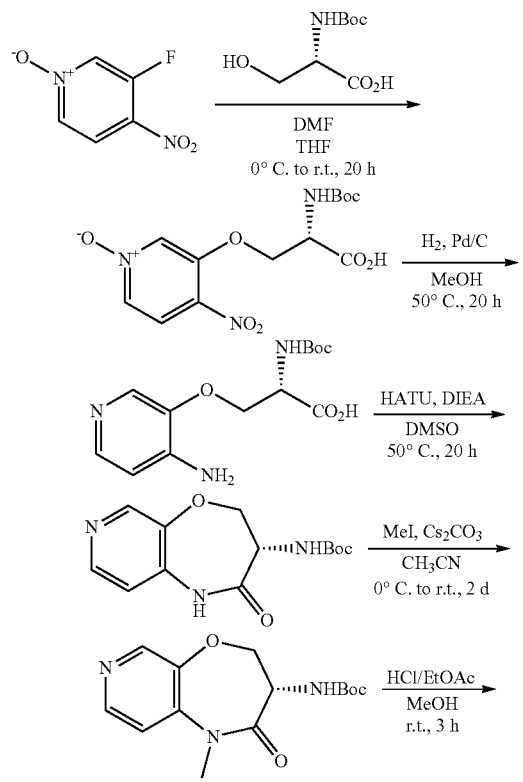

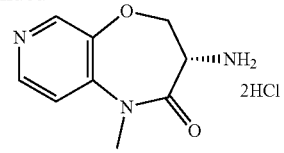

Intermediate 19: (S)-3-amino-1-methyl-3,4-dihydro-pyrido[3,4-b][1,4]oxazepin-2 (1H)-one dihydrochloride

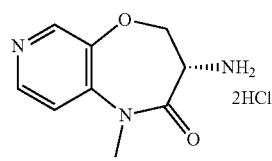

Step A: (S)-3-(2-((tert-butoxycarbonyl)amino)-2-carboxyethoxy)-4-nitropyridine 1-oxide To a solution of N-Boc-L-serine (34.0 g, 166 mmol) in dry THF (800 mL) was slowly added NaH (60 wt %, 13.3 g, 333 mmol) in portions at 0° C. The mixture was stirred at 0° C. for 1 hour. After slow addition of a solution of 3-fluoro-4-nitropyridine 1-oxide (24.0 g, 151 mmol) in dry THF (100 mL), the reaction mixture was stirred at room temperature for 20 hours. After quenched with water, the mixture was neutralized with 1 M aq. HCl solution and then extracted with EtOAc (200 mL×3). The combined organic layers were washed with brine and water, dried over Na$_2$SO$_4$, filtered and concentrated in vacuo. The residue was purified by column chromatography on SiO$_2$(DCM:MeOH=20:1) to afford (S)-3-(2-((tert-butoxycarbonyl)amino)-2-carboxy-ethoxy)-4-nitropyridine 1-oxide (8.20 g, 16%) as a yellow solid. $^1$H-NMR (400 MHz, DMSO-d$_6$): δ 8.50 (1H, s), 8.02 (2H, s), 7.14 (1H, d, J=8.0 Hz), 4.46-4.38 (3H, m), 1.37 (9H, s).

Step B: (S)-3-((4-aminopyridin-3-yl)oxy)-2-((tert-butoxycarbonyl)amino)propanoic acid A suspension of (S)-3-(2-((tert-butoxycarbonyl)amino)-2-carboxyethoxy)-4-nitropyridine 1-oxide (8.10 g, 23.6 mmol) and Pd/C (10 wt %, 1.00 g, 0.12 eq.) in MeOH (100 mL) was stirred at 50° C. for 20 hours under hydrogen atmosphere (1 atm). After filtration through a Celite pad while washing with MeOH, the filtrate was concentrated in vacuo to afford (S)-3-((4-aminopyridin-3-yl)oxy)-2-((tert-butoxycarbonyl)amino)propanoic acid (7.01 g, 100%) as a brown solid. $^1$H-NMR (400 MHz, DMSO-d$_6$): δ 7.83-7.73 (1H, m), 6.56-6.52 (1H, m), 6.15-5.95 (1H, m), 3.69-3.58 (2H, m), 3.46-3.41 (1H, m), 1.37 (9H, s).

Step C: (S)-tert-butyl (4-oxo-2,3,4,5-tetrahydro-pyrido[3,2-b][1,4]oxazepin-3-yl)carbamate To a solution of (S)-3-((4-aminopyridin-3-yl)oxy)-2-((tert-butoxycarbonyl)amino)propanoic acid (6.00 g, 23.6 mmol) in DMSO (50 mL) was added DIPEA (7.15 g, 70.8 mmol) followed by HATU (8.96 g, 23.6 mmol) at room temperature. The reaction mixture was stirred at 50° C. for 20 hours. After dilution with H₂O (100 mL), the mixture was extracted with EtOAc (150 mL×3). The combined organic layers were dried over Na₂SO₄, filtered and concentrated in vacuo. The residue was purified by column chromatography on C18 (MeCN/H₂O) to afford (S)-tert-butyl (2-oxo-1,2,3,4-tetrahydropyrido[3,4-b][1,4]oxazepin-3-yl)carbamate (510 mg, 9%) as a light yellow solid. ¹H-NMR (400 MHz, DMSO-d₆): δ 10.96 (1H, br), 8.35 (1H, br), 8.07 (1H, s), 8.02 (1H, d, J=5.2 Hz), 6.83 (1H, d, J=5.2 Hz), 1.51 (3H, s), 1.31 (9H, s).

Step D: (S)-tert-butyl (1-methyl-2-oxo-1,2,3,4-tetrahydropyrido[3,4-b][1,4]oxazepin-3-yl)carbamate To a solution of (S)-tert-butyl (2-oxo-1,2,3,4-tetrahydropyrido[3,4-b][1,4]oxazepin-3-yl)carbamate (400 mg, 1.43 mmol) in MeCN (5.0 mL) was added Cs₂CO₃ (232 mg, 0.710 mmol) followed by a solution of MeI (161 mg, 1.41 mmol) in MeCN (2.0 mL) at 0° C. The reaction mixture was stirred at room temperature for 2 days. After quenched with water, the mixture was extracted with EtOAc (20 mL×3). The combined organic layers were dried over Na₂SO₄, filtered and concentrated in vacuo. The residue was purified by column chromatography on SiO₂ (pet. ether:EtOAc=1:1) to afford (S)-tert-butyl (1-methyl-2-oxo-1,2,3,4-tetrahydropyrido[3,4-b][1,4]oxazepin-3-yl)carbamate (110 mg, 26%) as a white solid. ¹H-NMR (400 MHz, DMSO-d₆): δ 8.35 (1H, br), 8.15 (1H, d, J=5.6 Hz), 8.12 (1H, s), 7.11 (1H, d, J=5.2 Hz), 3.27 (3H, s), 1.54 (3H, s), 1.28 (9H, s).

Step E: (S)-3-amino-1-methyl-3,4-dihydropyrido[3,4-b][1,4]oxazepin-2 (1H)-one dihydrochloride To a solution of (S)-tert-butyl (1-methyl-2-oxo-1,2,3,4-tetrahydropyrido[3,4-b][1,4]oxazepin-3-yl)carbamate (110 mg, 0.370 mmol) in MeOH (5.0 mL) was added HCl (6 M solution in EtOAc, 5.0 mL, 30 mmol) at room temperature. The reaction mixture was stirred at room temperature for 3 hours and concentrated in vacuo to afford (S)-3-amino-1-methyl-3,4-dihydropyrido[3,4-b][1,4]oxazepin-2 (1H)-one dihydrochloride (51 mg, 51%) as a brown solid. ¹H-NMR (400 MHz, DMSO-d₆): δ 8.65 (1H, s), 8.57 (1H, d, J=6.4 Hz), 7.70 (11H, d, J=6.0 Hz), 3.41 (3H, s), 1.76 (3H, s).

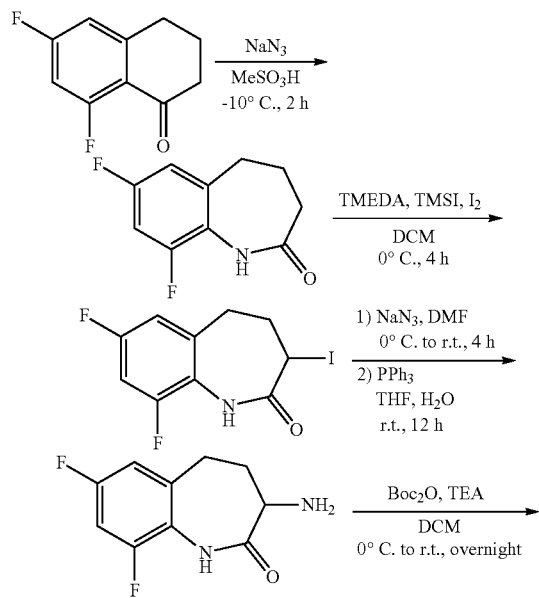

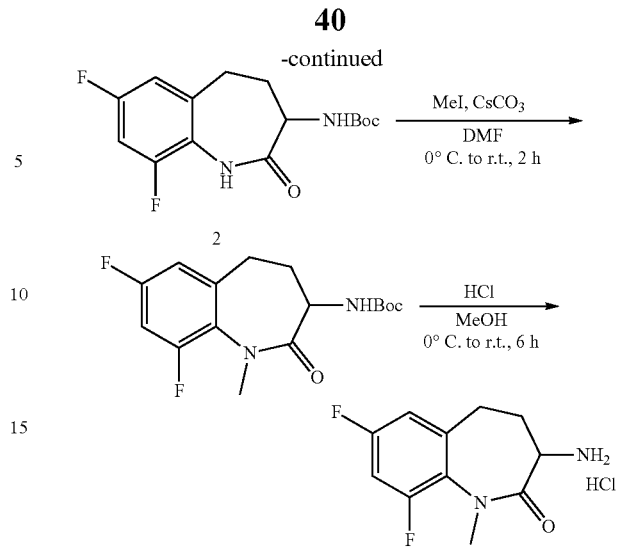

Intermediate 20: 3-amino-7,9-difluoro-4,5-dihydro-1H-benzo[b]azepin-2 (3H)-one

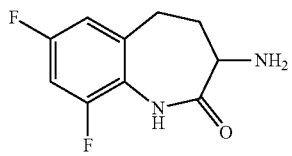 [SMILES: NC1CCc2cc(F)cc(F)c2NC1=O]

Step A: 7,9-difluoro-4,5-dihydro-1H-benzo[b]azepin-2 (3H)-one

To a solution of 6,8-difluoro-3,4-dihydronaphthalen-1 (2H)-one (800 mg, 4.39 mmol) in methansulfonic acid (6.0 mL, 92 mmol) was added sodium azide (350 mg, 5.38 mmol) at −10° C. The reaction mixture was stirred at −10° C. for 2 hours. After quenched with ice-water, a precipitated solid was collected by filtration, washed with hexanes, and then dried under vacuum to afford 7,9-difluoro-4,5-dihydro-1H-benzo[b]azepin-2 (3H)-one (700 mg, 81%) as a white solid. ¹H-NMR (400 MHz, DMSO-d₆): δ 9.40 (11H, brs), 7.19 (11H, t, J=9.6 Hz), 7.60 (1H, d, J=10.0 Hz), 2.91 (1H, q, J=6.4 Hz), 2.73 (2H, t, J=6.8 Hz), 2.14-2.08 (2H, m), 1.87-1.82 (11H, m).

Step B: 7,9-difluoro-3-iodo-4,5-dihydro-1H-benzo[b]azepin-2 (3H)-one

To a solution of 7,9-difluoro-4,5-dihydro-1H-benzo[b]azepin-2 (3H)-one (700 mg, 3.55 mmol) in DCM (10 mL) was slowly added TMEDA (1.61 mL, 10.7 mmol) followed by TMSI (1.45 mL, 10.7 mmol) at 0° C. under Ar atmosphere. The mixture was stirred at 0° C. for 2 hours. After addition of iodine (1.30 g, 5.12 mmol), the reaction mixture was stirred at 0° C. for further 2 hours and then quenched with saturated aq. Na₂S₂O₃. The mixture was stirred at room temperature for 1 hour and extracted with EtOAc. The separated organic layer was washed with 1 M aq. HCl and brine, dried over Na₂SO₄, filtered and concentrated in vacuo to afford 7,9-difluoro-3-iodo-4,5-dihydro-1H-benzo[b]azepin-2 (3H)-one (700 mg, 61%). ¹H-NMR (400 MHz, DMSO-d$_6$): δ 9.98 (1H, brs), 7.26-7.21 (11H, m), 7.09 (1H, d, J=8.4 Hz), 4.01 (1H, dd, J=11.2, 8.0 Hz), 2.80-2.73 (2H, m), 2.43-2.33 (1H, m), 2.14-2.08 (1H, m).

Step C: 3-amino-7,9-difluoro-4,5-dihydro-1H-benzo[b]azepin-2 (3H)-one

To a solution of 7,9-difluoro-3-iodo-4,5-dihydro-1H-benzo[b]azepin-2 (3H)-one (700 mg, 2.17 mmol) in DMF (5.0 mL) was added sodium azide (211 mg, 3.25 mmol) at 0° C. The mixture was stirred at room temperature for 4 hours. After quenched with ice-water, the mixture was stirred at 0° C. for 1 hour. A precipitated solid was collected by filtration, washed with cold water to afford azide compound. To a solution of the azide compound in THF (10 mL) and water (1.0 mL) was added PPh$_3$ (568 mg, 2.17 mmol). The reaction mixture was stirred at room temperature for 12 hours. After concentrated in vacuo, the residue was purified by column chromatography on SiO$_2$ (Hexanes:EtOAc=1:2) to afford 3-amino-7,9-difluoro-4,5-dihydro-1H-benzo[b]azepin-2 (3H)-one (350 mg, 76%) as a white solid. LC-MS: m/z=213.00 [M+H]$^+$.

Intermediate 21: 3-amino-7,9-difluoro-1-methyl-1,3,4,5-tetrahydro-2H-benzo[b]azepin-2-one hydrochloride

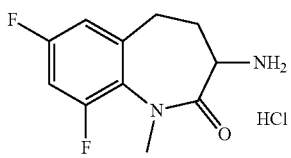 [SMILES: CN1C(=O)C(N)CCc2cc(F)cc(F)c21 ; Cl]

Step A: tert-butyl 7,9-difluoro-2-oxo-2,3,4,5-tetrahydro-1H-benzo[b]azepin-3-ylcarbamate A mixture of 3-amino-7,9-difluoro-4,5-dihydro-1H-benzo[b]azepin-2 (3H)-one (130 mg, 0.613 mmol) and TEA (171 μL, 1.23 mmol) in DCM (5.0 mL) was stirred at room temperature for 5 minutes and cooled to 0° C. After addition of a solution of Boc$_2$O (156 μL, 0.674 mmol) in DCM (3.0 mL), the reaction mixture was stirred at 0° C. for 2 hours and then at room temperature overnight. After quenched with water, the mixture was extracted with EtOAc, washed with 0.5 M aq. HCl and water, dried over Na$_2$SO$_4$, filtered, concentrated in vacuo to afford tert-butyl 7,9-difluoro-2-oxo-2,3,4,5-tetrahydro-1H-benzo[b]azepin-3-ylcarbamate (180 mg, 94%). $^1$H-NMR (400 MHz, CDCl$_3$): δ 7.21 (1H, brs), 6.82-6.78 (2H, m), 5.45 (1H, d, J=6.8 Hz), 4.32-4.26 (11H, m), 3.00-2.93 (11H, m), 2.75-2.65 (2H, m), 2.04-1.96 (11H, m), 1.41 (9H, s).

Step B: tert-butyl 7,9-difluoro-1-methyl-2-oxo-2,3,4,5-tetrahydro-1H-benzo[b]azepin-3-ylcarbamate To a solution of tert-butyl 7,9-difluoro-2-oxo-2,3,4,5-tetrahydro-1H-benzo[b]azepin-3-ylcarbamate (180 mg, 0.576 mmol) in DMF (4.0 mL) was added Cs$_2$CO$_3$ (225 mg, 0.692 mmol) at 0° C. The mixture was stirred at 0° C. for 5 minutes. After addition of a solution of MeI (43.2 μL, 0.692 mmol) in DMF (1.0 mL), the reaction mixture was stirred at 0° C. for 1 hour and then at room temperature for further 1 hour. After quenched with water, the mixture was extracted with EtOAc, dried over Na$_2$SO$_4$, filtered and concentrated in vacuo. The residue was purified by column chromatography on SiO$_2$ (Hexanes:EtOAc=2:1) to afford tert-butyl 7,9-difluoro-1-methyl-2-oxo-2,3,4,5-tetrahydro-1H-benzo[b]azepin-3-ylcarbamate (150 mg, 80%) as a colorless oil. $^1$H-NMR (400 MHz, CDCl$_3$): δ 6.84-6.76 (2H, m), 5.51 (1H, d, J=6.4 Hz), 4.25-4.19 (1H, m), 3.30 (3H, d, J=2.0 Hz), 2.86-2.77 (1H, m), 2.63-2.51 (2H, m), 1.96-1.88 (1H, m), 1.40 (9H, s).

Step C: 3-amino-7,9-difluoro-1-methyl-1,3,4,5-tetrahydro-2H-benzo[b]azepin-2-one hydrochloride To a solution of tert-butyl 7,9-difluoro-1-methyl-2-oxo-2,3,4,5-tetrahydro-1H-benzo[b]azepin-3-ylcarbamate (60 mg, 0.184 mmol) in MeOH (3.0 mL) was added HCl (2 M in Et$_2$O, 919 μL, 1.84 mmol) at 0° C. The reaction mixture was stirred at room temperature for 6 hours and then concentrated in vacuo to afford 3-amino-7,9-difluoro-1-methyl-1,3,4,5-tetrahydro-2H-benzo[b]azepin-2-one hydrochloride (48 mg, 100%). LC-MS: m/z=227.04 [M+H]$^+$.

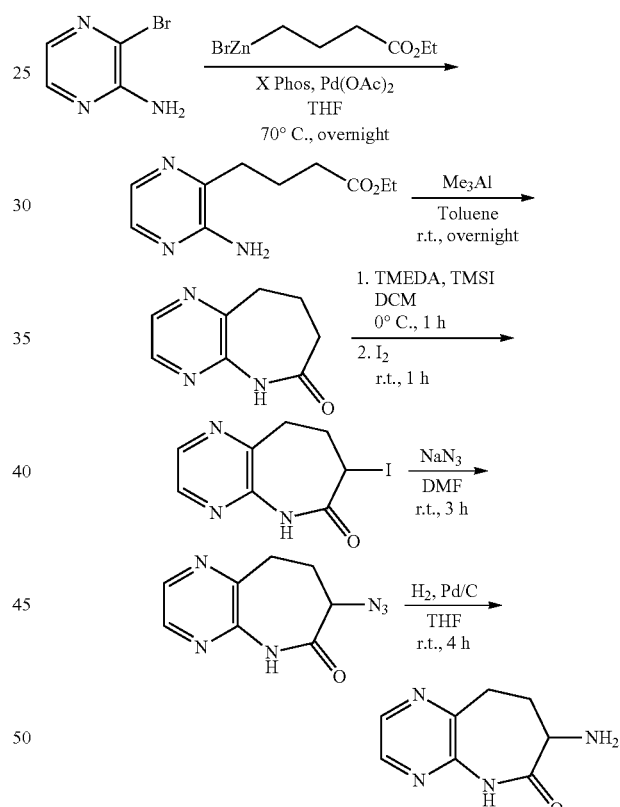

Intermediate 22: 7-amino-5H,7H,8H,9H-pyrazino[2,3-b]azepin-6-one

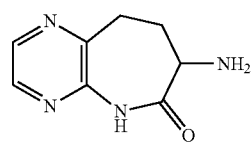 [SMILES: NC1CCc2nccnc2NC1=O]

Step A: Ethyl 4-(3-aminopyrazin-2-yl)butanoate

To a mixture of 3-bromopyrazin-2-amine (1.20 g, 6.89 mmol), X-Phos (657 mg, 1.38 mmol) and Pd(OAc)$_2$ (154 mg, 0.690 mmol) in THF (20 mL) was added a solution of ethyl 4-(bromozincio)butanoate (0.5 M in THF, 80 mL, 40 mmol) at room temperature under N$_2$ atmosphere. The reaction mixture was stirred at 70° C. overnight and cooled to room temperature. After quenched with 1 N aq. HCl (100 mL), the mixture was extracted with EtOAc twice. The separated aqueous layer was basified with 6 N aq. NaOH until pH 9 and then extracted with EtOAc twice. The combined organic layers were washed with brine, dried over Na$_2$SO$_4$, filtered and concentrated in vacuo to afford ethyl 4-(3-aminopyrazin-2-yl)butanoate (1.19 g, 89%) as a yellow oil. LC-MS: m/z=210.10 [M+H]$^+$.

Step B: 5H,7H,8H,9H-pyrazino[2,3-b]azepin-6-one

To a solution of ethyl 4-(3-aminopyrazin-2-yl)butanoate (1.04 g, 4.99 mmol) in toluene (45 mL) was added a solution of AlMe$_3$ (2 M in toluene, 15.0 mL, 30.0 mmol). The reaction mixture was stirred at room temperature overnight. After quenched with water, the mixture was extracted with DCM twice. The combined organic layers were washed with brine, dried over Na$_2$SO$_4$, filtered and concentrated in vacuo. The residue was purified by column chromatography on SiO$_2$ (DCM:MeOH=10:1) to give 5H,7H,8H,9H-pyrazino[2,3-b]azepin-6-one (600 mg, 73%) as a yellow solid. LC-MS: m/z=164.05 [M+H]$^+$.

Step C: 7-iodo-5H,7H,8H,9H-pyrazino[2,3-b]azepin-6-one

To a solution of 5H,7H,8H,9H-pyrazino[2,3-b]azepin-6-one (300 mg, 1.84 mmol) in DCM (20 mL) was added TMEDA (2.13 g, 18.3 mmol), followed by TMSI (3.67 g, 18.3 mmol) over 25 min at 0° C. The mixture was stirred for 1 hour. After addition of I2 (933 mg, 3.67 mmol), the reaction mixture was stirred at room temperature for further 1 hour and then quenched with saturated aq. sodium thiosulfate. The mixture was extracted with DCM twice. The combined organic layers were washed with brine, dried over Na$_2$SO$_4$, filtered and concentrated in vacuo. The residue was purified by column chromatography on SiO$_2$ (Pet. ether: EtOAc=1:1) to give 7-iodo-5H,7H,8H,9H-pyrazino[2,3-b]azepin-6-one (330 mg, 62%) as a yellow solid. LC-MS: m/z=289.95 [M+H]$^+$.

Step D: 7-azido-5H,7H,8H,9H-pyrazino[2,3-b]azepin-6-one

To a solution of 7-iodo-5H,7H,8H,9H-pyrazino[2,3-b]azepin-6-one (300 mg, 1.03 mmol) in DMF (5.0 mL) was added NaN$_3$ (269 mg, 4.15 mmol). The reaction mixture was stirred at room temperature for 3 hours. After quenched with water, the mixture was extracted with EtOAc twice. The combined organic layers were washed with brine, dried over Na$_2$SO$_4$, filtered and concentrated in vacuo to afford 7-azido-5H,7H,8H,9H-pyrazino[2,3-b]azepin-6-one (163 mg, 77%) as a yellow solid. LC-MS: m/z=205.05 [M+H]$^+$.

Step E: 7-amino-5H,7H,8H,9H-pyrazino[2,3-b]azepin-6-one

A suspension of 7-azido-5H,7H,8H,9H-pyrazino[2,3-b]azepin-6-one (163 mg, 0.80 mmol) and Pd/C (10%, 16.0 mg) in THF (30 mL) was stirred at room temperature for 4 hours under H$_2$ atmosphere (1 atm). After filtration through a Celite pad, the filtrate was concentrated in vacuo. The residue was purified by reverse phase column to afford 7-amino-5H,7H,8H,9H-pyrazino[2,3-b]azepin-6-one (60 mg, 42%) as a white solid. $^1$H-NMR (400 MHz, CD$_3$OD): δ 8.32 (1H, dd, J=2.6, 0.7 Hz), 8.29 (1H, d, J=2.6 Hz), 3.45 (1H, dd, J=11.8, 7.5 Hz), 3.08 (1H, ddd, J=14.4, 12.0, 8.1 Hz), 2.99 (1H, ddd, J=14.2, 7.6, 2.2 Hz), 2.62 (1H, ddt, J=13.1, 12.1, 7.5 Hz), 2.09 (1H, dddd, J=13.0, 11.8, 8.1, 2.1 Hz).

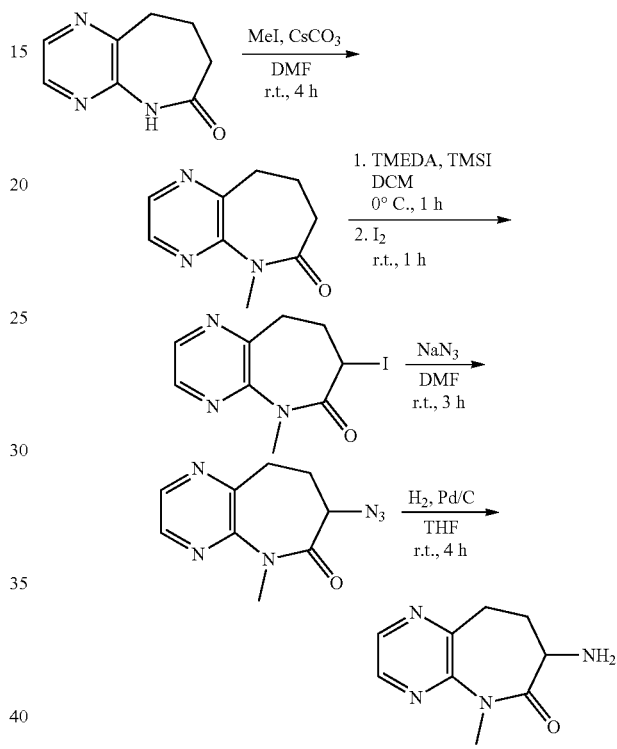

Intermediate 23: 7-amino-5-methyl-7H,8H,9H-pyrazino[2,3-b]azepin-6-one

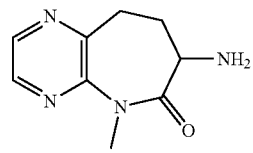

Step A: 5-methyl-7H,8H,9H-pyrazino[2,3-b]azepin-6-one

To a solution of 5H,7H,8H,9H-pyrazino[2,3-b]azepin-6-one (See Intermediate 22, 300 mg, 1.84 mmol) in DMF (5.0 mL) was added Cs$_2$CO$_3$ (1.19 g, 3.67 mmol) followed by MeI (521 mg, 3.68 mmol) at room temperature. The reaction mixture was stirred at room temperature for 4 hours. After quenched with water, the mixture was extracted with EtOAc twice. The combined organic layers were washed with brine, dried over Na$_2$SO$_4$, filtered and concentrated in vacuo to give 5-methyl-7H,8H,9H-pyrazino[2,3-b]azepin-6-one (210 mg, 64%) as a yellow solid. LC-MS: m/z=178.05 [M+H]$^+$.

Step B: 7-iodo-5-methyl-7H,8H,9H-pyrazino[2,3-b]azepin-6-one

To a solution of 5-methyl-7H,8H,9H-pyrazino[2,3-b]azepin-6-one (200 mg, 1.13 mmol) in DCM (20 mL) was added TMEDA (1.31 g, 11.3 mmol) followed by TMSI (2.25 g, 11.3 mmol) over 25 min at 0° C. The mixture was stirred at 0° C. for 1 hour. After addition of I2 (572 mg, 2.26 mmol), the reaction mixture was stirred at room temperature for further 1 hour and then quenched with saturated aq. sodium thiosulfate. The mixture was extracted with DCM twice. The combined organic layers were washed with brine, dried over Na$_2$SO$_4$, filtered and concentrated in vacuo. The residue was purified by column chromatography on SiO$_2$ (Pet. ether:EtOAc=1:1) to give 7-iodo-5-methyl-7H,8H,9H-pyrazino[2,3-b]azepin-6-one (250 mg, 73%) as a yellow solid. LC-MS: m/z=303.90 [M+H]$^+$.

Step C: 7-iodo-5-methyl-7H,8H,9H-pyrazino[2,3-b]azepin-6-one

To a solution of 7-iodo-5-methyl-7H,8H,9H-pyrazino[2,3-b]azepin-6-one (250 mg, 0.82 mmol) in DMF (5.0 mL) was added NaN$_3$ (214 mg, 3.29 mmol) at room temperature. The reaction mixture was stirred at room temperature for 3 hours. After quenched with water, the mixture was extracted with EtOAc (50 mL×3). The combined organic layers were washed with brine, dried over Na$_2$SO$_4$, filtered and concentrated in vacuo to afford 7-azido-5-methyl-7H,8H,9H-pyrazino[2,3-b]azepin-6-one (160 mg, 88%) as a yellow solid. LC-MS: m/z=219.15 [M+H]$^+$.

Step D: 7-amino-5-methyl-7H,8H,9H-pyrazino[2,3-b]azepin-6-one

A suspension of 7-azido-5-methyl-7H,8H,9H-pyrazino[2,3-b]azepin-6-one (160 mg, 0.730 mmol) and Pd/C (10%, 16.0 mg) in THF (30 mL) was stirred at room temperature for 4 hours under H$_2$ atmosphere (1 atm). After filtration through a Celite pad, the filtrate was concentrated in vacuo. The residue was purified by reverse phase column to afford 7-amino-5-methyl-7H,8H,9H-pyrazino[2,3-b]azepin-6-one (70 mg, 50%) as a white oil. $^1$H-NMR (400 MHz, CD$_3$OD): δ 8.44 (1H, dd, J=2.6, 0.7 Hz), 8.34 (1H, d, J=2.6 Hz,), 3.48 (3H, s), 3.39 (11H, dd, J=11.9, 7.6 Hz), 3.09-2.87 (2H, m), 2.57 (1H, tt, J=12.8, 7.6 Hz,), 2.06 (1H, dddd, J=13.1, 11.9, 8.4, 1.4 Hz).

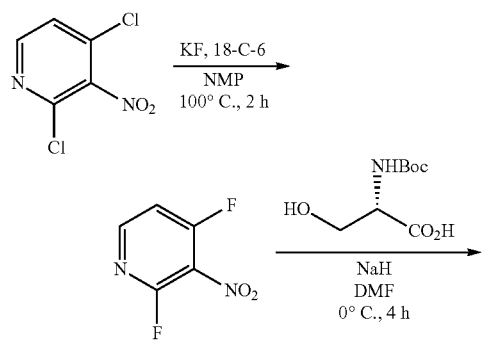

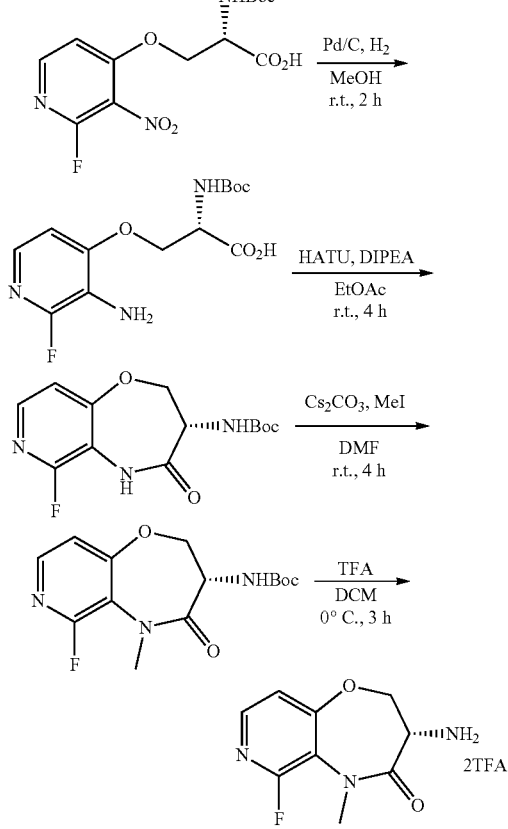

Intermediate 24: (S)-3-amino-6-fluoro-5-methyl-2,3-dihydropyrido[4,3-b][1,4]oxazepin-4 (5H)-one 2TFA

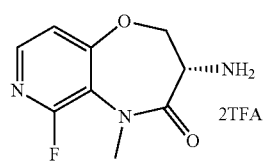

Step A: 2,4-difluoro-3-nitropyridine

A mixture of 2,4-dichloro-3-nitropyridine (5.00 g, 25.9 mmol), KF (spray-dried, 4.52 g, 78.0 mmol) and 18-Crown-6 (1.10 g, 4.15 mmol) in NMP (26 mL) was stirred at 100° C. for 2 hours. The reaction mixture was cooled to room temperature and then partitioned between of water and MTBE. The separated organic layer was washed with brine, dried over Na$_2$SO$_4$, filtered and concentrated in vacuo. The residue was purified by column chromatography on SiO$_2$ (Hexanes:EtOAc=5:1) to afford 2,4-difluoro-3-nitropyridine (2.60 g, 63%) as a pale yellow oil. $^1$H-NMR (400 MHz, CDCl$_3$): δ 8.4 (1H, t, J=6.4 Hz), 7.24 (1H, t, J=7 Hz).

Step B: N-(tert-butoxycarbonyl)-O-(2-fluoro-3-nitropyridin-4-yl)-L-serine

To a suspension of NaH (60 wt %, 1.35 g, 33.7 mmol) in DMF (24 mL) was slowly added a solution of (tert-butoxycarbonyl)-L-serine (3.45 g, 16.8 mmol) in DMF (12 mL) at 0° C. The mixture was stirred at 0° C. for 1 hour. After addition of a solution of 2,4-difluoro-3-nitropyridine (2.45 g, 15.3 mmol) in DMF (12 mL) at 0° C., the reaction mixture was stirred at 0° C. for 4 hours. After quenched with 0.5 M aq. HCl at 0° C., the mixture was extracted with EtOAc, washed with water and brine, dried over $Na_2SO_4$, filtered and concentrated in vacuo. The residue was purified by column chromatography on $SiO_2$ (Hexanes:EtOAc=1:1 to 1:3) to afford N-(tert-butoxycarbonyl)-O-(2-fluoro-3-nitropyridin-4-yl)-L-serine (1.65 g, 31%) as a yellow oil. 1H-NMR (400 MHz, $CDCl_3$): δ 8.20 (1H, d, J=5.6 Hz), 6.98 (1H, d, J=5.6 Hz), 5.56 (1H, d, J=6.4 Hz), 4.66-4.56 (3H, m), 1.45 (9H, s).

Step C: O-(3-amino-2-fluoropyridin-4-yl)-N-(tert-butoxycarbonyl)-L-serine

A suspension of N-(tert-butoxycarbonyl)-O-(2-fluoro-3-nitropyridin-4-yl)-L-serine (1.50 g, 4.34 mmol) and Pd/C (10 wt %, 0.46 g, 0.43 mmol) in MeOH (21 mL) was stirred at room temperature for 2 hours under $H_2$ atmosphere (1 atm). After filtration through a Celite pad while washing with MeOH, the filtrate was concentrated in vacuo to afford O-(3-amino-2-fluoropyridin-4-yl)-N-(tert-butoxycarbonyl)-L-serine (1.30 g, 95%) as a brown oil. LC-MS: m/z=316.13 [M+H]$^+$.

Step D: tert-butyl (S)-(6-fluoro-4-oxo-2,3,4,5-tetrahydropyrido[4,3-b][1,4]oxazepin-3-yl)carbamate To a solution of O-(3-amino-2-fluoropyridin-4-yl)-N-(tert-butoxycarbonyl)-L-serine (1.30 g, 4.12 mmol) in EtOAc (41 mL) was added DIPEA (2.20 mL, 12.4 mmol) followed by HATU (2.35 g, 6.18 mmol) at 0° C. The reaction mixture was stirred at room temperature for 4 hours. After quenched with water, the mixture was extracted with EtOAc. The separated organic layer was washed with brine, dried over $Na_2SO_4$, filtered and concentrated in vacuo. The residue was purified by column chromatography on $SiO_2$ (Hexanes:EtOAc=4:1) to afford tert-butyl (S)-(6-fluoro-4-oxo-2,3,4,5-tetrahydropyrido[4,3-b][1,4]oxazepin-3-yl)carbamate (200 mg, 16%) as a yellow solid. $^1$H-NMR (400 MHz, $CDCl_3$): δ 8.75 (1H, dd, J=4, 1.6 Hz), 8.39 (1H, dd, J=8.8, 1.2 Hz), 7.43 (1H, q, J=8.6 Hz), 4.67-4.58 (1H, m), 4.39 (1H, d, J=3.6 Hz), 3.78-3.69 (1H, m), 3.25-3.14 (1H, m), 1.46 (9H, s).

Step E: tert-butyl (S)-(6-fluoro-5-methyl-4-oxo-2,3,4,5-tetrahydropyrido[4,3-b][1,4]oxazepin-3-yl)carbamate To a solution of tert-butyl (S)-(6-fluoro-4-oxo-2,3,4,5-tetrahydropyrido[4,3-b][1,4]oxazepin-3-yl)carbamate (200 mg, 0.670 mmol) in DMF (6.7 mL) was added $Cs_2CO_3$ (260 mg, 0.810 mmol) followed by MeI (0.0500 mL, 0.810 mmol) at 0° C. The reaction mixture was stirred at room temperature for 4 hours. After dilution with water, the mixture was extracted with EtOAc. The separated organic layer was dried over $Na_2SO_4$, filtered and concentrated in vacuo. The residue was purified by column chromatography on $SiO_2$ (Hexanes:EtOAc=6:1) to afford tert-butyl (S)-(6-fluoro-5-methyl-4-oxo-2,3,4,5-tetrahydropyrido[4,3-b][1,4] oxazepin-3-yl)carbamate (100 mg, 48%) as a colorless foam. LC-MS: m/z=312.13 [M+H]$^+$.

Step F: (S)-3-amino-6-fluoro-5-methyl-2,3-dihydropyrido[4,3-b][1,4]oxazepin-4 (5H)-one 2TFA To a solution of tert-butyl (S)-(6-fluoro-5-methyl-4-oxo-2,3,4,5-tetrahydropyrido[4,3-b][1,4]oxazepin-3-yl)carbamate (80 mg, 0.257 mmol) in DCM (2.5 mL) was added TFA (0.400 mL, 5.14 mmol) at 0° C. The reaction mixture was stirred at 0° C. for 3 hours, and then concentrated in vacuo to afford (S)-6-fluoro-5-methyl-3-((2,2,2-trifluoroacetyl)-14-azanyl)-2,3-dihydropyrido[4,3-b][1,4]oxazepin-4 (5H)-one 2TFA (50 mg, 63%) as a brown oil. LC-MS: m/z=212.08 [M+H]$^+$.

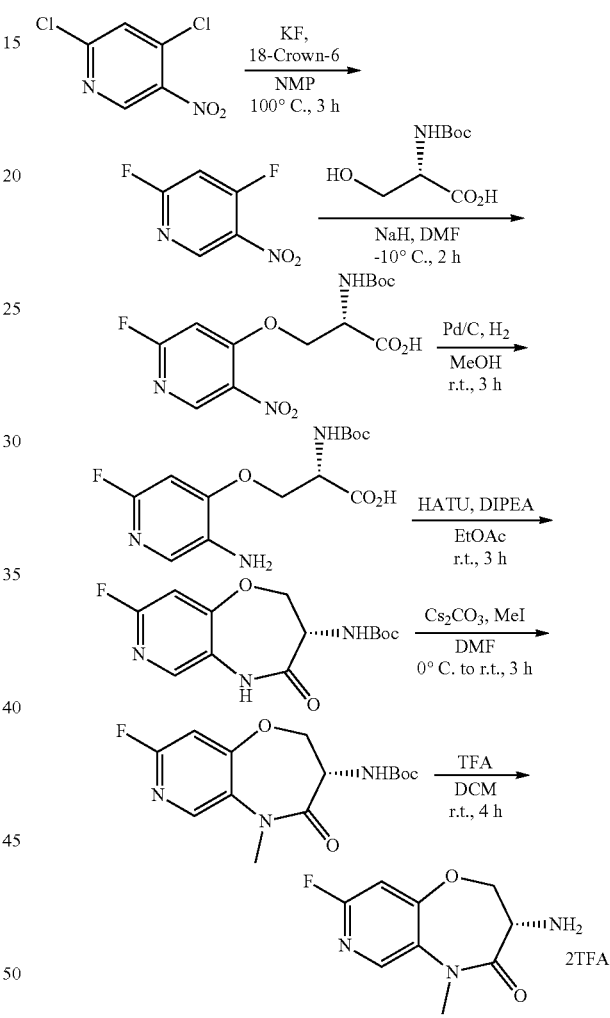

Intermediate 25: (S)-8-fluoro-5-methyl-3-((2,2,2-trifluoroacetyl)-14-azanyl)-2,3-dihydropyrido[4,3-b][1,4]oxazepin-4 (5H)-one 2TFA

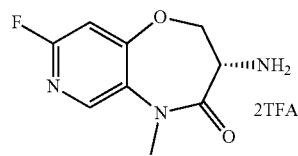

Step A: 2,4-difluoro-5-nitropyridine

A mixture of 2,4-dichloro-5-nitropyridine (4.00 g, 20.7 mmol), 18-crown-6 (0.880 g, 3.32 mmol), KF (spray-dried, 3.61 g, 62.2 mmol) in NMP (21 mL) was stirred at 100° C. for 3 hours. The reaction mixture was cooled to room temperature, and then partitioned between water and MTBE. The separated organic layer was washed with brine, dried over $Na_2SO_4$, filtered and concentrated in vacuo. The residue was purified by column chromatography on $SiO_2$ (Hexanes:EtOAc=9:1) to afford 2,4-difluoro-5-nitropyridine (1.83 g, 55%) as a yellow oil. $^1$H-NMR (400 MHz, $CDCl_3$): δ 9.05 (1H, d, J=7.2 Hz), 6.94 (1H, dd, J=7.2, 2.4 Hz).

Step B: N-(tert-butoxycarbonyl)-O-(2-fluoro-5-nitropyridin-4-yl)-L-serine

To a suspension of NaH (60 wt %, 0.960 g, 23.9 mmol) in DMF (64 mL) was slowly added a solution of (tert-butoxycarbonyl)-L-serine (2.10 g, 10.2 mmol) in DMF (25 mL) at –10° C. The mixture was stirred at for 1 hour at –10° C. After addition of a solution of 2,4-difluoro-5-nitropyridine (1.82 g, 11.4 mmol) in DMF (25 mL) at –10° C., the reaction mixture was stirred at for 2 hours at –10° C. After quenched with 0.5 M aq. HCl at –10° C., the mixture was extracted with EtOAc, washed with water and brine, dried over $Na_2SO_4$, filtered and concentrated in vacuo. The residue was purified by column chromatography on $SiO_2$ (Hexanes:EtOAc=5:1 to 1:1) to afford N-(tert-butoxycarbonyl)-O-(2-fluoro-5-nitropyridin-4-yl)-L-serine (1.34 g, 34%) as a yellow oil. $^1$H NMR (400 MHz, $CDCl_3$): δ 8.73 (1H, s), 6.62 (1H, s), 5.59 (1H, d, J=7.2 Hz), 4.80 (1H, dt, J=7.2, 2.8 Hz), 4.68 (1H, dd, J=9.2, 2.4 Hz), 4.52 (1H, dd, J=9.6, 2.8 Hz), 1.45 (9H, s).

Step C: O-(5-amino-2-fluoropyridin-4-yl)-N-(tert-butoxycarbonyl)-L-serine

A suspension of N-(tert-butoxycarbonyl)-O-(2-fluoro-5-nitropyridin-4-yl)-L-serine (1.34 g, 3.87 mmol) and 5% Pd/C (0.28 g, 0.132 mmol) in MeOH (77 mL) was stirred at room temperature for 3 hours under $H_2$ atmosphere (1 atm). After filtration through a Celite pad while washing with MeOH, the filtrate was concentrated in vacuo to afford O-(5-amino-2-fluoropyridin-4-yl)-N-(tert-butoxycarbonyl)-L-serine (1.22 g, 100%). LC-MS: m/z=316 $[M+H]^+$.

Step D: tert-butyl (S)-(8-fluoro-4-oxo-2,3,4,5-tetrahydropyrido[4,3-b][1,4]oxazepin-3-yl)carbamate To a solution of O-(5-amino-2-fluoropyridin-4-yl)-N-(tert-butoxycarbonyl)-L-serine (1.22 g, 3.87 mmol) in EtOAc (40 mL) was added DIPEA (1.02 mL, 5.81 mmol) followed by HATU (4.42 g, 11.6 mmol) at 0° C. The reaction mixture was stirred at room temperature for 3 hours. After concentration in vacuo, the residue was purified by column chromatography on $SiO_2$ (Hexanes:EtOAc=2:1) to afford tert-butyl (S)-(8-fluoro-4-oxo-2,3,4,5-tetrahydropyrido[4,3-b][1,4]oxazepin-3-yl)carbamate (370 mg, 32%) as a white solid. $^1$H NMR (400 MHz, $CDCl_3$): δ 8.55 (1H, s), 7.92 (1H, s), 6.59 (1H, d, J=2 Hz), 5.64 (1H, d, J=4.4 Hz), 4.65-4.57 (2H, m), 4.31 (1H, td, J=10, 0.8 Hz), 1.46 (9H, s).

Step E: tert-butyl (S)-(8-fluoro-5-methyl-4-oxo-2,3,4,5-tetrahydropyrido[4,3-b][1,4]oxazepin-3-yl)carbamate A mixture of tert-butyl (S)-(8-fluoro-4-oxo-2,3,4,5-tetrahydropyrido[4,3-b][1,4]oxazepin-3-yl)carbamate (0.370 g, 1.24 mmol) and $Cs_2CO_3$ (0.490 g, 1.50 mmol) in DMF (10 mL) was stirred at 0° C. for 5 minutes. After addition of solution of MeI (0.0940 mL, 1.50 mmol) in DMF (5.0 mL), the reaction mixture was stirred at 0° C. for 1 hour and then at room temperature for further 2 hours. After quenched with water, the mixture was extracted with EtOAc, dried over $Na_2SO_4$, filtered and concentrated in vacuo. The residue was purified by column chromatography on $SiO_2$ (Hexanes:EtOAc=2:1) to afford tert-butyl (S)-(8-fluoro-5-methyl-4-oxo-2,3,4,5-tetrahydropyrido[4,3-b][1,4]oxazepin-3-yl)carbamate (0.150 g, 40%) as a white solid. $^1$H NMR (400 MHz, $CDCl_3$): δ 8.09 (1H, s), 6.69 (1H, d, J=2 Hz), 5.53 (1H, d, J=6.4 Hz), 4.70-4.57 (2H, m), 4.31 (1H, dd, J=9.6, 11.6 Hz), 3.44 (3H, s), 1.41 (9H, s).

Step F: (S)-8-fluoro-5-methyl-3-((2,2,2-trifluoroacetyl)-14-azanyl)-2,3-dihydropyrido[4,3-b][1,4]oxazepin-4 (5H)-one 2TFA To a solution of tert-butyl (S)-(8-fluoro-5-methyl-4-oxo-2,3,4,5-tetrahydropyrido[4,3-b][1,4]oxazepin-3-yl)carbamate (0.150 g, 0.490 mmol) in DCM (9.8 mL) was added TFA (0.760 mL, 9.83 mmol) at 0° C. The reaction mixture was stirred at room temperature for 4 hours and concentrated in vacuo to afford (S)-8-fluoro-5-methyl-3-((2,2,2-trifluoroacetyl)-14-azanyl)-2,3-dihydropyrido[4,3-b][1,4]oxazepin-4 (5H)-one (0.150 g, 99%) as a yellow oil. LC-MS: m/z=212 $[M+H]^+$.

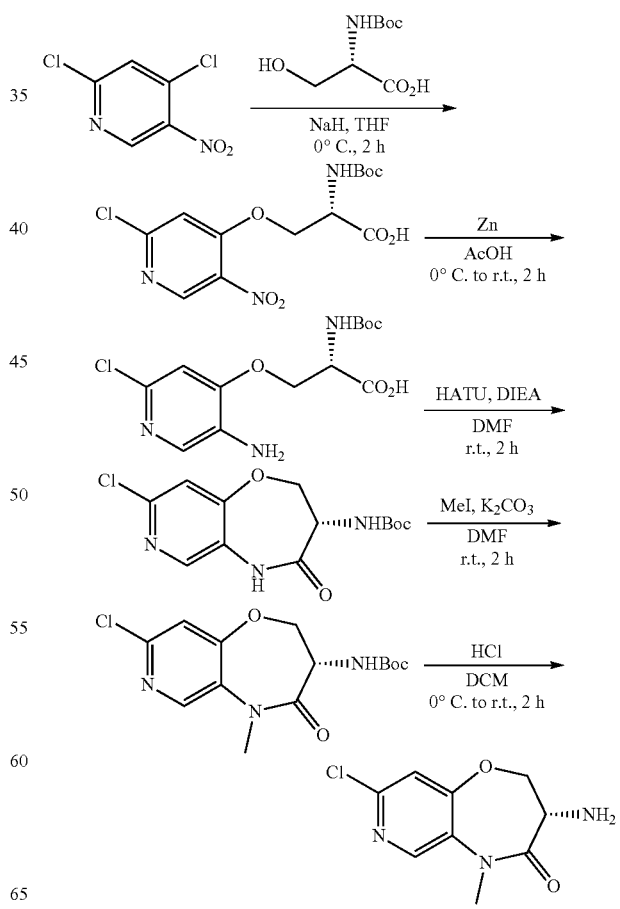

Intermediate 26: (3S)-3-amino-8-chloro-5-methyl-2H,3H-pyrido[4,3-b][1,4]oxazepin-4-one

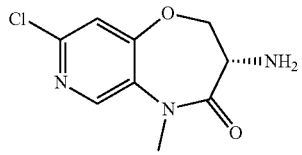

Step A: (2S)-2-[(tert-butoxycarbonyl)amino]-3-[(2-chloro-5-nitropyridin-4-yl)oxy]propanoic acid To a suspension of NaH (60 wt %, 3.60 g, 90.0 mmol) in dry THF (100 mL) was slowly added a solution of (tert-butoxycarbonyl)-L-serine (6.38 g, 31.1 mmol) in dry THF (50 mL) at 0° C. The mixture was stirred at 0° C. for 30 minutes. After addition of a solution of 2,4-dichloro-5-nitropyridine (2.00 g, 10.3 mmol) in dry THF (25 mL) at 0° C., the reaction mixture was stirred at 0° C. for 2 hours. After quenched with cold 0.5 M aq. HCl solution, the mixture was extracted with EtOAc (200 mL×3). The combined organic layer was washed with brine, dried over $Na_2SO_4$, filtered, and concentrated in vacuo to afford (2S)-2-[(tert-butoxycarbonyl)amino]-3-[(2-chloro-5-nitropyridin-4-yl)oxy]propanoic acid (1.20 g, crude) as a yellow oil. $^1$HNMR (400 MHz, DMSO-$d_6$): δ 13.03 (1H, s), 8.88 (11H, s), 7.67 (1H, s), 7.22 (1H, d, J=8.2 Hz), 4.56 (2H, qd, J=10.3, 5.3 Hz), 4.48-4.40 (1H, m), 1.38 (9H, s).

Step B: (2S)-3-[(5-amino-2-chloropyridin-4-yl)oxy]-2-[(tert-butoxycarbonyl)amino]propanoic acid To solution of (2S)-2-[(tert-butoxycarbonyl)amino]-3-[(2-chloro-5-nitropyridin-4-yl)oxy]propanoic acid (1.20 g, 3.31 mmol) in AcOH (20 mL) was added Zn (1.08 g, 16.5 mmol) at 0° C. The reaction mixture was stirred at 0° C. for 2 hours. After filtration through a Celite pad, the filtrate was concentrated in vacuo. The residue was purified by reverse phase column to afford (2S)-3-[(5-amino-2-chloropyridin-4-yl)oxy]-2-[(tert-butoxycarbonyl)amino]propanoic acid (550 mg, 50%) as a brown solid. $^1$H NMR (400 MHz, DMSO-$d_6$): δ 7.58 (1H, s), 6.84 (2H, m), 5.04 (2H, s), 4.37-4.08 (3H, m), 1.39 (9H, s).

Step C: tert-butyl N-[(3S)-8-chloro-4-oxo-2H,3H,5H-pyrido[4,3-b][1,4]oxazepin-3-yl]carbamate To solution of (2S)-3-[(5-amino-2-chloropyridin-4-yl)oxy]-2-[(tert-butoxycarbonyl)amino]propanoic acid (550 mg, 1.65 mmol) in DMF (5.0 mL) was added DIPEA (642 mg, 4.97 mmol) followed by HATU (945 mg, 2.48 mmol) at room temperature. The reaction mixture was stirred at room temperature for 2 hours. After quenched with ice-water, the mixture was extracted with EtOAc (20 mL×3). The combined organic layers were dried over $Na_2SO_4$, filtered and concentrated in vacuo. The residue was purified by column chromatography on $SiO_2$ (Hexanes:EtOAc=2:1) to afford tert-butyl N-[(3S)-8-chloro-4-oxo-2H,3H,5H-pyrido[4,3-b][1,4]oxazepin-3-yl]carbamate (200 mg, 38%) as a yellow solid. LCMS (ESI) m/z: [M+H]$^+$=314.

Step D: tert-butyl N-[(3S)-8-chloro-5-methyl-4-oxo-2H,3H-pyrido[4,3-b][1,4]oxazepin-3-yl]carbamate To a solution of tert-butyl N-[(3S)-8-chloro-4-oxo-2H,3H,5H-pyrido[4,3-b][1,4]oxazepin-3-yl]carbamate (200 mg, 0.637 mmol) in DMF (5.0 mL) was added $K_2CO_3$ (176 mg, 1.27 mmol) followed by a solution of MeI (112 mg, 0.80 mmol) in DMF (1.0 mL). The reaction mixture was stirred at room temperature for 2 hours. After quenched with ice-water, the mixture was extracted with EtOAc (20 mL×3). The combined organic layers were dried over $Na_2SO_4$, filtered, and concentrated in vacuo. The residue was purified by column chromatography on $SiO_2$ (Hexanes:EtOAc=3:1) to afford tert-butyl N-[(3S)-8-chloro-5-methyl-4-oxo-2H,3H-pyrido[4,3-b][1,4]oxazepin-3-yl]carbamate (180 mg, 86%) as a white solid. 1H NMR (400 MHz, DMSO-$d_6$): δ 8.56 (11H, s), 7.39 (11H, s), 7.20 (1H, d, J=7.5 Hz), 4.54-4.40 (3H, m), 3.32 (3H, s), 1.36 (9H, s).

Step E: (3S)-3-amino-8-chloro-5-methyl-2H,3H-pyrido[4,3-b][1,4]oxazepin-4-one To a solution of tert-butyl N-[(3S)-8-chloro-5-methyl-4-oxo-2H,3H-pyrido[4,3-b][1,4]oxazepin-3-yl]carbamate (180 mg, 0.549 mmol) in $CH_2Cl_2$ (3.0 mL) was added HCl (4 M in dioxane, 2.0 mL) at 0° C. The reaction mixture was stirred at room temperature for 1 hour and then concentrated in vacuo. The residue was purified by prep-HPLC to afford (3S)-3-amino-8-chloro-5-methyl-2H,3H-pyrido[4,3-b][1,4] oxazepin-4-one (60 mg, 48%). LCMS (ESI) m/z: [M+H]$^+$=227.95.

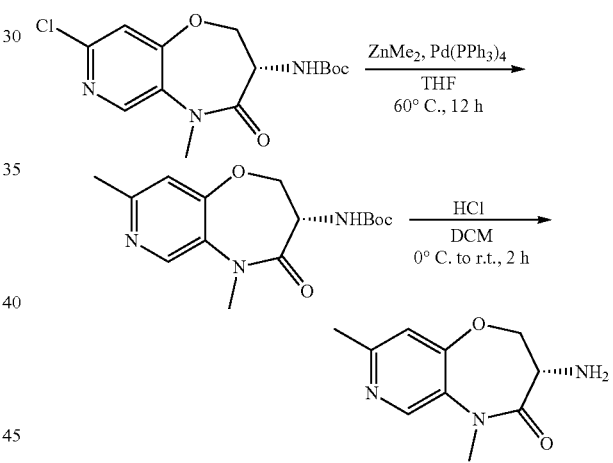

Intermediate 27

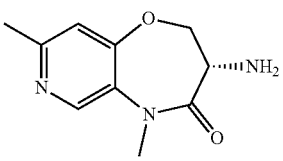

Step A: tert-butyl N-[(3S)-5,8-dimethyl-4-oxo-2H,3H-pyrido[4,3-b][1,4]oxazepin-3-yl]carbamate To a solution of tert-butyl N-[(3S)-8-chloro-5-methyl-4-oxo-2H,3H-pyrido[4,3-b][1,4]oxazepin-3-yl]carbamate (200 mg, 0.610 mmol) and Pd(PPh$_3$)$_4$ (141 mg, 0.122 mmol) in THF (2.0 mL) was slowly added Zn(CH$_3$)$_2$ (1 M in hexane, 2.0 mL, 2.0 mmol) at room temperature. The reaction mixture was stirred at 60° C. for 12 hours. After quenched with 0.5 M aq. AcOH (10 mL) at 0° C., the mixture was extracted with EtOAc (20 mL×3). The combined organic layers were washed with water and brine (20 mL), dried over Na$_2$SO$_4$, filtered and concentrated in vacuo. The residue was purified by column chromatography on SiO$_2$ (Hexanes:EtOAc=4:1 to 1:1) to afford tert-butyl N-[(3S)-5,8-dimethyl-4-oxo-2H,3H-pyrido[4,3-b][1,4]oxazepin-3-yl]carbamate (130 mg, 69%) as a white solid. LCMS (ESI) m/z: [M+H]$^+$=308.

Step B: (3S)-3-amino-5,8-dimethyl-2H,3H-pyrido[4,3-b][1,4]oxazepin-4-one

To a solution of tert-butyl N-[(3S)-5,8-dimethyl-4-oxo-2H,3H-pyrido[4,3-b][1,4]oxazepin-3-yl]carbamate (130 mg, 0.423 mmol) in DCM (3.0 mL) was added HCl (4 M in 1,4-dioxane, 2.0 mL) at 0° C. The reaction mixture was stirred at room temperature for 2 hours and concentrated in vacuo. The residue was purified by prep-HPLC to afford (3S)-3-amino-5,8-dimethyl-2H,3H-pyrido[4,3-b][1,4]oxazepin-4-one (45 mg, 51%) as a white solid. LCMS (ESI) m/z: [M+H]$^+$=208.05.

Example 1: (S)-4-benzyl-N-(4-oxo-2,3,4,5-tetrahydrobenzo[b][1,4]oxazepin-3-yl)-1H-pyrazole-1-carboxamide

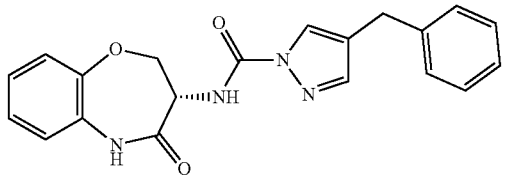 [SMILES: O=C1Nc2ccccc2OC[C@@H]1NC(=O)n1cc(Cc2ccccc2)cn1]

To a solution of (S)-3-amino-2,3-dihydrobenzo[b][1,4]oxazepin-4 (5H)-one hydrochloride (Intermediate 9,100 mg, 0.466 mmol) and TEA (0.195 mL, 1.40 mmol) in THF (4.7 mL) was added 4-nitrophenyl carbonochloridate (122 mg, 0.606 mmol) at 0° C. The mixture was stirred at 0° C. for 45 minutes. After addition of 4-benzyl-1H-pyrazole hydrochloride (Intermediate 1, 118 mg, 0.606 mmol) followed by TEA (0.195 mL, 1.40 mmol) at 0° C., the reaction mixture stirred at room temperature for 18 hours. After quenched with water, the mixture was extracted with EtOAc, dried over Na$_2$SO$_4$, filtered and concentrated in vacuo. The residue was purified by column chromatography on NH—SiO$_2$ (Hexanes:EtOAc=1:3) to give (S)-4-benzyl-N-(4-oxo-2,3,4,5-tetrahydrobenzo[b][1,4]oxazepin-3-yl)-1H-pyrazole-1-carboxamide (10 mg, 6%) as a white solid. $^1$H-NMR (400 MHz, CDCl$_3$): δ 7.94 (1H, d, J=8.0 Hz), 7.90 (1H, s), 7.48 (2H, s), 7.32-7.27 (2H, m), 7.24-7.15 (5H, m), 7.01 (1H, d, J=8.0 Hz), 4.97-4.91 (1H, m), 4.76 (11H, dd, J=10.2, 6.6 Hz), 4.35 (1H, t, J=10.6 Hz), 3.82 (2H, s). LC-MS: m/z=363.2 [M+H]$^+$.

Example 2: (S)-4-(3-fluorobenzyl)-N-(4-oxo-2,3,4,5-tetrahydrobenzo[b][1,4]oxazepin-3-yl)-11H-pyrazole-1-carboxamide

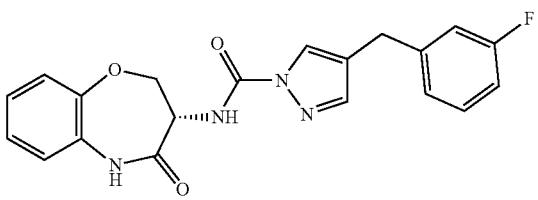 [SMILES: O=C1Nc2ccccc2OC[C@@H]1NC(=O)n1cc(Cc2cccc(F)c2)cn1]

The title compound was prepared in a similar fashion to Example 1 with Intermediates 2 and 9. The crude product was purified by column chromatography on NH—SiO$_2$ (Hexanes:EtOAc=2:1) to give (S)-4-(3-fluorobenzyl)-N-(4-oxo-2,3,4,5-tetrahydrobenzo[b][1,4]oxazepin-3-yl)-1H-pyrazole-1-carboxamide (30%) as a white solid. $^1$H-NMR (400 MHz, CDCl$_3$): δ 7.96 (1H, d, J=6.8 Hz), 7.92 (1H, s), 7.53 (1H, s), 7.48 (11H, s), 7.29-7.12 (4H, m), 7.03-6.86 (4H, m), 4.98-4.92 (11H, m), 4.77 (11H, dd, J=10.4, 6.8 Hz), 4.36 (1H, t, J=10.4 Hz), 3.82 (2H, s). LC-MS: m/z=380.2 [M+H]$^+$.

Example 3: (S)-4-(3-fluorobenzyl)-N-(5-methyl-4-oxo-2,3,4,5-tetrahydrobenzo[b][1,4]oxazepin-3-yl)-4-1H-pyrazole-1-carboxamide

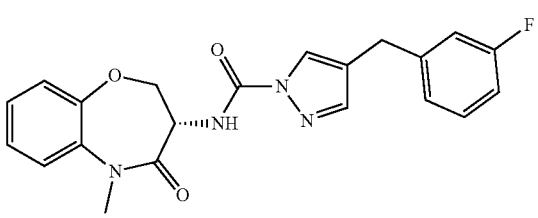 [SMILES: CN1C(=O)[C@@H](NC(=O)n2cc(Cc3cccc(F)c3)cn2)COc2ccccc21]

The title compound was prepared in a similar fashion to Example 1 with Intermediates 2 and 10. The crude product was purified by column chromatography on NH—SiO$_2$ (Hexanes:EtOAc=3:1) to give (S)-4-(3-fluorobenzyl)-N-(5-methyl-4-oxo-2,3,4,5-tetrahydrobenzo[b][1,4]oxazepin-3-yl)-1H-pyrazole-1-carboxamide (36%) as a yellow solid. $^1$H-NMR (400 MHz, CDCl$_3$): δ 8.00 (1H, d, J=6.8 Hz), 7.88 (1H, s), 7.47 (1H, s), 7.28-7.19 (5H, m), 6.96-6.85 (2H, m), 4.94-4.87 (1H, m), 4.71 (1H, t, J=8.6 Hz), 4.31 (11H, t, J=10.2 Hz), 3.81 (2H, s), 3.44 (3H, s). LC-MS: m/z=395.2 [M+H]$^+$.

Example 4: (S)-4-(3-chlorobenzyl)-N-(5-methyl-4-oxo-2,3,4,5-tetrahydrobenzo[b][1,4]oxazepin-3-yl)-1H-pyrazole-1-carboxamide

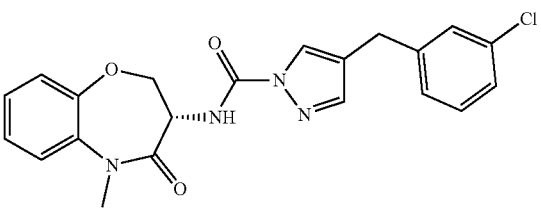 [SMILES: CN1C(=O)[C@@H](NC(=O)n2cc(Cc3cccc(Cl)c3)cn2)COc2ccccc21]

The title compound was prepared in a similar fashion to Example 1 with Intermediates 3 and 10. The crude product was purified by column chromatography on NH—SiO$_2$ (Hexanes:EtOAc=3:1) to give (S)-4-(3-chlorobenzyl)-N-(5-methyl-4-oxo-2,3,4,5-tetrahydrobenzo[b][1,4]oxazepin-3-yl)-1H-pyrazole-1-carboxamide (38%) as a pale yellow solid. $^1$H-NMR (400 MHz, CDCl$_3$): δ 8.01 (1H, d, J=6.8 Hz), 7.88 (1H, s), 7.47 (1H, s), 7.24-7.01 (5H, m), 7.16 (1H, s), 7.06 (11H, d, J=6.8 Hz), 4.94-4.88 (1H, m), 4.72 (1H, t, J=8.4 Hz), 4.32 (1H, t, J=10.4 Hz), 3.79 (2H, s), 3.44 (3H, s). LC-MS: m/z=411.2 [M+H]$^+$.

Example 5: (S)—N-(5-methyl-4-oxo-2,3,4,5-tetrahydrobenzo[b][1,4]oxazepin-3-yl)-4-(3-methylbenzyl)-1H-pyrazole-1-carboxamide

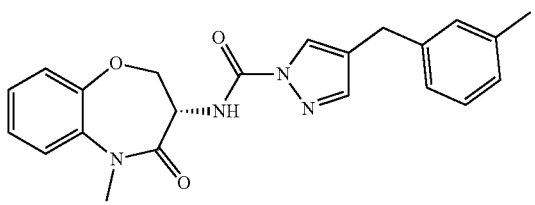 [SMILES: Cc1cccc(Cc2cnn(C(=O)N[C@H]3COc4ccccc4N(C)C3=O)c2)c1]

The title compound was prepared in a similar fashion to Example 1 with Intermediates 4 and 10. The crude product was purified by column chromatography on NH—SiO$_2$ (Hexanes:EtOAc=5:1) to give (S)—N-(5-methyl-4-oxo-2,3,4,5-tetrahydrobenzo[b][1,4]oxazepin-3-yl)-4-(3-methylbenzyl)-1H-pyrazole-1-carboxamide (43%) as a yellow solid. $^1$H-NMR (400 MHz, CDCl$_3$): δ 7.99 (1H, d, J=7.2 Hz), 7.86 (1H, s), 7.47 (11H, s), 7.25-7.16 (4H, m), 7.02 (1H, d, J=7.6 Hz), 6.98-6.96 (2H, m), 4.94-4.87 (1H, m), 4.71 (11H, t, J=8.6 Hz), 4.31 (1H, t, J=10.6 Hz), 3.77 (2H, s), 3.44 (3H, s), 2.31 (3H, s). LC-MS: m/z=391.2 [M+H]$^+$.

Example 6: (S)—N-(5-methyl-4-oxo-2,3,4,5-tetrahydrobenzo[b][1,4]oxazepin-3-yl)-4-(3-(trifluoromethyl)benzyl)-1H-pyrazole-1-carboxamide

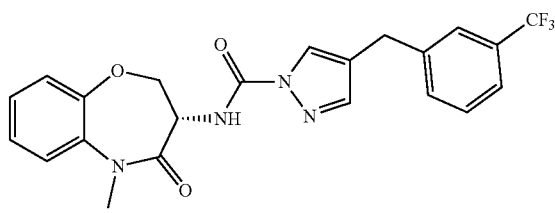 [SMILES: CN1C(=O)[C@@H](NC(=O)n2cc(Cc3cccc(C(F)(F)F)c3)cn2)COc2ccccc21]

The title compound was prepared in a similar fashion to Example 1 with Intermediates 5 and 10. The crude product was purified by column chromatography on NH—SiO$_2$ (Hexanes:EtOAc=3:1) to give (S)—N-(5-methyl-4-oxo-2,3,4,5-tetrahydrobenzo[b][1,4]oxazepin-3-yl)-4-(3-(trifluoromethyl)benzyl)-1H-pyrazole-1-carboxamide (32%) as a white solid. $^1$H-NMR (400 MHz, CDCl$_3$): δ 8.01 (1H, d, J=6.8 Hz), 7.89 (1H, s), 7.49 (11H, d, J=8.0 Hz), 7.48 (1H, s), 7.43 (1H, s), 7.40 (11H, d, J=8.0 Hz), 7.36 (1H, d, J=7.6 Hz), 7.25-7.19 (3H, m), 4.94-4.87 (1H, m), 4.71 (11H, t, J=8.6 Hz), 4.32 (1H, t, J=10.4 Hz), 3.88 (2H, s), 3.44 (3H, s). LC-MS: m/z=445.2 [M+H].

Example 7: (S)-4-(3-cyanobenzyl)-N-(5-methyl-4-oxo-2,3,4,5-tetrahydrobenzo[b][1,4]oxazepin-3-yl)-1H-pyrazole-1-carboxamide

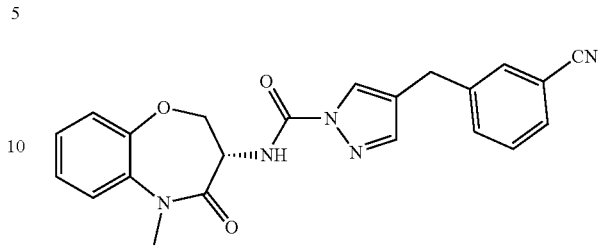

The title compound was prepared in a similar fashion to Example 1 with Intermediates 6 and 10. The crude product was purified by column chromatography on NH—SiO$_2$ (Hexanes:EtOAc=2:1) to give (S)-4-(3-cyanobenzyl)-N-(5-methyl-4-oxo-2,3,4,5-tetrahydrobenzo[b][1,4]oxazepin-3-yl)-1H-pyrazole-1-carboxamide (41%) as a white foam. 1H-NMR (400 MHz, CDCl$_3$): δ 8.02 (1H, d, J=7.2 Hz), 7.89 (1H, s), 7.54-7.50 (1H, m), 7.47 (1H, s), 7.42-7.38 (2H, m), 7.24-7.20 (4H, m), 4.94-4.87 (11H, m), 4.72 (11H, t, J=8.4 Hz), 4.32 (1H, t, J=10.4 Hz), 3.86 (2H, s), 3.44 (3H, s). LC-MS: m/z=402.2 [M+H]$^+$.

Example 8: (S)-4-(4-fluorobenzyl)-N-(5-methyl-4-oxo-2,3,4,5-tetrahydrobenzo[b][1,4]oxazepin-3-yl)-1H-pyrazole-1-carboxamide

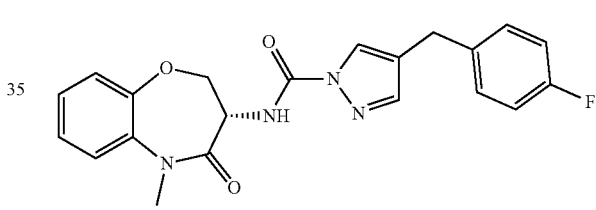

The title compound was prepared in a similar fashion to Example 1 with Intermediates 7 and 10. The crude product was purified by column chromatography on NH—SiO$_2$ (Hexanes:EtOAc=4:1) to give (S)-4-(4-fluorobenzyl)-N-(5-methyl-4-oxo-2,3,4,5-tetrahydrobenzo[b][1,4]oxazepin-3-yl)-1H-pyrazole-1-carboxamide (26%) as a white foam. $^1$H-NMR (400 MHz, CDCl$_3$): δ 7.99 (11H, d, J=6.8 Hz), 7.85 (1H, s), 7.45 (1H, s), 7.25-7.19 (3H, m), 7.13 (2H, t, J=6.8 Hz), 6.98 (2H, t, J=8.6 Hz), 4.94-4.87 (11H, m), 4.71 (1H, t, J=8.6 Hz), 4.31 (11H, t, J=10.4 Hz), 3.78 (2H, s), 3.44 (3H, s). LC-MS: m/z=395.2 [M+H]$^+$.

Example 9: (S)-4-(4-cyanobenzyl)-N-(5-methyl-4-oxo-2,3,4,5-tetrahydrobenzo[b][1,4]oxazepin-3-yl)-1H-pyrazole-1-carboxamide

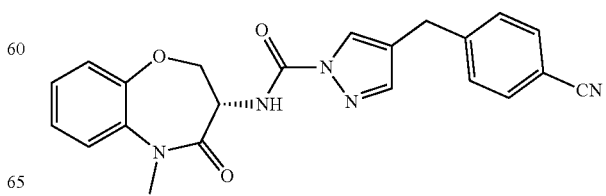

The title compound was prepared in a similar fashion to Example 1 with Intermediates 8 and 10. The crude product was purified by column chromatography on NH—SiO₂ (Hexanes:EtOAc=2:1) to give (S)-4-(4-cyanobenzyl)-N-(5-methyl-4-oxo-2,3,4,5-tetrahydrobenzo[b][1,4]oxazepin-3-yl)-1H-pyrazole-1-carboxamide (73%) as a white foam. ¹H-NMR (400 MHz, CDCl₃): δ 8.01 (1H, d, J=7.2 Hz), 7.89 (1H, s), 7.59 (2H, d, J=8.4 Hz), 7.46 (1H, s), 7.28 (2H, d, J=8.8 Hz), 7.26-7.20 (3H, m), 4.93-4.87 (1H, m), 4.71 (1H, t, J=8.6 Hz), 4.31 (1H, t, J=10.6 Hz), 3.88 (2H, s), 3.44 (3H, s). LC-MS: m/z=402.2 [M+H]⁺.

Example 10: (S)-4-benzyl-N-(6-fluoro-4-oxo-2,3,4,5-tetrahydrobenzo[b][1,4]oxazepin-3-yl)-1H-pyrazole-1-carboxamide

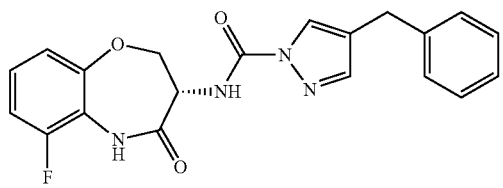 [SMILES: O=C1Nc2c(F)cccc2OC[C@@H]1NC(=O)n1cc(Cc2ccccc2)cn1]

The title compound was prepared in a similar fashion to Example 1 with Intermediates 1 and 11. The crude product was purified by column chromatography on NH—SiO₂ (Hexanes:EtOAc=2:1) to afford (S)-4-benzyl-N-(6-fluoro-4-oxo-2,3,4,5-tetrahydrobenzo[b][1,4]oxazepin-3-yl)-1H-pyrazole-1-carboxamide (3%) as a white solid. ¹H-NMR (400 MHz, CDCl₃): δ 7.97 (1H, d, J=6.8 Hz), 7.92 (11H, s), 7.49 (11H, s), 7.46 (11H, s), 7.30 (1H, t, J=7.4 Hz), 7.24-7.18 (2H, m), 7.12 (1H, q, J=7.6 Hz), 6.98-6.01 (2H, m), 4.98-4.92 (11H, m), 4.75 (11H, q, J=5.5 Hz), 4.36 (11H, t, J=10.2 Hz), 3.83 (2H, s). LC-MS: m/z=381.2 [M+H]⁺.

Example 11: (S)—N-(6-fluoro-4-oxo-2,3,4,5-tetrahydrobenzo[b][1,4]oxazepin-3-yl)-4-(3-fluorobenzyl)-1H-pyrazole-1 carboxamide

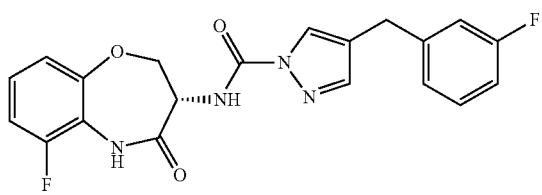

The title compound was prepared in a similar fashion to Example 1 with Intermediates 2 and 11. The crude product was purified by column chromatography on NH—SiO₂ (Hexanes:EtOAc=2:1) to afford (S)—N-(6-fluoro-4-oxo-2,3,4,5-tetrahydrobenzo[b][1,4]oxazepin-3-yl)-4-(3-fluorobenzyl)-1H-pyrazole-1 carboxamide (3.5%) as a white solid. ¹H-NMR (400 MHz, CDCl₃): δ 7.98 (1H, d, J=6.8 Hz), 7.93 (1H, s), 7.49 (1H, s), 7.44 (1H, s), 7.29-7.24 (2H, m), 7.12 (11H, q, J=7.6 Hz), 6.98-6.87 (4H, m), 4.98-4.93 (1H, m), 4.76 (1H, q, J=5.3 Hz), 4.37 (1H, t, J=10.6 Hz), 3.83 (2H, s). LC-MS: m/z=399.1 [M+H]⁺.

Example 12: (S)-4-benzyl-N-(6-fluoro-5-methyl-4-oxo-2,3,4,5-tetrahydrobenzo[b][1,4]oxazepin-3-yl)-1H-pyrazole-1-carboxamide

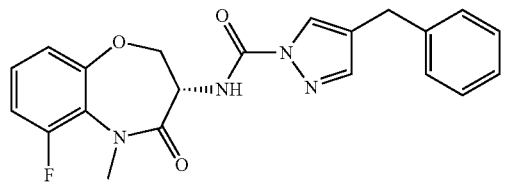 [SMILES: CN1C(=O)[C@@H](NC(=O)n2cc(Cc3ccccc3)cn2)COc2cccc(F)c21]

The title compound was prepared in a similar fashion to Example 1 with Intermediates 1 and 12. The crude product was purified by column chromatography on NH—SiO₂ (Hexanes:EtOAc=2:1) followed by SiO₂ (Hexanes:EtOAc=6:1) to afford (S)-4-benzyl-N-(6-fluoro-5-methyl-4-oxo-2,3,4,5-tetrahydrobenzo[b][1,4]oxazepin-3-yl)-1H-pyrazole-1-carboxamide (27%) as a colorless oil. ¹H-NMR (400 MHz, CDCl₃): δ 7.99 (1H, d, J=7.2 Hz), 7.87 (11H, s), 7.48 (11H, s), 7.31-7.22 (4H, m), 7.20-7.17 (2H, m), 7.06-7.01 (2H, m), 4.96-4.90 (1H, m), 4.69-4.65 (1H, m), 4.30 (11H, t, J=10.4 Hz), 3.82 (2H, s), 3.38 (3H, d, J=1.6 Hz). LC-MS: m/z=395.2 [M+H]⁺.

Example 13: (S)—N-(6-fluoro-5-methyl-4-oxo-2,3,4,5-tetrahydrobenzo[b][1,4]oxazepin-3-yl)-4-(3-fluorobenzyl)-1H-pyrazole-1-carboxamide

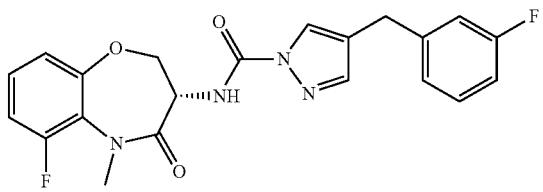 [SMILES: CN1C(=O)[C@@H](NC(=O)n2cc(Cc3cccc(F)c3)cn2)COc2cccc(F)c21]

The title compound was prepared in a similar fashion to Example 1 with Intermediates 2 and 12. The crude product was purified by column chromatography on NH—SiO₂ (Hexanes:EtOAc=2:1) followed by SiO₂ (Hexanes:EtOAc=6:1) to afford (S)—N-(6-fluoro-5-methyl-4-oxo-2,3,4,5-tetrahydrobenzo[b][1,4]oxazepin-3-yl)-4-(3-fluorobenzyl)-1H-pyrazole-1-carboxamide (7.5%) as a colorless oil. ¹H-NMR (400 MHz, CDCl₃): δ 8.00 (1H, d, J=6.8 Hz), 7.88 (1H, s), 7.48 (1H, s), 7.29-7.23 (2H, m), 7.06-7.02 (2H, m), 6.97-6.86 (2H, m), 4.96-4.90 (1H, m), 4.68 (1H, t, J=8.6 Hz), 4.30 (1H, t, J=10.6 Hz), 3.82 (2H, s), 3.38 (3H, d, J=1.6 Hz). LC-MS: m/z=413.2 [M+H]⁺.

Example 14: (S)-4-benzyl-N-(6,8-difluoro-4-oxo-2,3,4,5-tetrahydrobenzo[b][1,4]oxazepin-3-yl)-1H-pyrazole-1-carboxamide

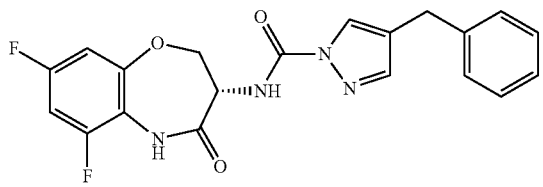 [SMILES: O=C1Nc2c(F)cc(F)cc2OC[C@@H]1NC(=O)n1cc(Cc2ccccc2)cn1]

The title compound was prepared in a similar fashion to Example 1 with Intermediates 1 and 13. The crude product was purified by column chromatography on NH—SiO$_2$ (Hexanes:EtOAc=2:1) to afford (S)-4-benzyl-N-(6,8-difluoro-4-oxo-2,3,4,5-tetrahydrobenzo[b][1,4]oxazepin-3-yl)-1H-pyrazole-1-carboxamide (30%) as a white solid. 1H-NMR (400 MHz, CDCl$_3$): δ 7.96 (1H, d, J=6.4 Hz), 7.91 (1H, s), 7.49 (1H, s), 7.32-7.18 (6H, m), 6.74-6.69 (2H, m), 4.96-4.91 (1 H, m), 4.74 (1H, dd, J=10.8, 5.2 Hz), 4.38 (1H, t, J=10.4 Hz), 3.83 (2H, s). LC-MS: m/z=399.2 [M+H]$^+$.

Example 15: (S)—N-(6,8-difluoro-4-oxo-2,3,4,5-tetrahydrobenzo[b][1,4]oxazepin-3-yl)-4-(3-fluorobenzyl)-1H-pyrazole-1-carboxamide

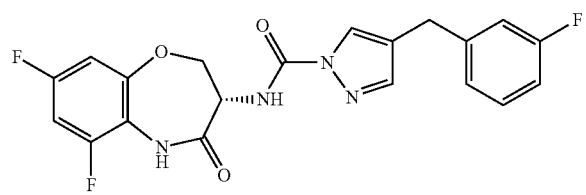 [SMILES: O=C1Nc2c(F)cc(F)cc2OC[C@@H]1NC(=O)n1cc(Cc2cccc(F)c2)cn1]

The title compound was prepared in a similar fashion to Example 1 with Intermediates 2 and 13. The crude product was purified by column chromatography on NH—SiO$_2$ (Hexanes:EtOAc=1:1) to afford (S)—N-(6,8-difluoro-4-oxo-2,3,4,5-tetrahydrobenzo[b][1,4]oxazepin-3-yl)-4-(3-fluorobenzyl)-1H-pyrazole-1-carboxamide (33%) as a white solid. $^1$H-NMR (400 MHz, CDCl$_3$): δ 7.98 (1H, d, J=6.8 Hz), 7.93 (1H, s), 7.49 (1H, s), 7.45 (1H, brs), 7.29-7.24 (1H, m), 6.98-6.89 (3H, m), 6.75-6.69 (2H, m), 4.94 (1H, dt, J=10.4, 5.6 Hz), 4.75 (1H, dd, J=10.8, 5.6 Hz), 4.39 (1H, t, J=10.4 Hz), 3.82 (2H, s). LC-MS: m/z=417.2 [M+H]$^+$.

Example 16: (S)-4-benzyl-N-(6,8-difluoro-5-methyl-4-oxo-2,3,4,5-tetrahydrobenzo[b][1,4]oxazepin-3-yl)-1H-pyrazole-1-carboxamide

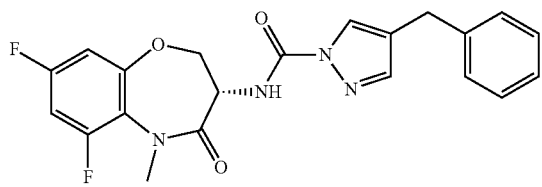 [SMILES: CN1C(=O)[C@@H](NC(=O)n2cc(Cc3ccccc3)cn2)COc2cc(F)cc(F)c21]

The title compound was prepared in a similar fashion to Example 1 with Intermediates 1 and 14. The crude product was purified by column chromatography on NH—SiO$_2$ (Hexanes:EtOAc=1:1) to afford (S)-4-benzyl-N-(6,8-difluoro-5-methyl-4-oxo-2,3,4,5-tetrahydrobenzo[b][1,4]oxazepin-3-yl)-1H-pyrazole-1-carboxamide (32%) as a colorless oil. $^1$H-NMR (400 MHz, CDCl$_3$): δ 7.97 (1H, d, J=7.2 Hz), 7.87 (1H, s), 7.48 (1H, s), 7.31-7.17 (5H, m), 6.84-6.78 (2H, m), 4.93 (1H, dt, J=11.6, 7.2 Hz), 4.66 (1H, dd, J=10.0, 7.6 Hz), 4.31 (11H, t, J=10.4 Hz), 3.82 (2H, s), 3.35 (3H, d, J=2.0 Hz). LC-MS: m/z=413.2 [M+H]$^+$.

Example 17: (S)—N-(6,8-difluoro-5-methyl-4-oxo-2,3,4,5-tetrahydrobenzo[b][1,4]oxazepin-3-yl)-4-(3-fluorobenzyl)-1H-pyrazole-1-carboxamide

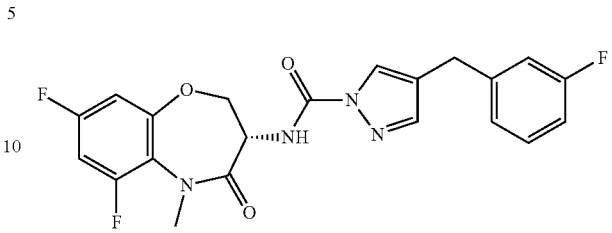

The title compound was prepared in a similar fashion to Example 1 with Intermediates 2 and 14. The crude product was purified by column chromatography on NH—SiO$_2$ (Hexanes:EtOAc=2:1) to afford (S)—N-(6,8-difluoro-5-methyl-4-oxo-2,3,4,5-tetrahydrobenzo[b][1,4]oxazepin-3-yl)-4-(3-fluorobenzyl)-1H-pyrazole-1-carboxamide (41%) as a colorless oil. $^1$H-NMR (400 MHz, CDCl$_3$): δ 7.98 (1H, d, J=7.2 Hz), 7.89 (1H, s), 7.48 (1H, s), 7.28-7.23 (1H, m), 6.97-6.78 (5H, m), 4.93 (1H, dt, J=11.2, 7.2 Hz), 4.67 (1H, dd, J=9.6, 6.8 Hz), 4.31 (1H, dd, J=10.8, 9.6 Hz), 3.82 (2H, s), 3.35 (3H, d, J=2.4 Hz). LC-MS: m/z=431.2 [M+H]$^+$.

Example 18: (S)-4-benzyl-N-(8-methoxy-5-methyl-4-oxo-2,3,4,5-tetrahydrobenzo[b][1,4]oxazepin-3-yl)-1H-pyrazole-1-carboxamide

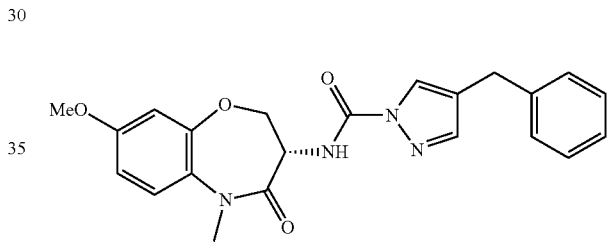

The title compound was prepared in a similar fashion to Example 1 with Intermediates 1 and 15. The crude product was purified by column chromatography on NH—SiO$_2$ (Hexanes:EtOAc=2:1) to give (S)-4-benzyl-N-(8-methoxy-5-methyl-4-oxo-2,3,4,5-tetrahydrobenzo[b][1,4]oxazepin-3-yl)-1H-pyrazole-1-carboxamide (29%) as a colorless oil. $^1$H-NMR (400 MHz, CDCl$_3$): δ 7.99 (11H, d, J=7.2 Hz), 7.87 (11H, s), 7.47 (1H, s), 7.31-7.16 (4H, m), 7.12 (11H, d, J=8.4 Hz), 6.80-6.73 (2H, m), 7.01 (11H, d, J=8.0 Hz), 4.94-4.87 (11H, m), 4.80 (11H, dd, J=9.6, 7.6 Hz), 4.29 (11H, t, J=10.4 Hz), 3.83 (3H, s), 3.81 (2H, s), 3.39 (3H, s). LC-MS: m/z=407.2 [M+H]$^+$.

Example 19: (S)-4-benzyl-N-(7-methoxy-5-methyl-4-oxo-2,3,4,5-tetrahydrobenzo[b][1,4]oxazepin-3-yl)-1H-pyrazole-1-carboxamide

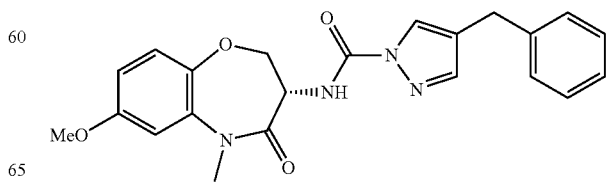

The title compound was prepared in a similar fashion to Example 1 with Intermediates 1 and 16. The crude product was purified by column chromatography on NH—SiO$_2$ (Hexanes:EtOAc=2:1) to give (S)-4-benzyl-N-(7-methoxy-5-methyl-4-oxo-2,3,4,5-tetrahydrobenzo[b][1,4]oxazepin-3-yl)-1H-pyrazole-1-carboxamide (32%) as a colorless oil. $^1$H-NMR (400 MHz, CDCl$_3$): δ 7.96 (1H, d, J=8.0 Hz), 7.86 (1H, s), 7.46 (1H, s), 7.30-7.10 (6H, m), 6.77-6.73 (2H, m), 4.93-4.86 (1H, m), 4.65 (1H, dd, J=9.6, 7.6 Hz), 4.24 (1H, dd, J=11.6, 10 Hz), 3.82 (3H, s), 3.81 (2H, s), 3.41 (3H, s). LC-MS: m/z=407.3 [M+H]$^+$.

Example 20: (S)-4-(3-fluorobenzyl)-N-(7-methoxy-5-methyl-4-oxo-2,3,4,5-tetrahydrobenzo[b][1,4]oxazepin-3-yl)-1H-pyrazole-1-carboxamide

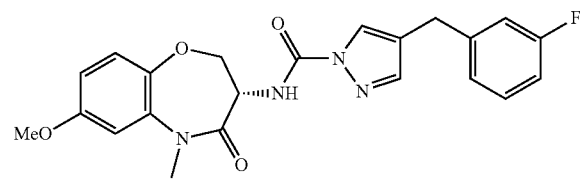 [SMILES: COc1ccc2c(c1)N(C)C(=O)[C@@H](NC(=O)n1cc(Cc3cccc(F)c3)cn1)CO2]

The title compound was prepared in a similar fashion to Example 1 with Intermediates 2 and 16. The crude product was purified by column chromatography on NH—SiO$_2$ (Hexanes:EtOAc=2:1) to give (S)-4-(3-fluorobenzyl)-N-(7-methoxy-5-methyl-4-oxo-2,3,4,5-tetrahydrobenzo[b][1,4]oxazepin-3-yl)-1H-pyrazole-1-carboxamide (35%) as a pale yellow oil. $^1$H-NMR (400 MHz, CDCl$_3$): δ 7.98 (1H, d, J=7.2 Hz), 7.88 (1H, s), 7.47 (1H, s), 7.28-7.22 (2H, m), 7.12 (1 H, d, J=8.4 Hz), 6.96-6.85 (2H, m), 6.78-6.74 (2H, m), 4.94-4.87 (1H, m), 4.66 (1H, dd, J=10, 7.6 Hz), 4.25 (1H, dd, J=11.2, 9.6 Hz), 3.82 (3H, s), 3.81 (2H, s), 3.42 (3H, s). LC-MS: m/z=425.1 [M+H]$^+$.

Example 21: (S)-4-(3-fluorobenzyl)-N-(5-methyl-4-oxo-2,3,4,5-tetrahydropyrido[3,2-b][1,4]oxazepin-3-yl)-1H-pyrazole-1-carboxamide

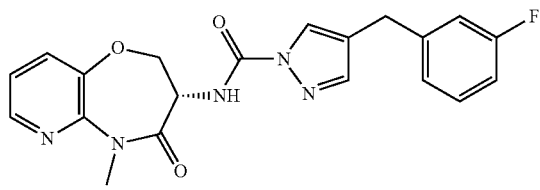 [SMILES: CN1C(=O)[C@@H](NC(=O)n2cc(Cc3cccc(F)c3)cn2)COc2cccnc21]

The title compound was prepared in a similar fashion to Example 1 with Intermediates 2 and 17. The crude product was purified by column chromatography on NH—SiO$_2$ (Hexanes:EtOAc=1:2) followed by SiO$_2$ (Hexanes:EtOAc=1:1) to give (S)-4-(3-fluorobenzyl)-N-(5-methyl-4-oxo-2,3,4,5-tetrahydropyrido[3,2-b][1,4]oxazepin-3-yl)-1H-pyrazole-1-carboxamide (27%) as a pale yellow solid. $^1$H-NMR (400 MHz, CDCl$_3$): δ 8.31 (1H, d, J=3.6 Hz), 8.07 (1H, d, J=6.8 Hz), 7.89 (1H, s), 7.52 (1H, d, J=7.2 Hz), 7.48 (1H, s), 7.27-7.22 (1H, m), 7.20-7.17 (1H, m), 6.96-6.85 (3H, m), 4.93-4.87 (1H, m), 4.78 (1H, t, J=8.2 Hz), 4.38 (1H, t, J=10.4 Hz), 3.81 (2H, s), 3.53 (3H, s). LC-MS: m/z=396.2 [M+H]$^+$.

Example 22: (S)-4-benzyl-N-(5-methyl-4-oxo-2,3,4,5-tetrahydropyrido[4,3-b][1,4]oxazepin-3-yl)-1H-pyrazole-1-carboxamide

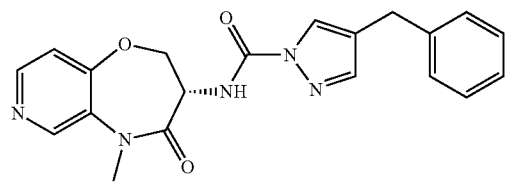 [SMILES: CN1C(=O)[C@@H](NC(=O)n2cc(Cc3ccccc3)cn2)COc2ccncc21]

The title compound was prepared in a similar fashion to Example 1 with Intermediates 1 and 18. The crude product was purified by column chromatography on NH—SiO$_2$ (Hexanes:EtOAc=3:1 to EtOAc) to give (S)-4-benzyl-N-(5-methyl-4-oxo-2,3,4,5-tetrahydropyrido[4,3-b][1,4]oxazepin-3-yl)-1H-pyrazole-1-carboxamide (40%) as a yellow solid. $^1$H-NMR (400 MHz, CDCl$_3$): δ 8.54 (1H, s), 8.44 (1H, d, J=5.2 Hz), 8.00 (1H, d, J=6.4 Hz), 7.87 (1H, s), 7.48 (1H, s), 7.32-7.26 (3H, m), 7.24-7.19 (2H, m), 7.12 (1H, d, J=5.6 Hz), 4.96-4.89 (1H, m), 4.73 (1H, dd, J=10, 6.4 Hz), 4.44 (1H, t, J=10.6 Hz), 3.82 (2H, s), 3.50 (3H, s).

LC-MS: m/z=378.1 [M+H]$^+$.

Example 23: (S)-4-(3-fluorobenzyl)-N-(5-methyl-4-oxo-2,3,4,5-tetrahydropyrido[4,3-b][1,4]oxazepin-3-yl)-1H-pyrazole-1-carboxamide

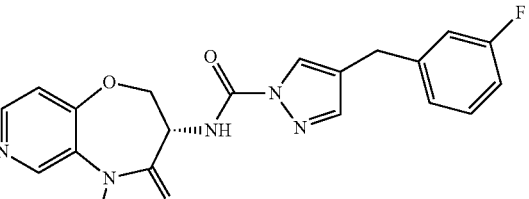

The title compound was prepared in a similar fashion to Example 1 with Intermediates 2 and 18. The crude product was purified by column chromatography on NH—SiO$_2$ (Hexanes:EtOAc=1:2) to give (S)-4-(3-fluorobenzyl)-N-(5-methyl-4-oxo-2,3,4,5-tetrahydropyrido[4,3-b][1,4]oxazepin-3-yl)-1H-pyrazole-1-carboxamide (29%) as a pale yellow solid. $^1$H-NMR (400 MHz, CDCl$_3$): δ 8.54 (1H, s), 8.44 (1H, d, J=4.8 Hz), 8.01 (1H, d, J=7.2 Hz), 7.89 (1H, s), 7.48 (11H, s), 7.29-7.23 (2H, m), 7.12 (1H, d, J=5.2 Hz), 6.97-6.86 (2H, m), 4.96-4.90 (11H, m), 4.74 (1H, dd, J=10, 6.4 Hz), 4.45 (1H, t, J=10.4 Hz), 3.82 (2H, s), 3.50 (3H, s). LC-MS: m/z=396.2 [M+H]$^+$.

Example 24: (S)-4-benzyl-N-(1-methyl-2-oxo-1,2,3,4-tetrahydropyrido[3,4-b][1,4]oxazepin-3-yl)-1H-pyrazole-1-carboxamide

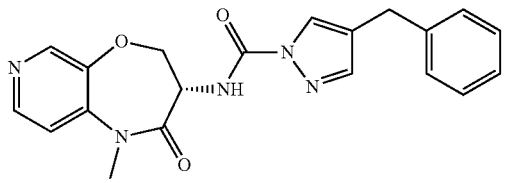 [SMILES: CN1C(=O)[C@@H](NC(=O)n2cc(Cc3ccccc3)cn2)COc2cnccc21]

The title compound was prepared in a similar fashion to Example 1 with Intermediates 1 and 19. The crude product was purified by column chromatography on NH—SiO$_2$ (Hexanes:EtOAc=3:1 to EtOAc only) to give (S)-4-benzyl-N-(1-methyl-2-oxo-1,2,3,4-tetrahydropyrido[3,4-b][1,4]oxazepin-3-yl)-1H-pyrazole-1-carboxamide (8%) as a white foam. $^1$H-NMR (400 MHz, DMSO-d$_6$): δ 9.72 (1H, s), 8.19 (1H, d, J=5.6 Hz), 8.14 (1H, s), 8.05 (1H, s), 7.23 (1H, s), 7.31-7.16 (6H, m), 3.81 (2H, s), 3.31 (3H, s), 1.77 (3H, s). LC-MS: m/z=378.1 [M+H].

Example 25: 4-benzyl-N-(7,9-difluoro-2-oxo-2,3,4,5-tetrahydro-1H-benzo[b]azepin-3-yl)-1H-pyrazole-1-carboxamide

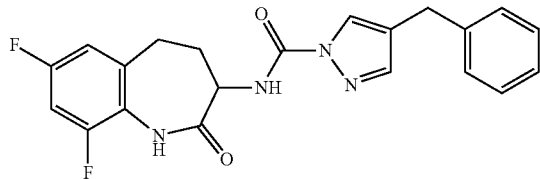 [SMILES: O=C1Nc2c(F)cc(F)cc2CCC1NC(=O)n1cc(Cc2ccccc2)cn1]

The title compound was prepared in a similar fashion to Example 1 with Intermediates 1 and 20. The crude product was purified by column chromatography on NH—SiO$_2$ (Hexanes:EtOAc=1:1) to give 4-benzyl-N-(7,9-difluoro-2-oxo-2,3,4,5-tetrahydro-1H-benzo[b]azepin-3-yl)-1H-pyrazole-1-carboxamide (32%) as a colorless oil. $^1$H-NMR (400 MHz, CDCl$_3$): δ 7.92 (1H, d, J=7.6 Hz), 7.90 (1H, s), 7.46 (1H, s), 7.39 (11H, brs), 7.31-7.17 (4H, m), 6.86-6.74 (2H, m), 4.59-4.52 (1H, m), 3.82 (2H, s), 3.07-2.98 (1H, m), 2.87-2.70 (2H, m), 2.20-2.12 (1H, m). LC-MS: m/z=397.2 [M+H]$^+$.

Example 26: (S)—N-(7,9-difluoro-2-oxo-2,3,4,5-tetrahydro-1H-benzo[b]azepin-3-yl)-4-(3-fluorobenzyl)-1H-pyrazole-1-carboxamide

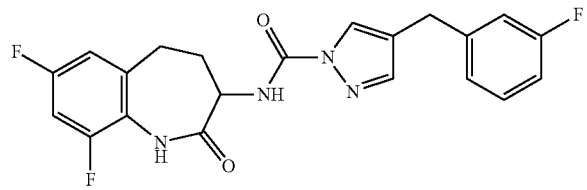 [SMILES: O=C1Nc2c(F)cc(F)cc2CCC1NC(=O)n1cc(Cc2cccc(F)c2)cn1]

The title compound was prepared in a similar fashion to Example 1 with Intermediates 2 and 20. The crude product was purified by column chromatography on NH—SiO$_2$ (Hexanes:EtOAc=2:1) to give (S)—N-(7,9-difluoro-2-oxo-2,3,4,5-tetrahydro-1H-benzo[b]azepin-3-yl)-4-(3-fluorobenzyl)-1H-pyrazole-1-carboxamide (37%) as a white solid. $^1$H-NMR (400 MHz, CDCl$_3$): δ 7.94 (11H, d, J=7.6 Hz), 7.91 (11H, s), 7.46 (1H, s), 7.28-7.23 (2H, m), 6.97-6.82 (4H, m), 4.59-4.53 (1H, m), 3.82 (2H, s), 3.05-2.99 (1H, m), 2.88-2.71 (2H, m), 2.20-2.12 (11H, m). LC-MS: m/z=415.2 [M+H]$^+$.

Example 27: 4-benzyl-N-(7,9-difluoro-1-methyl-2-oxo-2,3,4,5-tetrahydro-1H-benzo[b]azepin-3-yl)-1H-pyrazole-1-carboxamide

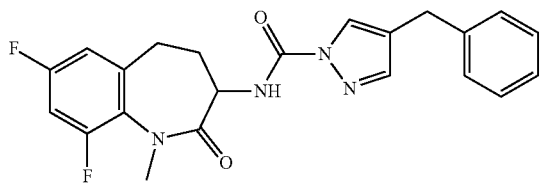 [SMILES: CN1C(=O)C(NC(=O)n2cc(Cc3ccccc3)cn2)CCc2cc(F)cc(F)c21]

The title compound was prepared in a similar fashion to Example 1 with Intermediates 1 and 21. The crude product was purified by column chromatography on NH—SiO$_2$ (Hexanes:EtOAc=2:1) to afford 4-benzyl-N-(7,9-difluoro-1-methyl-2-oxo-2,3,4,5-tetrahydro-1H-benzo[b]azepin-3-yl)-1H-pyrazole-1-carboxamide (56%) as a white solid. $^1$H-NMR (400 MHz, CDCl$_3$): δ 7.98 (1H, d, J=7.6 Hz), 7.88 (1H, s), 7.45 (1H, s), 7.31-7.17 (5H, m), 6.88-6.82 (2H, m), 4.51-4.45 (1H, m), 3.81 (2H, s), 3.34 (3H, d, J=1.6 Hz), 2.93-2.83 (1H, m), 2.73-2.64 (2H, m), 2.11-2.03 (1H, m). LC-MS: m/z=411.2 [M+H]$^+$.

Example 28: N-(7,9-difluoro-1-methyl-2-oxo-2,3,4,5-tetrahydro-1H-benzo[b]azepin-3-yl)-4-(3-fluorobenzyl)-1H-pyrazole-1-carboxamide

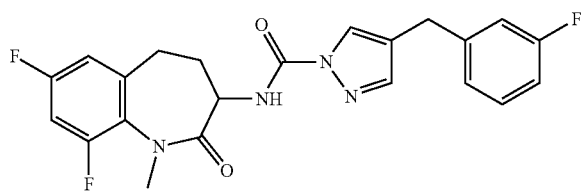

The title compound was prepared in a similar fashion to Example 1 with Intermediates 2 and 21. The crude product was purified by column chromatography on NH—SiO$_2$ (Hexanes:EtOAc=2:1) to afford N-(7,9-difluoro-1-methyl-2-oxo-2,3,4,5-tetrahydro-1H-benzo[b]azepin-3-yl)-4-(3-fluorobenzyl)-1H-pyrazole-1-carboxamide (51%) as a white solid. $^1$H-NMR (400 MHz, CDCl$_3$): δ 8.00 (1H, d, J=7.2 Hz), 7.90 (1H, s), 7.45 (1H, s), 7.27-7.22 (11H, m), 6.96-6.82 (5H, m), 4.51-4.45 (1H, m), 3.81 (2H, s), 3.34 (3H, d, J=2.0 Hz), 2.94-2.84 (11H, m), 2.74-2.63 (2H, m), 2.11-2.04 (1H, m). LC-MS: m/z=429.2 [M+H]$^+$.

Example 29: 4-benzyl-N-(6-oxo-6,7,8,9-tetrahydro-5H-pyrazino[2,3-b]azepin-7-yl)-1H-pyrazole-1-carboxamide

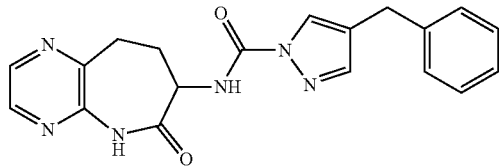 [SMILES: O=C1Nc2nccnc2CCC1NC(=O)n1cc(Cc2ccccc2)cn1]

The title compound was prepared in a similar fashion to Example 1 with Intermediates 1 and 22. The crude product was purified by column chromatography on NH—SiO$_2$ (Hexanes:EtOAc=1:1 to EtOAc only) to afford 4-benzyl-N-(6-oxo-6,7,8,9-tetrahydro-5H-pyrazino[2,3-b]azepin-7-yl)-1H-pyrazole-1-carboxamide (30%) as a white solid. $^1$H-NMR (400 MHz, CDCl$_3$): δ 8.37 (1H, d, J=2.8 Hz), 8.30 (1H, d, J=2.8 Hz), 7.97-7.91 (3H, m), 7.48 (1H, s), 7.32-7.18 (5H, m), 4.60 (1H, dt, J=11.6, 7.6 Hz), 3.83 (2H, s), 3.20-3.16 (2H, m), 3.01-2.91 (1H, m), 2.34-2.25 (1H, m). LC-MS: m/z=363.2 [M+H]$^+$.

Example 30: 4-(3-fluorobenzyl)-N-(6-oxo-6,7,8,9-tetrahydro-5H-pyrazino[2,3-b]azepin-7-yl)-1H-pyrazole-1-carboxamide

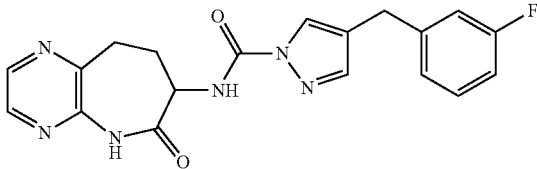 [SMILES: O=C1Nc2nccnc2CCC1NC(=O)n1cc(Cc2cccc(F)c2)cn1]

The title compound was prepared in a similar fashion to Example 1 with Intermediates 2 and 22. The crude product was purified by column chromatography on NH—SiO$_2$ (Hexanes:EtOAc=1:1 to EtOAc only) to afford 4-(3-fluorobenzyl)-N-(6-oxo-6,7,8,9-tetrahydro-5H-pyrazino[2,3-b]azepin-7-yl)-1H-pyrazole-1-carboxamide (35%) as a white solid. $^1$H-NMR (400 MHz, CDCl$_3$): δ 8.38 (1H, d, J=2.8 Hz), 8.30 (1H, d, J=2.4 Hz), 7.98-7.92 (3H, m), 7.48 (1H, s), 7.29-7.23 (1H, m), 6.98-6.87 (3H, m), 4.60 (1H, dt, J=11.6, 7.2 Hz), 3.82 (2H, s), 3.21-3.17 (2H, m), 3.02-2.92 (1H, m), 2.34-2.25 (1H, m). LC-MS: m/z=381.2 [M+H]$^+$.

Example 31: 4-benzyl-N-(5-methyl-6-oxo-6,7,8,9-tetrahydro-5H-pyrazino[2,3-b]azepin-7-yl)-1H-pyrazole-1-carboxamide

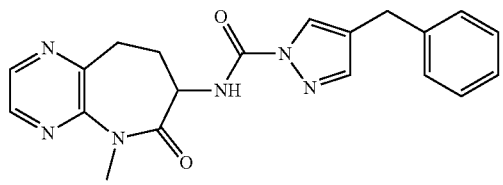 [SMILES: CN1C(=O)C(NC(=O)n2cc(Cc3ccccc3)cn2)CCc2nccnc21]

The title compound was prepared in a similar fashion to Example 1 with Intermediates 1 and 23. The crude product was purified by column chromatography on NH—SiO$_2$ (Hexanes:EtOAc=4:1 to 2:1) to afford 4-benzyl-N-(5-methyl-6-oxo-6,7,8,9-tetrahydro-5H-pyrazino[2,3-b]azepin-7-yl)-1H-pyrazole-1-carboxamide (25%) as a colorless oil. $^1$H-NMR (400 MHz, CDCl$_3$): δ 8.39 (1H, d, J=2.4 Hz), 8.36 (1H, d, J=2.4 Hz), 8.00 (1H, d, J=7.2 Hz), 7.88 (1H, s), 7.47 (1H, s), 7.31-7.17 (5H, m), 4.52 (1H, dt, J=11.6, 8.0 Hz), 3.82 (2H, s), 3.52 (3H, s), 3.09-2.90 (3H, m), 2.28-2.20 (1H, m). LC-MS: m/z=377.2 [M+H]$^+$.

Example 32: (S)-4-benzyl-N-(6-fluoro-5-methyl-4-oxo-2,3,4,5-tetrahydropyrido[4,3-b][1,4]oxazepin-3-yl)-1H-pyrazole-1-carboxamide

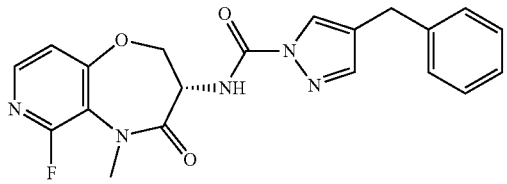 [SMILES: CN1C(=O)[C@@H](NC(=O)n2cc(Cc3ccccc3)cn2)COc2ccnc(F)c21]

To a solution of (S)-6-fluoro-5-methyl-3-((2,2,2-trifluoroacetyl)-14-azanyl)-2,3-dihydropyrido[4,3-b][1,4]oxazepin-4(5H)-one (Intermediate 24) (20 mg, 0.065 mmol) in DCE (0.79 mL) was added TEA (16.4 mg, 0.160 mmol) and di(1H-imidazol-1-yl)methanone (10 mg, 0.0650 mmol) at 0° C. The mixture was stirred at 0° C. for 1 hour. After diluted with water, the mixture was extracted with EtOAc. The separated organic layer was washed with brine, dried over Na$_2$SO$_4$, filtered and concentrated in vacuo. The residue was dissolved in DCE (0.79 mL). After addition of 4-benzyl-1H-pyrazole hydrochloride (Intermediate 1) (15 mg, 0.078 mmol) and TEA (0.210 g, 2.12 mmol) at 0° C., the reaction mixture is stirred at room temperature for 18 hours. After concentration in vacuo, the residue was purified by column chromatography on NH—SiO$_2$ (Hexanes:EtOAc=1:2 to 1:1) to afford (S)-4-benzyl-N-(6-fluoro-5-methyl-4-oxo-2,3,4,5-tetrahydropyrido[4,3-b][1,4]oxazepin-3-yl)-1H-pyrazole-1-carboxamide (31%) as a white foam. $^1$H-NMR (400 MHz, CDCl$_3$): δ 8.09 (1H, d, J=4.8 Hz), 7.98 (1H, d, J=6.4 Hz), 7.87 (1H, dd, J=3.2, 0.8 Hz), 7.48 (1H, s), 7.32-7.28 (1H, m), 7.24-7.17 (3H, m), 7.06 (1H, d, J=5.6 Hz), 4.99-4.88 (1H, m), 4.73 (11H, q, J=9.6 Hz), 4.49-4.43 (2H, m), 3.82 (3H, s), 3.37 (2H, d, J=2.8 Hz). LC-MS: m/z=396.14 [M+H]$^+$.

Example 33: (S)—N-(6-fluoro-5-methyl-4-oxo-2,3,4,5-tetrahydropyrido[4,3-b][1,4]oxazepin-3-yl)-4-(3-fluorobenzyl)-1H-pyrazole-1-carboxamide

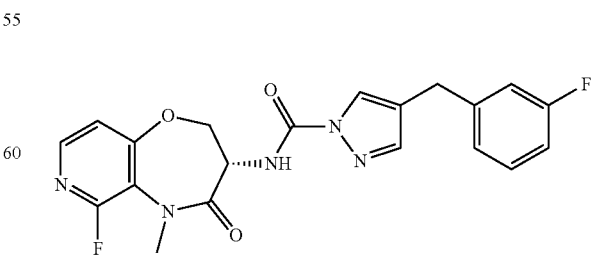

The title compound was prepared in a similar fashion to Example 32 with Intermediates 2 and 24. The crude product was purified by column chromatography on NH—SiO$_2$ (Hexanes:EtOAc=1:2 to 1:1) to give (S)—N-(6-fluoro-5-methyl-4-oxo-2,3,4,5-tetrahydropyrido[4,3-b][1,4]oxazepin-3-yl)-4-(3-fluorobenzyl)-1H-pyrazole-1-carboxamide (11%) as a white foam. $^1$H-NMR (400 MHz, CDCl$_3$): δ 8.01 (1H, dd, J=5.6, 0.8 Hz), 7.99 (1H, d, J=8 Hz), 7.89 (11H, d, J=0.8 Hz), 7.49 (11H, s), 7.06 (11H, d, J=5.6 Hz), 6.97-6.86 (3H, m), 5.33-5.36 (1H, m), 4.99-4.93 (1H, m), 4.74 (1H, q, J=8 Hz), 4.48-4.43 (1H, m), 3.81 (3H, s), 3.38 (2H, d, J=2.8 Hz). LC-MS: m/z=414.13 [M+H]$^+$.

Example 34: (S)-4-benzyl-N-(8-fluoro-5-methyl-4-oxo-2,3,4,5-tetrahydropyrido[4,3-b][1,4]oxazepin-3-yl)-1H-pyrazole-1-carboxamide

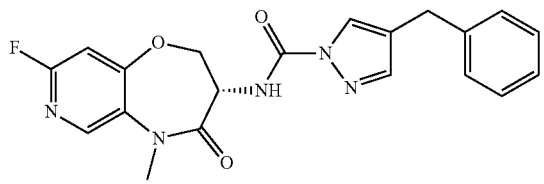 [SMILES: CN1C(=O)[C@@H](NC(=O)n2cc(Cc3ccccc3)cn2)COc2cc(F)ncc21]

The title compound was prepared in a similar fashion to Example 32 with Intermediates 1 and 25. The crude product was purified by column chromatography on NH—SiO$_2$ (Hexanes:EtOAc=2:1 to 1:1) to afford (S)-4-benzyl-N-(8-fluoro-5-methyl-4-oxo-2,3,4,5-tetrahydropyrido[4,3-b][1,4]oxazepin-3-yl)-1H-pyrazole-1-carboxamide (17%) as a white solid. 1H NMR (400 MHz, CDCl$_3$): δ 8.13 (11H, s), 7.99 (1H, d, J=6.8 Hz), 7.88 (1H, s), 7.48 (11H, s), 7.31-7.17 (5H, m), 6.76 (1H, d, J=2.8 Hz), 4.92 (1H, dt, J=11.6, 6.8 Hz), 4.72 (1H, dd, J=10, 6 Hz), 4.47 (1H, dd, J=11.6, 10 Hz), 3.82 (2H, s), 3.48 (3H, s). LC-MS: m/z=396 [M+H]$^+$.

Example 35: (S)—N-(8-fluoro-5-methyl-4-oxo-2,3,4,5-tetrahydropyrido[4,3-b][1,4]oxazepin-3-yl)-4-(3-fluorobenzyl)-1H-pyrazole-1-carboxamide

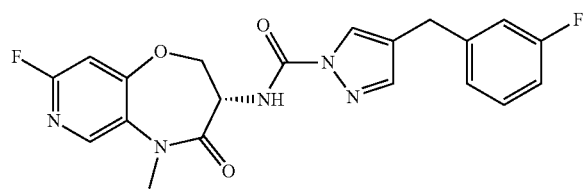 [SMILES: CN1C(=O)[C@@H](NC(=O)n2cc(Cc3cccc(F)c3)cn2)COc2cc(F)ncc21]

The title compound was prepared in a similar fashion to Example 32 with Intermediates 2 and 25. The crude product was purified by column chromatography on NH—SiO$_2$ (Hexanes:EtOAc=2:1 to 1:1) to afford (S)—N-(8-fluoro-5-methyl-4-oxo-2,3,4,5-tetrahydropyrido[4,3-b][1,4]oxazepin-3-yl)-4-(3-fluorobenzyl)-1H-pyrazole-1-carboxamide (24%) as a white solid. $^1$H NMR (400 MHz, CDCl$_3$): δ 8.13 (1H, s), 8.00 (1H, d, J=6.8 Hz), 7.89 (1H, s), 7.48 (1H, s), 7.28-7.23 (1H, m), 7.00-6.83 (3H, m), 6.76 (1H, d, J=2.4 Hz), 4.93 (1H, dt, J=11.6, 6.4 Hz), 4.73, (1H, dd, J=10, 6 Hz), 4.44 (1H, dd, J=11.2, 10 Hz), 3.81 (2H, s), 3.48 (3H, s). LC-MS: m/z=414 [M+H]$^+$.

Example 36: (S)-4-benzyl-N-(8-chloro-5-methyl-4-oxo-2,3,4,5-tetrahydropyrido[4,3-b][1,4]oxazepin-3-yl)-1H-pyrazole-1-carboxamide

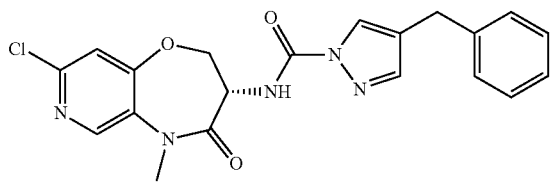 [SMILES: CN1C(=O)[C@@H](NC(=O)n2cc(Cc3ccccc3)cn2)COc2cc(Cl)ncc21]

The title compound was prepared in a similar fashion to Example 32 with Intermediates 1 and 26. The crude product was purified by column chromatography on NH—SiO$_2$ (Hexanes:EtOAc=2:1 to 1:1) to afford (S)-4-benzyl-N-(8-chloro-5-methyl-4-oxo-2,3,4,5-tetrahydropyrido[4,3-b][1,4]oxazepin-3-yl)-1H-pyrazole-1-carboxamide (22%) as a white solid. LC-MS: m/z=412 [M+H]$^+$.

Example 37: (S)-4-benzyl-N-(5,8-dimethyl-4-oxo-2,3,4,5-tetrahydropyrido[4,3-b][1,4]oxazepin-3-yl)-1H-pyrazole-1-carboxamide

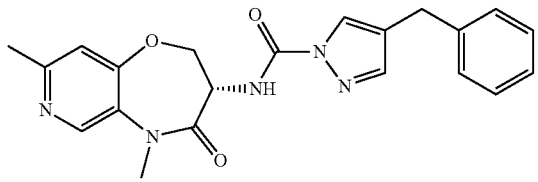 [SMILES: Cc1cc2c(cn1)N(C)C(=O)[C@@H](NC(=O)n1cc(Cc3ccccc3)cn1)CO2]

The title compound was prepared in a similar fashion to Example 32 with Intermediates 1 and 27. The crude product was purified by column chromatography on NH—SiO$_2$ (Hexanes:EtOAc=2:1) to afford (S)-4-benzyl-N-(5,8-dimethyl-4-oxo-2,3,4,5-tetrahydropyrido[4,3-b][1,4]oxazepin-3-yl)-1H-pyrazole-1-carboxamide (31%) as a white solid. LC-MS: m/z=392 [M+H]).

Biological Activity

Cell Culture:

Human colon carcinoma cell HT-29 (KCLB 30038), BV2 mouse microglial cell (cell was a kind gift from Dr. Nak-Yun Sung, Senior researcher at Korea Prime Pharmacy CO., LTD.) and human microglial cell HMC3 (ATCC® CRL-3304™). HT-29 cell was grown in Roswell Park Memorial Institute (RPMI) 1640, BV2 cell was grown in Dulbecco's Modified Eagle's Medium (DMEM) and HMC3 cell was grown in Minimum Essential Media Eagle (MEM) supplemented with 10% fetal bovine serum and 1% mixture of penicillin and streptomycin (Gibco). Cells were maintained at 37° C. in a humidified 5% CO$_2$ atmosphere.

Cell-Based Necroptosis Assay for RIPK1 Activity:

To measure the activity of RIPK1 inhibitor in necroptotic cells, HT-29 cells were treated by control DMSO, human TNFα (Peprotech, Rocky Hill, USA), SM-164 (Biovision, California, USA) and a pan-caspase inhibitor Z-VAD-FMK (Invivogen, San Diego, USA). Cells were pretreated with Z-VAD-FMK 20 μM. After 30 min, human TNFα 10 ng/ml, SM-164 100 nM and RIPK1 Inhibitor (0.0001, 0.001, 0.01, 0.02, 0.05, 0.1, 1, 10 uM) were treated for 24 h. Cell viability was measured by Cell Counting Kit 8 (CCK-8) (Dong-in, Seoul, Korea).

Immunoblotting:

Biological activity of the compounds of RIPK1 inhibitor was determined by measuring their ability to inhibitor TNFα induced phospho-RIPK1 (ser 166) levels, phospho-RIPK3 levels, phospho-MLKL levels in HMC3 cells. Cells were pretreated with Z-VAD-FMK 20 μM. After 30 min, human TNFα 20 ng/ml, SM-164 100 nM and RIPK1 inhibitor (0.1, 1, 10 nM) were treated for 7 h under serum free media. Cells were lysed with cold lysis buffer containing 25 mM HEPES pH 7.6, 150 nM NaCl, 1% NP40, 1% sodium deoxycholate, 0.1% SDS, and protease inhibitor mixture (Bimake, Houston, USA) using sonicators. The cells were centrifuged at 15,000 rpm, 4° C. for 5 min. After protein concentration of the lysates (supernatants) was quantified using BCA assay (Thermo Fisher Scientific, Waltham, USA), lysates were mixed with LDS sample buffer and heating at 70 for 10 min. (Invitrogen, California, USA). Extracts were separated by sodium dodecyl sulfate polyacrylamide gel electrophoresis (SDS-PAGE) followed by electro-transfer to polyvinylidene difluoride (PVDF) membranes and probed with an anti-phospho-RIPK1 antibody, anti-phospho-RIPK3 antibody and anti-phospho-MLKL antibody (Cell Signaling technology, Danvers, USA) and β-actin (Proteintech, Rosement, USA), followed by horseradish peroxidase conjugated anti-rabbit (Cell Signaling technology, Danvers, USA), anti-mouse IgG and revealed with Super Signal West dura kit (Pierce). The membranes are placed in an image analyzer (Imagequant, LAS 500, GE Healthcare), connected to a computer which allows the image generation (software Image reader LAS 500).

Inflammation Cytokine:

Total RNA was extracted and purified from PureLink™ RNA mini kit (Thermo Fisher Scientific, Waltham, USA) according to the manufacture's protocol. Reverse transcription reactions were performed with AccuPower CycleScript RT PreMix (dT20) (Bioneer, Daejeon, Korea). Synthesis of cDNA was carried out using SimpliAmp Thermal Cycler (Applied Biosystems, Carlsbad, CA) and RT-PCR conditions were 15° C. for 30 sec, 42° C. for 4 min, 55° C. for 30 sec in 12 cycles, and heat inactivation was performed 95° C. for 5 min. For qPCR, SYBR Green PCR Master Mix (Thermo Fisher Scientific, Waltham, USA) was used in QuantStudio 3 (Applied Biosystems, Carlsbad, CA) and the PCR conditions were 95° C. for 10 min, 40 cycles of 95° C. for 15 s, and 60° C. for 30 s. The relative mRNA levels were calculated using cycle threshold (Ct) method. GAPDH was used as the endogenous control. PCR primers used in this study are listed in Table 1.

TABLE 1

PCR primers used in this study.

| Primer | Species | | Sequence | SEQ ID NO: |
|---|---|---|---|---|
| TNF-a | mouse | Forward | TGTAGCCCACGTCGTAGCAA | 1 |
| | | Reverse | AGGTACAACCCATCGGCTGG | 2 |
| IL-1β | mouse | Forward | TGTGCAAGTGTCTGAAGCAGC | 3 |
| | | Reverse | TGGAAGCAGCCCTTCATCTT | 4 |
| IL-6 | mouse | Forward | CCACTTCACAAGTCGGAGGC | 5 |
| | | Reverse | GCCATTGCACAACTCTTTTCTC | 6 |
| GAPDH | mouse | Forward | TCACCACCATGGAGAAGGC | 7 |
| | | Reverse | GCTAAGCAGTTGGTGGTGCA | 8 |

| | | HT29 (human colon cancer) Necroptosis inhibition | | | BV2 (mouse microglia) Pro-inflammation cytokine inhibition | | |
|---|---|---|---|---|---|---|---|
| Example Number | Necroptosis inhibition (IC50, nM) | p-RIPK1 inhibition (nM) | p-RIPK3 inhibition (nM) | p-MLKL inhibition (nM) | TNF-a (uM) | IL-1β (uM) | IL-6 (uM) |
| 1 | <100 | — | — | — | — | — | — |
| 2 | <100 | — | — | — | — | — | — |
| 3 | <10 | >10 | >10 | >10 | >10 | >100 | >10 |
| 4 | <10 | — | — | — | — | — | — |
| 5 | <10 | >10 | >100 | >100 | >100 | >100 | >100 |
| 6 | <100 | — | — | — | — | — | — |
| 7 | <10 | — | — | — | — | — | — |
| 8 | <100 | — | — | — | — | — | — |
| 9 | <100 | — | — | — | — | — | — |
| 10 | <100 | — | — | — | — | — | — |

-continued

| | Necroptosis inhibition (IC50, nM) | HT29 (human colon cancer) Necroptosis inhibition | | | BV2 (mouse microglia) Pro-inflammation cytokine inhibition | | |
|---|---|---|---|---|---|---|---|
| Example Number | | p-RIPK1 inhibition (nM) | p-RIPK3 inhibition (nM) | p-MLKL inhibition (nM) | TNF-a (uM) | IL-1β (uM) | IL-6 (uM) |
| 11 | <100 | — | — | — | — | — | — |
| 12 | <10 | >10 | >10 | >10 | >100 | >10 | >100 |
| 13 | <10 | >10 | >10 | >10 | >100 | >10 | >100 |
| 14 | <100 | — | — | — | — | — | — |
| 15 | >100 | — | — | — | — | — | — |
| 16 | <10 | >10 | >10 | >10 | >100 | >10 | >10 |
| 17 | <10 | >10 | >10 | >10 | >100 | >10 | >10 |
| 18 | <10 | <100 | <100 | <100 | >100 | >10 | >100 |
| 19 | <10 | >10 | >10 | >10 | >100 | >100 | >10 |
| 20 | <10 | >10 | <100 | >10 | >100 | >100 | >10 |
| 21 | <10 | >10 | >10 | >10 | >100 | >100 | >10 |
| 22 | <10 | — | — | — | — | — | — |
| 23 | <10 | — | — | — | — | — | — |
| 24 | <100 | — | — | — | — | — | — |
| 25 | <100 | — | — | — | — | — | — |
| 26 | <10 | >10 | <100 | >10 | >10 | >10 | >10 |
| 27 | <10 | >10 | >10 | <100 | >100 | >100 | >10 |
| 28 | <10 | >10 | >10 | >10 | >10 | >10 | >10 |
| 29 | >100 | — | — | — | — | — | — |
| 30 | >100 | — | — | — | — | — | — |
| 31 | >100 | — | — | — | — | — | — |
| 32 | <10 | >10 | — | >10 | — | — | — |
| 33 | <100 | >10 | — | >10 | — | — | — |
| 34 | <10 | >1 | — | >10 | — | — | — |
| 35 | <10 | >1 | — | >10 | — | — | — |
| 36 | <10 | — | — | — | — | — | — |
| 37 | <10 | — | — | — | — | — | — |

What is claimed is:

1. A compound of Formula IIa:

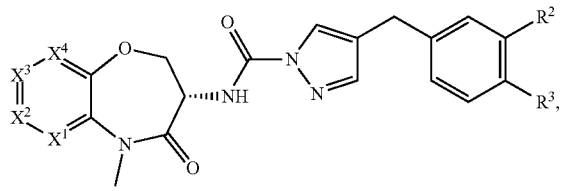

IIa wherein the compound is:
- (S)—N-(6-fluoro-5-methyl-4-oxo-2,3,4,5-tetrahydrobenzo[b][1,4]oxazepin-3-yl)-4-(3-fluorobenzyl)-1H-pyrazole-1-carboxamide;
- (S)—N-(6,8-difluoro-5-methyl-4-oxo-2,3,4,5-tetrahydrobenzo[b][1,4]oxazepin-3-yl)-4-(3-fluorobenzyl)-1H-pyrazole-1-carboxamide;
- (S)-4-(3-fluorobenzyl)-N-(7-methoxy-5-methyl-4-oxo-2,3,4,5 tetrahydrobenzo[b][1,4]oxazepin-3-yl)-1H-pyrazole-1-carboxamide; or
a pharmaceutically acceptable salt thereof.

2. The compound of claim 1, wherein the compound inhibits activity of a receptor interacting protein kinase 1 (RIPK1).

3. A method for inhibiting an RIPK1 enzyme in a cell, comprising the step of contacting with the cell with the compound of claim 1 in an amount sufficient to inhibit an activity of the RIPK1 enzyme.

4. A method for alleviating or ameliorating symptoms of an RIPK1 mediated disease or condition by inhibiting RIPK1 activity, the method comprising administering to a subject in need thereof a therapeutically effective amount of a composition comprising the compound of claim 1 or a pharmaceutically acceptable salt, solvate, polymorph, ester, tautomer or pro-drug thereof, wherein the RIPK mediated disease or condition is a disease related to inflammation and necroptotic cell death.

5. The method of claim 4, wherein the disease related to inflammation and necroptotic cell death is selected from the group consisting of pancreatic cancer, lung cancer, colon cancer, gastric cancer, glioblastoma, melanoma, multiple sclerosis, psoriasis, colitis, rheumatoid arthritis, sepsis, renal and brain ischemia-reperfusion injury, Alzheimer's disease, amyotrophic lateral sclerosis (ALS), Parkinson's disease, dermatitis, and asthma.

6. The method of claim 4, further comprising administering an effective amount of one or more therapeutic agents.

7. A pharmaceutical composition for alleviating or ameliorating symptoms of an RIPK1 mediated disorder or condition by inhibiting RIPK1 activity, comprising:
   a) an effective amount of the compound of claim 1, or a pharmaceutically acceptable salt, solvate, polymorph, ester, tautomer or prodrug thereof; and
   b) one or more therapeutic agents,
   wherein the RIPK1 mediated disease or condition is selected from the group consisting of pancreatic cancer, lung cancer, colon cancer, gastric cancer, glioblastoma, melanoma, multiple sclerosis, psoriasis, colitis, rheumatoid arthritis, sepsis, renal and brain ischemia-reperfusion injury, Alzheimer's disease, amyotrophic lateral sclerosis (ALS), Parkinson's disease, dermatitis, and asthma.

8. The pharmaceutical composition of claim 7, wherein the pharmaceutical composition is formulated for oral administration.

9. The pharmaceutical composition of claim 8, wherein the pharmaceutical composition is in a form of a tablet or capsule.

10. The pharmaceutical composition of claim 8, wherein the amount of the compound of claim 4 is in a range of 0.001 to 1000 mg/kg body weight/day.

11. The pharmaceutical composition of claim 10, wherein the amount of the compound of claim 4 is in a range of 0.5 to 50 mg/kg body weight/day.

12. The method of claim 3, wherein the compound inhibits necroptosis in a cancer cell.

13. The method of claim 3, wherein the compound decreases protein level of RIPK1 in a microglial cell.

14. The method of claim 3, wherein the compound decreases mRNA level of TNF-alpha, IL-beta, and IL-6 in a microglial cell.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Forward mouse TNF-alpha

```
<400> SEQUENCE: 1
tgtagcccac gtcgtagcaa                                               20

<210> SEQ ID NO 2
<211> LENGTH: 20
<212> TYPE: DNA
<213> ORGANISM: Artificial Sequence
<220> FEATURE:
<223> OTHER INFORMATION: Reverse mouse TNF-alpha

<400> SEQUENCE: 2
aggtacaacc catcggctgg                                               20

<210> SEQ ID NO 3
<211> LENGTH: 21
<212> TYPE: DNA
<213> ORGANISM: Artificial Sequence
<220> FEATURE:
<223> OTHER INFORMATION: Forward mouse IL-1beta

<400> SEQUENCE: 3
tgtgcaagtg tctgaagcag c                                             21

<210> SEQ ID NO 4
<211> LENGTH: 20
<212> TYPE: DNA
<213> ORGANISM: Artificial Sequence
<220> FEATURE:
<223> OTHER INFORMATION: Reverse mouse IL-1beta

<400> SEQUENCE: 4
tggaagcagc ccttcatctt                                               20

<210> SEQ ID NO 5
<211> LENGTH: 20
<212> TYPE: DNA
<213> ORGANISM: Artificial Sequence
<220> FEATURE:
<223> OTHER INFORMATION: Forward mouse IL-6

<400> SEQUENCE: 5
ccacttcaca agtcggaggc                                               20

<210> SEQ ID NO 6
<211> LENGTH: 22
<212> TYPE: DNA
<213> ORGANISM: Artificial Sequence
<220> FEATURE:
<223> OTHER INFORMATION: Reverse mouse IL-6

<400> SEQUENCE: 6
gccattgcac aactcttttc tc                                            22

<210> SEQ ID NO 7
<211> LENGTH: 19
<212> TYPE: DNA
<213> ORGANISM: Artificial Sequence
<220> FEATURE:
<223> OTHER INFORMATION: Forward mouse GAPDH

<400> SEQUENCE: 7
tcaccaccat ggagaaggc                                                19

<210> SEQ ID NO 8
<211> LENGTH: 20
```

```
<212> TYPE: DNA
<213> ORGANISM: Artificial Sequence
<220> FEATURE:
<223> OTHER INFORMATION: Reverse mouse GAPDH

<400> SEQUENCE: 8
gctaagcagt tggtggtgca                                              20
```